United States Patent
Reddy

(10) Patent No.: US 10,167,265 B2
(45) Date of Patent: Jan. 1, 2019

(54) TREATMENT OF PULMONARY AND OTHER CONDITIONS

(71) Applicants: University of Pittsburgh—Of the Commonwealth System of Higher Education, Pittsburgh, PA (US); The United States of America as Represented by the Department of Veterans Affairs, Washington, DC (US)

(72) Inventor: Raju Reddy, Cheswick, PA (US)

(73) Assignees: University of Pittsburgh—Of the Commonwealth System of Higher Education, Pittsburgh, PA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/828,163

(22) Filed: Nov. 30, 2017

(65) Prior Publication Data

US 2018/0086723 A1    Mar. 29, 2018

Related U.S. Application Data

(62) Division of application No. 14/890,147, filed as application No. PCT/US2014/037548 on May 9, 2014, now Pat. No. 9,862,690.

(60) Provisional application No. 61/822,224, filed on May 10, 2013.

(51) Int. Cl.
| | |
|---|---|
| C07D 241/20 | (2006.01) |
| C07D 239/26 | (2006.01) |
| C07D 239/30 | (2006.01) |
| C07D 239/34 | (2006.01) |
| C07D 239/38 | (2006.01) |
| C07D 239/42 | (2006.01) |
| C07D 239/47 | (2006.01) |
| C07D 239/52 | (2006.01) |
| C07D 241/12 | (2006.01) |
| C07D 241/16 | (2006.01) |
| C07D 241/18 | (2006.01) |

(52) U.S. Cl.
CPC ......... *C07D 241/20* (2013.01); *C07D 239/26* (2013.01); *C07D 239/30* (2013.01); *C07D 239/34* (2013.01); *C07D 239/38* (2013.01); *C07D 239/42* (2013.01); *C07D 239/47* (2013.01); *C07D 239/52* (2013.01); *C07D 241/12* (2013.01); *C07D 241/16* (2013.01); *C07D 241/18* (2013.01)

(58) Field of Classification Search
None
See application file for complete search history.

(56) References Cited

U.S. PATENT DOCUMENTS

| | | | |
|---|---|---|---|
| 4,313,948 A | 2/1982 | Ondetti et al. | |
| 5,672,731 A | 9/1997 | Chen | |
| 6,747,055 B1 | 6/2004 | Ho | |
| RE39,151 E | 6/2006 | Vankeepuram et al. | |
| 7,550,486 B2 | 6/2009 | Ko | |
| 8,188,292 B2 | 5/2012 | Loso et al. | |
| 2006/0276536 A1 | 12/2006 | Vander Jagt et al. | |
| 2007/0270464 A1* | 11/2007 | Liotta | C07D 211/74 514/318 |
| 2011/0039769 A1 | 2/2011 | Tagmose et al. | |

FOREIGN PATENT DOCUMENTS

| | | |
|---|---|---|
| CN | 101475532 | 7/2009 |
| CN | 10344958 | 11/2011 |
| CN | 103086958 | 5/2013 |
| EP | 0 934 941 | 8/1999 |
| JP | 63-139339 | 6/1988 |
| JP | 2009-544608 | 12/2009 |
| JP | 2012-525418 | 10/2012 |
| WO | WO 2004/043349 | 5/2004 |
| WO | WO 2005/013966 | 2/2005 |
| WO | WO 2007/098504 | 8/2007 |
| WO | WO 2008/144011 | 11/2008 |
| WO | WO 2010/059245 | 5/2010 |
| WO | WO 2011/033115 | 3/2011 |

OTHER PUBLICATIONS

Ashok et al., "Microwave-assisted solvent-free synthesis of (2E,6E)-2,6-bis[(3-aryl)-1-phenyl-1H-pyrazol-4-ylmethylene]cycloalkanones," *Indian Journal of Heterocyclic Chemistry*, 19(4): 313-316, 2010 (abstract only).
Chan et al., "Nucleophile-Initiated Thiol-Michael Reactions: Effect of Organocatalyst, Thiol, and Ene," *Macromolecules*, 43(15): 6381-6388, Jul. 14, 2010.
Ebersberg et al., "Heterocycle-substituted 3-pentadienones," *Naturwissenschaften*, 52(18): 514, 1965 (abstract only).
Examination Report issued by Australian Patent Office dated Nov. 9, 2017, for AU Application No. 2014262471.
Extended European Search Report issued for European Application No. 14793993.8 dated Sep. 14, 2016.
First Office Action issued for Chinese Application No. 201480033249.0 by the State Intellectual Property Office of China on Nov. 17, 2016 (with English translation).
Fresenius et al., "The reaction between barbituric acid and hydroxymethyl compounds II," *Arzneimittel-Forschung*, pp. 28-38, 1952 (abstract only).
Hung et al., "The reaction of 4-formylsydnone and methyl ketones," *Journal of the Chinese Chemical Society*, 40(4): 385-391, 1993 (abstract only).

(Continued)

*Primary Examiner* — Jean P Cornet
(74) *Attorney, Agent, or Firm* — Klarquist Sparkman, LLP

(57) ABSTRACT

Disclosed is a compound, or a pharmaceutically acceptable salt or ester thereof, having a structure of:

$X^1\text{-L-}X^2$ wherein L is a linking moiety comprising an enone; and $X^1$ and $X^2$ are each independently an optionally-substituted N-heterocycle.
Also disclosed are method for treating pulmonary conditions and other organ or system conditions with the compounds.

20 Claims, 22 Drawing Sheets

(56) References Cited

OTHER PUBLICATIONS

International Search Report and Written Opinion issued for International Application No. PCT/US2014/037548 dated Nov. 20, 2014.
Li et al., "Investigation into thiol-(meth)acrylate Michael addition reactions using amine and phosphine catalysts," *Polym. Chem.*, Issue 8, pp. 1196-1204, Jun. 7, 2010.
Mather et al., "Michael addition reactions in macromolecular design for emerging technologies," *Progress in Polymer Science*, 31(5): 487-531, May 2006.
Cao et al., "Synthesis of the pyridinyl analogues of dibensylideneactone (pyr-dba) via an improved Claisen-Schmidt condensation, displaying diverse biological activities as curcumin analogues," *Organic & Biomolecular Chemistry*, vol. 10, pp. 1239-1245, 2012.
Wei et al., "Effects of Pyridine Analogs of Curcumin on Growth, Apoptosis and NF-kB Activity in Prostate Cancer PC-3 Cells," *Anticancer Research*, 33(4): 1343-1350, Apr. 2013.
Yadav et al., "Synthesis and cytotoxic potential of heterocyclic cyclohexanone analogues of curcumin," *Bioorganic & Medicinal Chemistry*, vol. 18, pp. 6701-6707, 2010.
Mulliner et al., "Predicting Michael-acceptor reactivity and toxicity through quantum chemical transition-state calculations," *Organic & Biomolecular Chemistry*, Issue 24, pp. 8400-8412, Sep. 5, 2011.
Potapov et al., "Sintez formilnykh proizvodnykh 1-ethylpirazola, bis-(3,5-dimethyl-1-pirazolyl)metana i azometinov na ikh osnove," *Journal organicheskoi khimii*, 42(4): 569-573, 2006.
Sun et al., "Curcumin analog cytotoxicity against breast cancer cells: exploitation of a redox-dependent mechanism," *Bioorganic & Medicinal Chemistry Letters*, 19(23): 6627-6631, 2009.
Wada et al., "Novel molecules for photorefractive application," *Molecular Crystals and Liquid Crystals Science and Technology, Section A: Molecular Crystals and Liquid Crystals*, 280(1): 71-78, 1996 (abstract only).
Wang et al., "Synthesis and biological activity of 1,5-bis(substituted pyrazol-4-yl)-1,4-pentadien-3-one-derivatives," *Youji Huaxue*, 29(9): 1412-1418, 2009 (abstract only).
Weber et al., "Activation of NFkB is Inhibited by curcumin and related enones," *Bioorganic & Medicinal Chemistry*, vol. 14, pp. 2450-2461, available online Dec. 7, 2005.
Zheng et al., "Synthesis, Chemical Reactivity as Michael Acceptors, and Biological Potency of Monocyclic Cyanoenones, Novel and Highly Potent Anti-Inflammatory and Cytoprotective Agents," *Journal of Medicinal Chemistry*, 55(1): 4837-4846, Apr. 25, 2012.

\* cited by examiner

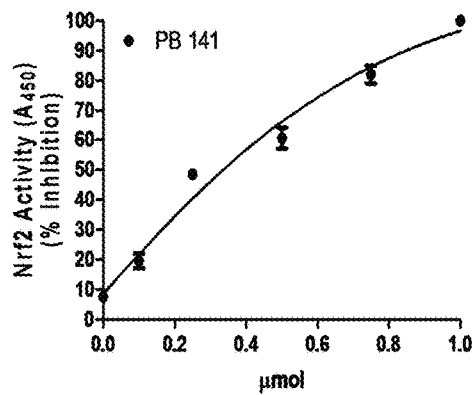
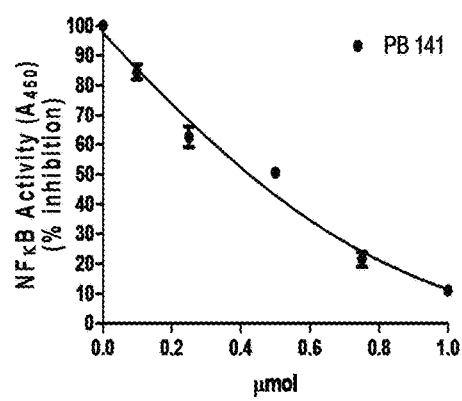
FIG. 6A            FIG. 6B
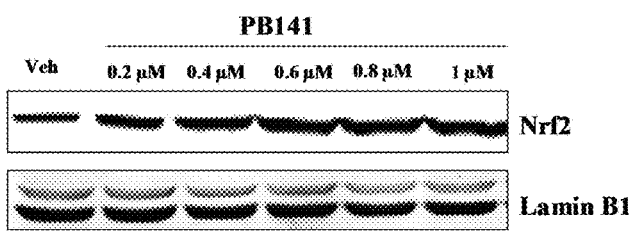
FIG. 6C
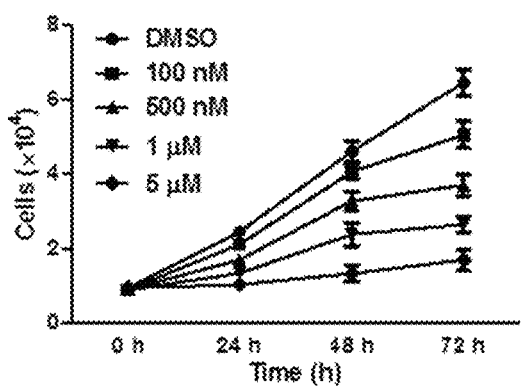
FIG. 7

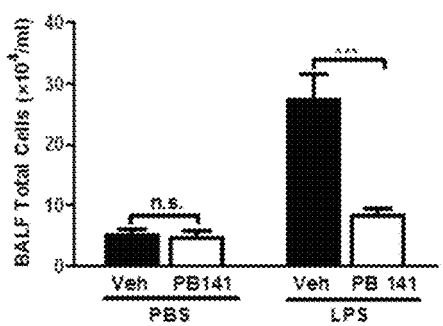
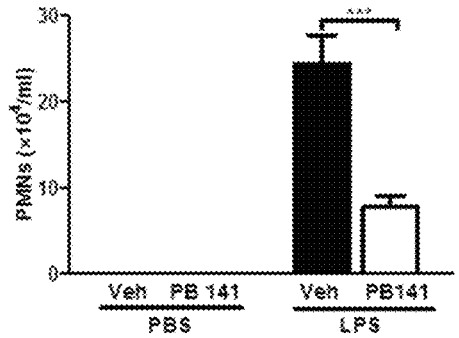
FIG. 10A                FIG. 10B
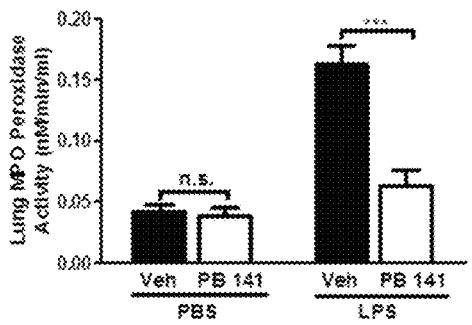
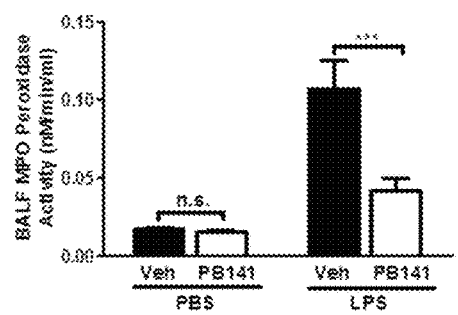
FIG. 10C                FIG. 10D
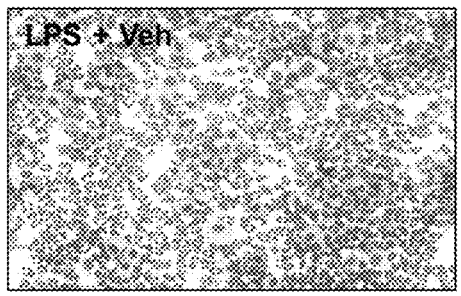
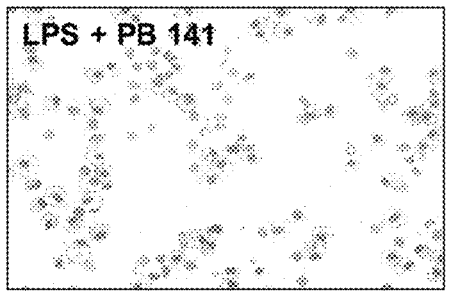
FIG. 10E

TREATMENT OF PULMONARY AND OTHER CONDITIONS

This application is a divisional of U.S. application Ser. No. 14/890,147, filed Nov. 9, 2015, which is the U.S. National Stage of International Application No. PCT/US2014/037548, filed May 9, 2014, which was published in English under PCT Article 21(2), which in turn claims the benefit of U.S. Provisional Application No. 61/822,224, filed May 10, 2013. The provisional application is incorporated by reference herein in its entirety.

ACKNOWLEDGMENT OF GOVERNMENT SUPPORT

This invention was made with government support under grant number HL093196 awarded by National Institutes of Health. The government has certain rights in the invention.

BACKGROUND

The lung is an organ that is dependent on delicate structures such as the alveolar-capillary interface for its crucial gas-exchange function, yet is routinely exposed to toxins and irritants in the inspired air. It can also be injured by toxins and inflammatory products generated by infections and derangements elsewhere in the body. It is thus subject to a wide variety of diseases, for many of which the pathogenesis is incompletely known. Some of these diseases and conditions have effective treatments available; these treatments may include administration of steroids, other anti-inflammatory agents, small molecules, or therapeutic antibodies. However, for some diseases and conditions and subsets of patients with other conditions, efficacy of all available treatments is limited. The most commonly employed treatment in many cases is corticosteroid administration, which is often associated with significant adverse effects.

Pulmonary fibrosis is a lung disease that can result from exposure to radiation, from infections, from inflammatory processes, or from autoimmune disorders. In other cases, known as idiopathic pulmonary fibrosis (IPF), the cause is unknown. Regardless of the triggering insult, the outcome is uncontrollable inflammation, immune activity, lung injury/repair, and fibrotic processes that damage the lung. The scarring of the lungs that occurs in these diseases reduces the ability of the lungs to transfer oxygen into the blood, causing hypoxemia. A primary aim of a treatment for pulmonary fibrosis is to reduce inflammation and injury and enhance lung repair, and thus to halt the abnormal processes that result in irreversible fibrosis. Currently available therapies for pulmonary fibrosis are very limited.

Chronic obstructive pulmonary disease (COPD) is a growing problem. Patients present with symptoms of cough, excessive production of mucus, and dyspnea that may be connected with bronchitis or emphysema. While bronchitis represents inflammation of the airways, emphysema is a more advanced disease representing destruction of the lung parenchyma by oxidants and proteases released as part of the inflammatory process. Development of COPD is most often attributed to smoking or exposure to environmental toxins over a period of many years, although the disease continues to progress even after smoking cessation. The pathophysiology in COPD also features "steroid resistance," mediated by reduced HDAC (histone deacetylase) enzyme activity. As a result, the most commonly used anti-inflammatory drug has little effect and is incapable of halting progression. The only treatment available for COPD is administration of drugs that alleviate the symptoms.

A pulmonary disease with symptoms often overlapping those of COPD is asthma. Airway inflammation in asthma is characterized by activation of a variety of immune-system cells. Asthma pathology features increased production of a number of cytokines, primarily of the Th2 class associated with adaptive immunity, together with tissue eosinophilia and increased IgE production. A diagnostic feature of asthma is excessive response of the airways to bronchoconstrictors such as methacholine. The most effective therapy for asthma remains corticosteroids, typically administered by inhalation. Bronchodilators are also employed, frequently in combination with corticosteroids. Some patients, however, exhibit "steroid resistant" asthma that does not respond to corticosteroids.

Cystic fibrosis is a genetic disease affecting a chloride ion channel in the membrane of epithelial cells. Failure of chloride ion transport results in production of thick, viscous secretions. Mucus production in the lungs is among the many secretions affected. A prominent feature of cystic fibrosis is inflammation that is only partially due to the frequent infections that are also a feature of the disease. This neutrophil-rich inflammation is one factor in the gradual loss of lung function that eventually leads to death. Therapies involved in attenuating lung function decline are limited.

ALI (acute lung injury) and ARDS (acute respiratory distress syndrome) are lung diseases that can result from a wide variety of injuries either intrinsic or extrinsic to the lung. In the acute phase there is sloughing of both bronchial and alveolar epithelial cells, with formation of protein-rich hyaline membranes on the denuded basement membrane. This leads to inflammation, with neutrophils adhering to the injured capillary endothelium and migrating through the interstitium into the air space. In the air space, alveolar macrophages secrete pro-inflammatory cytokines, which act locally to stimulate chemotaxis and activate neutrophils that release oxidants, proteases, leukotrienes, and other proinflammatory molecules, such as platelet-activating factor. The oxidants and proteases produce more injury, and the cycle continues. There is no approved pharmacological therapy for ALI/ARDS.

Ischemia-reperfusion injury occurs when blood flow returns to an organ that has been starved of oxygen. Ischemia followed by reperfusion is inevitable in organ transplantation but also accompanies such conditions as myocardial infarction and stroke. The mechanisms involved are complex but involvement of inflammation and associated production of reactive oxygen species is common. Reactive oxygen species are strong oxidants that can damage components of many cells. Organs can only withstand a limited period of ischemia before suffering injury on reperfusion. Attempts to extend this period by treatments prior to transplantation have had limited success and post-transplantation treatments appear even less useful. The most effective current method for extending the permissible period of ischemia is by reducing the organ's metabolic rate during the period between harvest and reimplantation.

Pulmonary hypertension is defined as abnormally high blood pressure specifically in the vasculature of the lungs. It is usually secondary to conditions that limit pulmonary blood flow or oxygenation but may also occur without identifiable cause. A key feature of the pathogenesis is abnormal proliferation of vascular cells together with failure of appropriate apoptosis. Current management focuses on vasodilators and symptom-reducing strategies, but compounds that block cell proliferation and other pathways are now being investigated.

Lung cancer is the leading cause of cancer death in the US, with only 16% of patients diagnosed with lung cancer surviving as much as five years. It is estimated that 80%-90% of all lung cancers are the result of cigarette smoke. Like other environmental carcinogens, which may also induce lung cancer, the carcinogens in cigarette smoke cause mutations that lead to uncontrolled proliferation of the affected cells and also allow them to invade normal tissues. Treatments are surgery, radiation, and chemotherapy, with the choice depending to some extent on the specific type of cancer involved, but only surgical removal of a tumor that has not yet spread provides any hope for long-term survival. As the poor long-term survival statistics indicate, better treatments are needed.

SUMMARY

One embodiment disclosed herein relates to a compound, or a pharmaceutically acceptable salt or ester thereof, having a structure of:

$X^1$-L-$X^2$ wherein L is a linking moiety comprising an enone; and
$X^1$ and $X^2$ are each independently an optionally-substituted N-heterocycle.

A further embodiment disclosed herein relates to a compound, or a pharmaceutically acceptable salt or ester thereof, comprising an adduct of a hydrophilic thiol and an enone that comprises at least two N-heterocycles.

An additional embodiment disclosed herein relates to a compound, or a pharmaceutically acceptable salt or ester thereof, having a structure of:

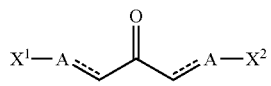

(Formula I)

wherein  represents a single bond or a double bond;
A is CH if  is a double bond, or CH(S—$R^5$) if  is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl; and
$X^1$ and $X^2$ are each independently an optionally-substituted N-heterocycle; or

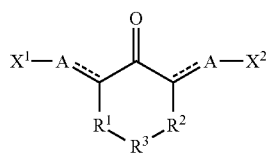

(Formula II)

wherein  represents a single bond or a double bond;
A is CH if  is a double bond, or CH(S—$R^5$) if  is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;
$X^1$ and $X^2$ are each independently an optionally-substituted N-heterocycle; and
$R^1$, $R^2$, and $R^3$ are each independently C or N; or

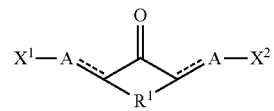

(Formula III)

wherein  represents a single bond or a double bond;
A is CH if  is a double bond, or CH(S—$R^5$) if  is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;
$X^1$ and $X^2$ are each independently an optionally-substituted N-heterocycle; and
$R^1$ is C or N; or

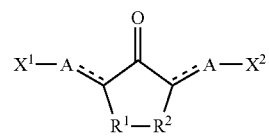

(Formula IV)

wherein  represents a single bond or a double bond;
A is CH if  is a double bond, or CH(S—$R^5$) if  is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;
$R^1$ and $R^2$ are each independently C or N; and
$X^1$ and $X^2$ are each independently an optionally-substituted N-heterocycle.

Also disclosed herein are pharmaceutical compositions comprising a compound disclosed herein, and at least one pharmaceutically acceptable excipient.

Further disclosed is a method for treating a pulmonary disease in a subject comprising administering to the subject in need thereof a therapeutically effective amount of a compound or pharmaceutical composition disclosed herein.

Additionally disclosed is a method for treating an ischemia-reperfusion condition in a subject comprising administering to the subject in need thereof a therapeutically effective amount of a compound or pharmaceutical composition disclosed herein.

Also disclosed herein is a method of inhibiting NF-κB activity in a subject, comprising administering to the subject in need thereof an inhibitory amount of a compound or pharmaceutical composition disclosed herein.

Further disclosed herein is a method of inhibiting lung fibroblast proliferation in a subject, comprising administering to the subject in need thereof an inhibitory amount of a compound or pharmaceutical composition disclosed herein.

Additionally disclosed herein is a method of inhibiting myofibroblast differentiation in a subject, comprising administering to the subject in need thereof an inhibitory amount of a compound or pharmaceutical composition disclosed herein.

Also disclosed herein is a method of inhibiting an oxidizing agent in lung tissue of a subject, comprising administering to the subject in need thereof a therapeutically effective amount of a compound or pharmaceutical composition disclosed herein.

Further disclosed herein is a method of ameliorating or preventing acute or chronic rejection of a transplanted organ in a subject, comprising administering to the subject in need thereof a therapeutically effective amount of a compound or pharmaceutical composition disclosed herein.

Additionally disclosed herein is a method for increasing a subject's endogenous antioxidant activity via upregulation of the activity of the transcription factor Nrf2, comprising administering to the subject in need thereof a therapeutically effective amount of a compound or pharmaceutical composition disclosed herein.

Also disclosed herein is a method for inhibiting pulmonary collagen deposition in a subject, comprising administering to the subject in need thereof a therapeutically effective amount of a compound or pharmaceutical composition disclosed herein.

Further disclosed herein is a method for decreasing proliferation and inducing apoptosis in lung cancer cells, comprising contacting the cells with an effective amount of a compound or pharmaceutical composition disclosed herein.

Additionally disclosed herein is method for improving the phagocytotic ability of alveolar macrophages, comprising contacting the microphages with an effective amount of a compound or pharmaceutical composition disclosed herein.

Also disclosed herein is a method for diminishing the inflammatory response to allergen in a subject, comprising administering to the subject in need thereof a therapeutically effective amount of a compound or pharmaceutical composition disclosed herein.

Further disclosed herein is a method for diminishing the inflammatory response to an inflammatory, irritating, or cytotoxic agent in a subject, comprising administering to the subject in need thereof a therapeutically effective amount of a compound or pharmaceutical composition disclosed herein.

Additionally disclosed herein is a method for diminishing allergen-induced excessive response to bronchoconstrictors (e.g., methacholine) in a subject, comprising administering to the subject in need thereof a therapeutically effective amount of a compound or pharmaceutical composition disclosed herein.

Also disclosed herein is a method for diminishing allergen-induced airway remodeling in a subject, comprising administering to the subject in need thereof a therapeutically effective amount of a compound or pharmaceutical composition disclosed herein.

Further disclosed herein is a method for diminishing hypoxia-induced remodeling of the pulmonary vasculature in a subject, comprising administering to the subject in need thereof a therapeutically effective amount of a compound or pharmaceutical composition disclosed herein.

The foregoing will become more apparent from the following detailed description, which proceeds with reference to the accompanying figures.

BRIEF DESCRIPTION OF THE DRAWINGS

Figures 1A, 1B, 2, 3, 4:
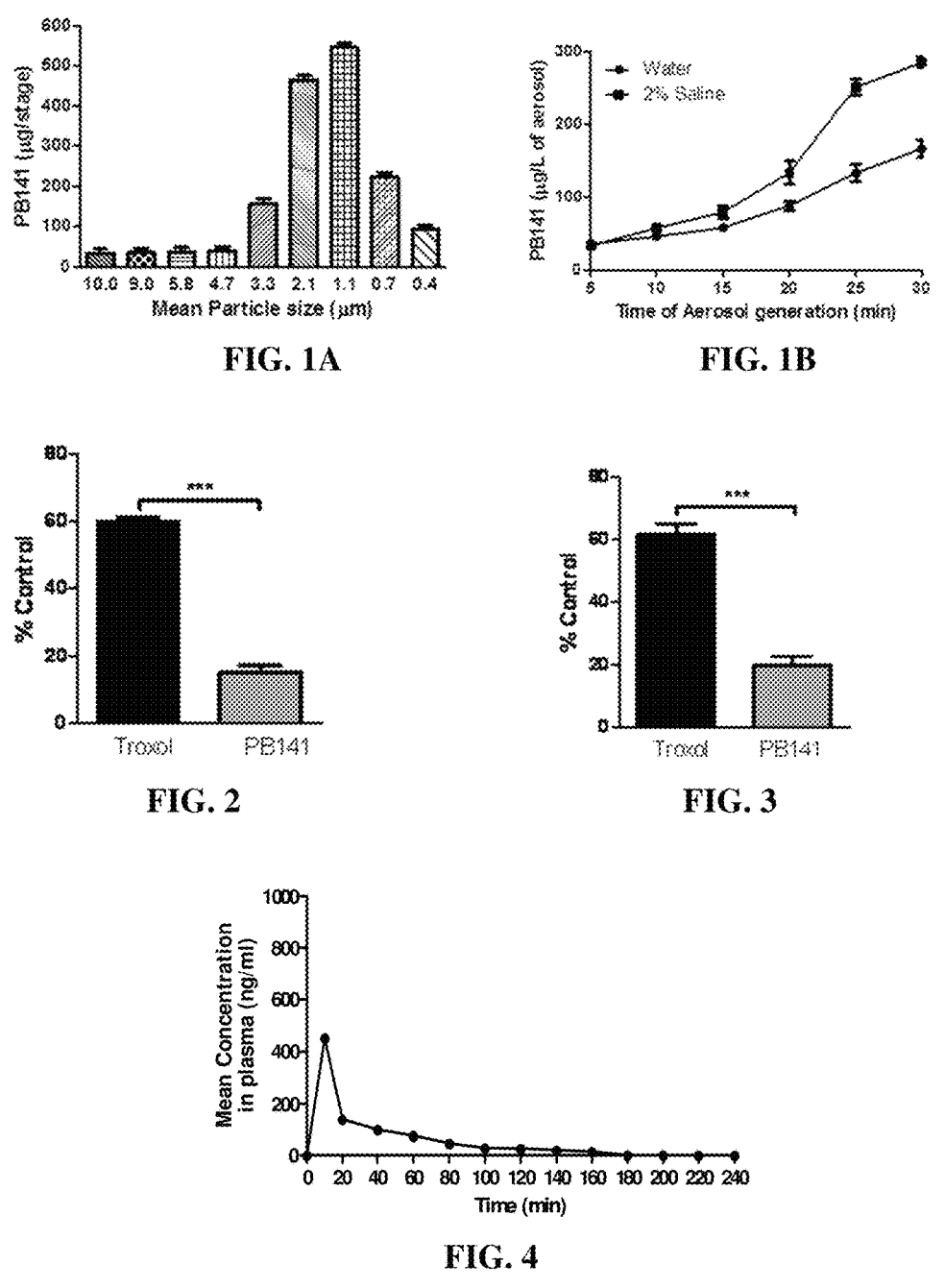

FIGS. 1A-1B demonstrate nebulization of PB141. PB141 was dissolved in water or different concentrations of PBS and the solutions were aerosolized using a micropump nebulizer (Buxco Research Systems, Wilmington, N.C.) flowing at 10 L of air/min. Aerosol droplet size was measured with an Andersen cascade impactor. (FIG. 1A) Distribution of PB141 aerosol droplet sizes. (FIG. 1B) The concentration of PB141 during a 30 min nebulization period was measured by collecting samples during nebulization and analyzing by spectrophotometer in two independent experiments.

FIG. 2 shows that PB141 exhibits anti-oxidant activities. The anti-oxidant activities of PB 141 were determined by the ability of this compound to react with pre-formed radical monocation of 2, 2'-azinobis-(3-ethylbenzothiazoline)-6-sulfonic acid (ABTS$^+$). Data are representative of one of two independent experiments; n=3; ***$P<0.001$ versus Troxol.

FIG. 3 shows that PB141 exhibits anti-oxidant activities. The antioxidant activity of PB141 was determined by ferric reduction/anti-oxidant power (FRAP) assay in which the compound is reacted with ferric tripyridyltriazine complex. Data are representative of one of two independent experiments; n=3; ***$P<0.001$ versus Troxol.

FIG. 4 shows that PB141 is rapidly cleared from the systemic circulation. After pulmonary delivery of PB141 for 7 days, blood was collected at intervals from the retro-orbital plexus and plasma separated. Plasma PB141 was determined by isocratic HPLC.

(FIG. 5A) Lungs were excised, sectioned, and examined histologically for evidence of inflammation or injury. (FIG. 5B) Potential kidney and liver injury were assessed by serum levels of creatinine, AST, and ALT. (FIG. 5C) Shows that nebulized PB141 inhibits LPS-induced upregulation of NF-κB in a concentration-dependent manner. Acute lung injury was induced in mice by intratracheal administration of LPS. Thirty min later PBS or varying concentrations of PB141 were delivered into cage air by nebulization. Following sacrifice, nuclear proteins were isolated from lungs and used to determine DNA-binding activity of the p65 subunit of the pro-inflammatory transcription factor NF-κB.

FIGS. 6A-6C show that PB141 treatment in vitro upregulates Nrf2 and inhibits NF-κB activity. BEAS-2B cells were treated with varying concentrations of PB141 for 24 h, after which (FIG. 6A) Nrf2 activity was measured or (FIG. 6C) nuclear Nrf2 concentration was determined by Western blotting. (FIG. 6B) In other experiments cells were pretreated with varying concentrations of PB141 for 1 h, then with LPS (500 ng/ml) for 6 h. Cells were then isolated and activity of NF-κB was measured.

FIG. 7 shows that PB141 inhibits lung fibroblast proliferation. IMR-90 cells were cultured in Dulbecco's modified Eagle's medium (DMEM) containing 10% heat-inactivated fetal bovine serum, penicillin, and streptomycin (100 IU/ml). Monolayer cultures were deprived of serum for 24 h, and treated with different concentrations of PB141 for different time periods as indicated. Cell numbers were then counted at 24, 48, and 72 h. Data are representative of one of two independent experiments; n=3.

(FIG. 8A) Western blot analysis for α-smooth muscle actin. (FIG. 8B) Quantitative values for each condition. ***P<0.001 vs Veh. (FIG. 8C) Immunofluorescence microscopy for α-SMA following treatment. Blots and images are representative of two independent experiments.

(FIG. 9A) Lung hydroxyproline content. (FIG. 9B) Lung fibrinolysis. (FIG. 9C) Lung collagen content. (FIG. 9D) Lung TGF-β content. Data are representative of one of two independent experiments with n=5-7 mice per group; p<0.01, *p<0.001.

FIGS. 10A-10L show that nebulized PB141 reduces LPS-induced lung inflammation and oxidative damage. Induction of ALI by intratracheal injection of LPS (50 μg) was followed 30 min later by nebulization of PB141 (25 mg/kg) or vehicle (saline) and delivery to cage air via a micropump nebulizer. After a further 5.5 h, BAL fluid, plasma, and lung samples were obtained. (FIG. 10A) Total cell and (FIG. 10B) neutrophil number in BAL fluid; myeloperoxidase activity in (FIG. 10C) lung tissue and (FIG. 10D) BAL fluid; (FIG. 10E) microscopic examination following staining of BAL fluid; (FIG. 10F) $H_2O_2$ production; (FIG. 10G) nitrate concentration, and (FIG. 10H) malonyldialdehyde/protein ratio in lung. Plasma levels of (FIG. 10I) MIP-2, (FIG. 10J) IL-6, (FIG. 10K) TNF-α, and (FIG. 10L) KC. Data are representative of one of two independent experiments with n=5-8 mice per group; ***p<0.001.

(FIG. 11A) Protein concentration in BAL fluid. (FIG. 11B) Ratio of lung wet:dry weight. (FIG. 11C) Histological examination of the lung following H&E staining Data are representative of one of two independent experiments with n=5-8 mice per group; ***p<0.001.

(FIG. 14B) Histology showing lung tumor incidence and burden. Data are representative of one of two independent experiments with n=9-11 mice per group.

(FIG. 15A) Airway resistance. (FIG. 15B) Airway elastance. Data are representative of one of two independent experiments with n=6-8 mice per group.

(FIG. 16A) Total and differential cell count in BAL fluid. (FIG. 16B) Microscopic examination following staining of BAL fluid. (FIG. 16C) $H_2O_2$ production, (FIG. 16D) Protein concentration in BAL fluid. Data are representative of one of two independent experiments with n=7-10 mice per group; ***p<0.001.

DETAILED DESCRIPTION

Terminology

Figure 5A:
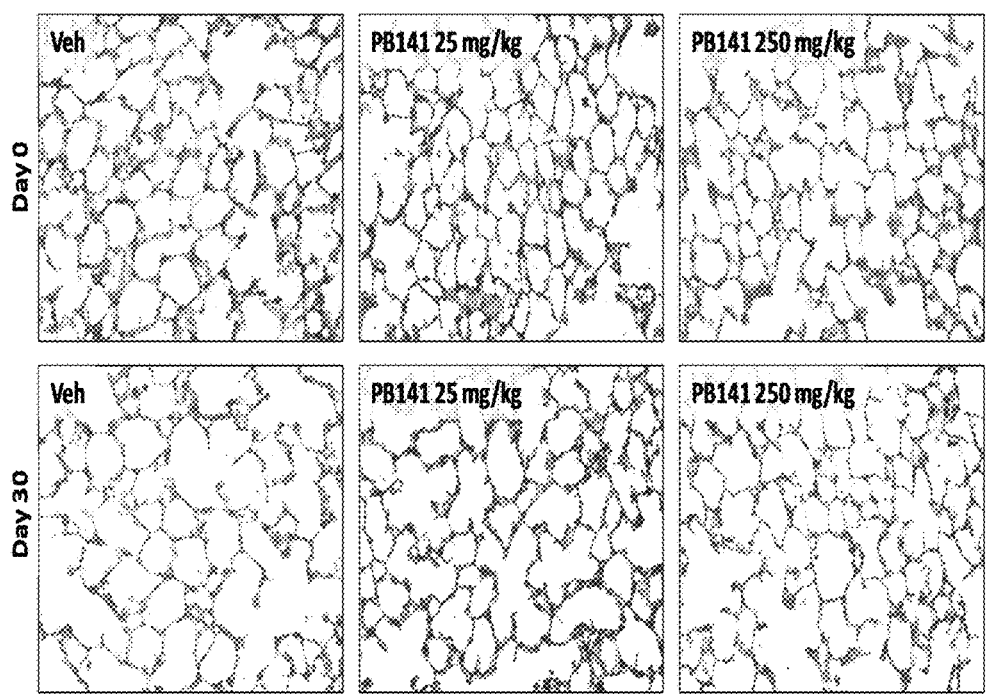
FIGS. 5A-5C demonstrate absence of kidney, liver or lung toxicity following long-term, high-dose pulmonary delivery of PB141. PB141 was delivered to mice by nebulization at doses of 25 or 250 mg/kg for up to 30 days.
Figure 5B:
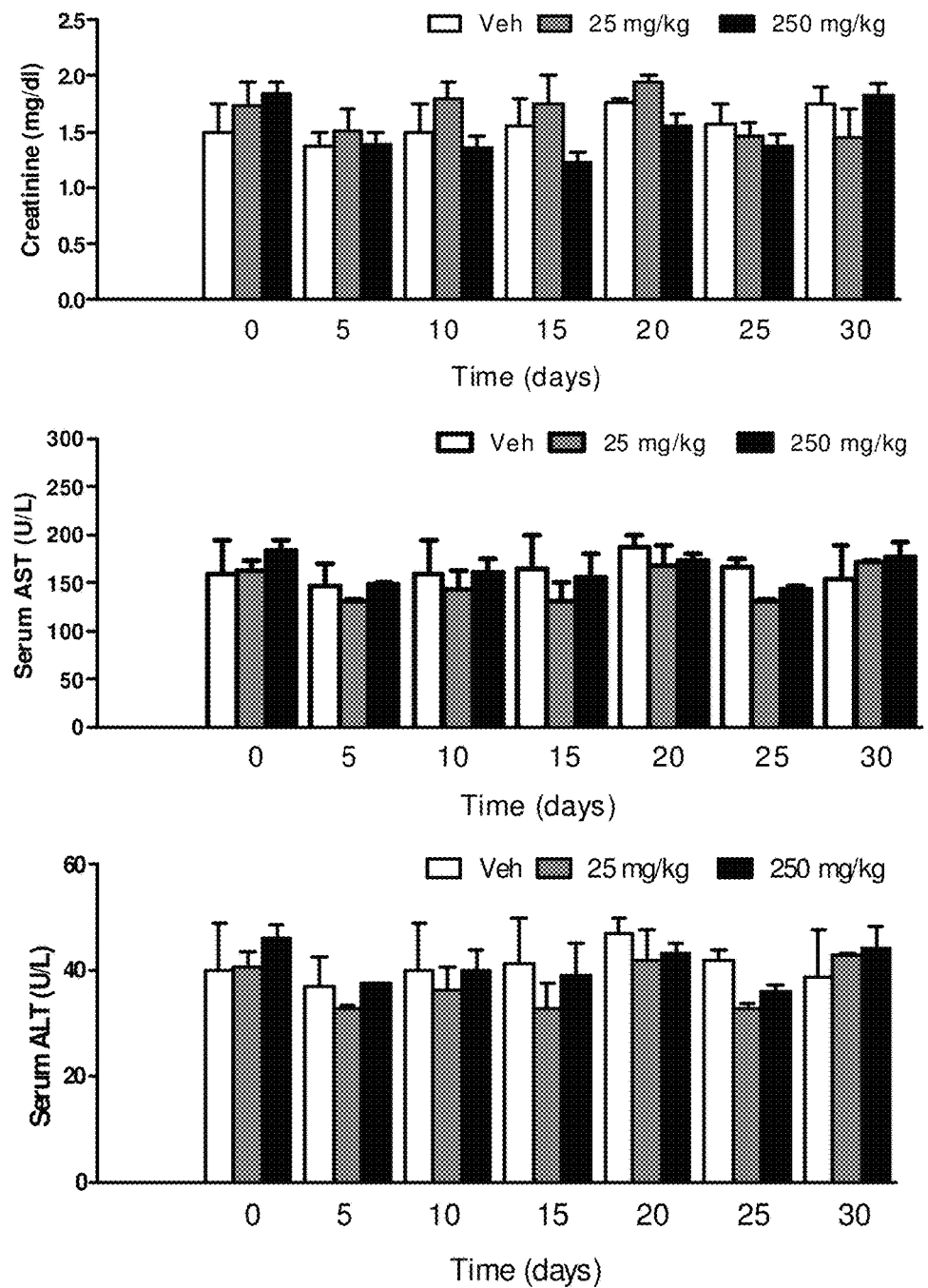
Figure 5C:
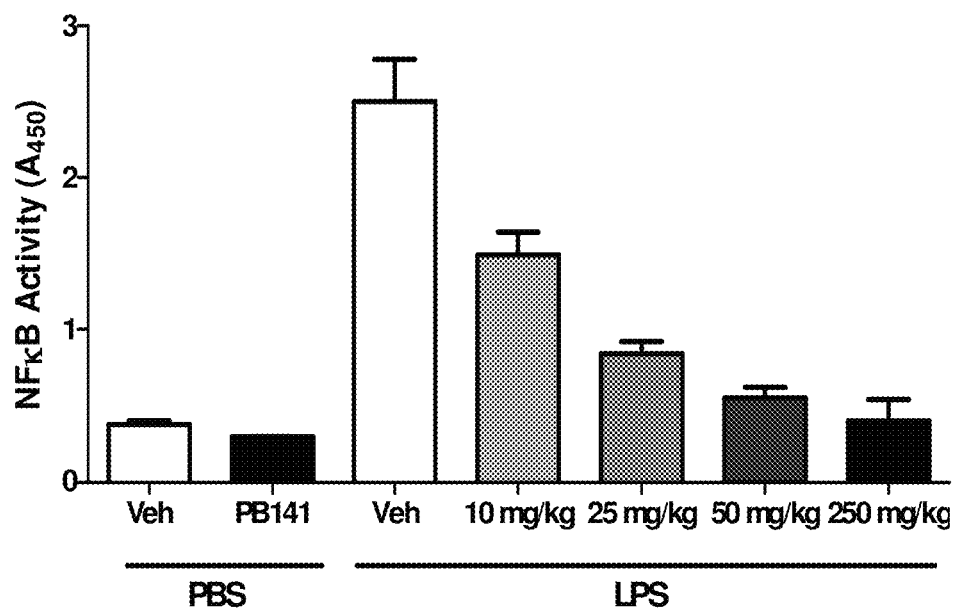

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms. Acetyl is an example of an acyl.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, acyl or heterocycloalkyl group. For example, an "alkylamino" or "alkylated amino" refers to —NRR', wherein at least one of R or R' is an alkyl. An "acylamino" refers to —N(R)—C(O)—R (wherein R is a substituted group such as alkyl or H). A suitable acylamino group is acetamido.

The term "aminoalkyl" refers to alkyl groups as defined above where at least one hydrogen atom is replaced with an amino group (e.g, —CH$_2$—NH$_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An illustrative aminocarbonyl is —CONH$_2$. The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

The term "carboxylate" or "carboxyl" refers to the group —COO$^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

"Carboxylalkyl" refers to an alkyl wherein one or more hydrogens of the alkyl is substituted with a carboxyl group (e.g., —RCOOH).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen hetero atom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The N-heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$ alkenyl, $C_{2-6}$ alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl.

"Sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —$SO_2H$.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

The term "sulfonylamido" or "sulfonamide" refers to the group —$SO_2NH_2$.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial toxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and alkaline earth metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, Drug Metabolism Reviews 165 (1988) and Bundgaard, Design of Prodrugs, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

The usefulness of diaryl enone compounds is impeded by limited water solubility. This drawback is especially relevant to treatment of lung disease, since inhalation of a nebulized formulation is the preferred method for delivery of therapeutic agents to the lung. Delivery of a drug by inhalation allows deposition of the drug into different sections of the respiratory tract, including the throat, trachea, bronchi and alveoli. Generally, the smaller the size of the inhaled particle the longer it will remain suspended in air and the farther down the respiratory tract the inhaled drug can be delivered. The desired properties of a liquid for nebulization generally include: 1) low viscosity; 2) sterile medium; 3) low surface tension; 4) stability toward the mechanism of nebulization; 5) moderate pH (about 4-10); 6) ability to form droplets; 7) absence of irritating preservatives and stabilizing agents; and 8) suitable tonicity. A wide variety of nebulizers differing in mode of operation are available. These include ultrasonic, vibrating membrane, vibrating mesh, vibrating plate, vibrating cone, micropump, and jet nebulizers along with others. The vibrating mesh, vibrating cone or vibrating plate nebulizers are of particular interest since they do not require the use of an air compressor for delivery, have a minimal residual volume in the reservoir after delivery of a unit dose, and can be used to deliver low volumes of inhalable solutions. The principle advantages of nebulizers over other methods of pulmonary installation are that patient cooperation is not required and it is easier to deliver high doses of medication.

As many thiol-containing compounds are highly hydrophilic, they may form water-soluble adducts with diaryl enone compounds. The resulting water-soluble compounds could then not only be incorporated into nebulizable formulations for delivery to the lung by inhalation but may freely enter cells, where the diaryl enone component could exert therapeutic effects either by forming adducts with cysteine residues, accompanied by displacement of the original thiol residue, or by other means. Based on these considerations, disclosed herein are novel thiol derivatives of specific, novel, diaryl enones. Also disclosed are formulations of these compounds suitable for pulmonary delivery and their use for treating pulmonary disease.

Disclosed herein in certain embodiments are novel diaryl enone compounds that possess anti-inflammatory, antioxidant, and other therapeutic properties. Also described are nebulized aerosol or dry powder formulations of these compounds that are suitable for delivery to the pulmonary system by inhalation. Further described are uses of these compounds and formulations for treatment of various pulmonary diseases. The therapeutically useful compounds may be rendered water-soluble, for example, though formation of suitable thiol derivatives.

In one aspect, the novel compounds may be produced by chemically combining a diaryl enone compound with a thiol that renders the final compound water-soluble. Such water-soluble compounds can readily enter cells, where the synthetically added thiols may be displaced by intracellular thiols such as the cysteine residues in various proteins. The aryl groups are composed of unique di- or tri-nitrogen containing moieties, in which the inductive effects of the nitrogen atoms induce a partially positive charge on the carbon atoms. Because of the low-lying unoccupied n-molecular orbitals in these nitrogen-containing compounds, and their derivatives, these compounds demonstrate unique physico-chemical properties and the ability to act as a bridging ligand.

Compounds

Disclosed herein are compounds, or a pharmaceutically acceptable salt or ester thereof, comprising an adduct of a hydrophilic thiol and an enone that comprises at least two N-heterocycles.

For example, one embodiment is a compound, or a pharmaceutically acceptable salt or ester thereof, having a structure of:

$X^1$-L-$X^2$ wherein L is a linking moiety comprising an enone; and
$X^1$ and $X^2$ are each independently an optionally-substituted N-heterocycle.

L, for example, may be an alkyl-1,4-diene-3-one such as penta-1,4-dien-3-one, or an alkyl-1,5-thiol-3-one such as penta-1,5-thiol-3-one, wherein each thiol is optionally substituted. Other substituted alkyl dienes with each double bond adjacent to a ketone are equally suitable, as are aryl ketones with thiol groups positioned between tow carbons from the ketone.

In certain embodiments, $X^1$ and $X^2$ are the same, and are each, for example, pyrazinyl or pyrimidinyl.

In a further embodiment, there is disclosed is a compound, or a pharmaceutically acceptable salt or ester thereof, having a structure of:

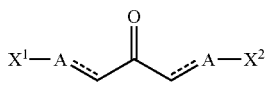

(Formula I)

wherein ══ represents a single bond or a double bond;

A is CH if ══ is a double bond, or CH(S—$R^5$) if ══ is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl; and $X^1$ and $X^2$ are each independently an optionally-substituted N-heterocycle; or

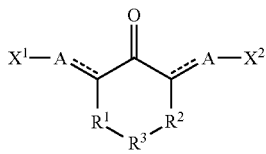

(Formula II)

wherein ══ represents a single bond or a double bond;

A is CH if ══ is a double bond, or CH(S—$R^5$) if ══ is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;

$X^1$ and $X^2$ are each independently an optionally-substituted N-heterocycle; and $R^1$, $R^2$, and $R^3$ are each independently C or N; or

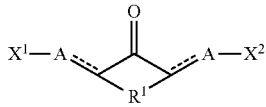

(Formula III)

wherein ══ represents a single bond or a double bond;

A is CH if ══ is a double bond, or CH(S—$R^5$) if ══ is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;

$X^1$ and $X^2$ are each independently an optionally-substituted N-heterocycle; and $R^1$ is C or N; or

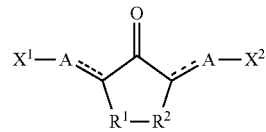

(Formula IV)

wherein ══ represents a single bond or a double bond;

A is CH if ══ is a double bond, or CH(S—$R^5$) if ══ is a single bond, wherein $R^5$ is a peptide, amino acid, amino acid derivative, optionally-substituted alkyl, optionally-substituted alkenyl, optionally-substituted alkynyl, optionally-substituted cycloalkyl, or optionally-substituted cycloalkenyl;

$R^1$ and $R^2$ are each independently C or N; and $X^1$ and $X^2$ are each independently an optionally-substituted N-heterocycle.

In the compound described above, $X^1$ may have a structure of:

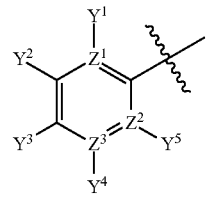

and $X^2$ has a structure of:

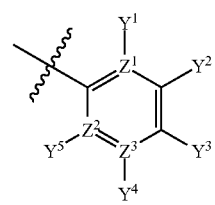

wherein $Z^1$, $Z^2$, and $Z^3$ are each independently C or N, provided that at least one of $Z^1$, $Z^2$, or $Z^3$ is N; and $Y^1$, $Y^2$, $Y^3$, $Y^4$ and $Y^5$ are each independently H, optionally-substituted alkyl, optionally-substituted amino, hydroxyl, optionally-substituted alkoxy, optionally-substituted thiol, acyl, or halogen.

In certain embodiments, the compound has a structure of:

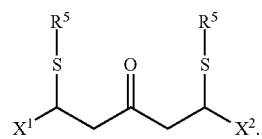

In certain embodiments, the compound has a structure of:

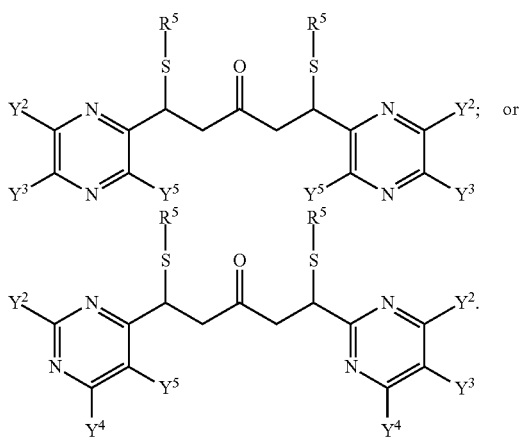

In certain embodiments, the compound has a structure of:

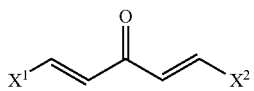

In certain embodiments, the compound has a structure of:

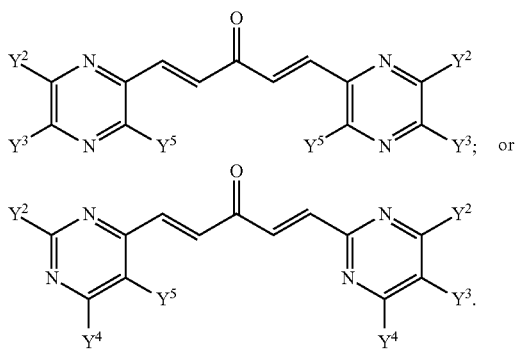

In certain embodiments, $X^1$ and $X^2$ are each optionally-substituted pyrazinyl or optionally-substituted pyrimidinyl.

In certain embodiments, $R^5$ is an acylamino-substituted carboxylalkyl, a sulfonate-substituted alkyl, or an acylamino-substituted amido. In certain embodiments, $R^5$ is a sugar derivative.

In certain embodiments, the —S—$R^5$ moiety is a derivative of N-acetylcysteine, 2-mercaptoethane sulfonate, or glutathione.

Illustrative compounds are shown below:

PB137

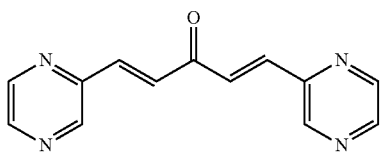

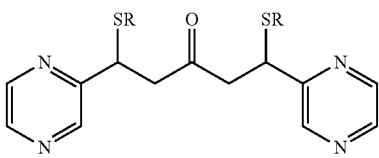

Thiol adduct of PB137, wherein —SR may be derived from N-acetylcysteine, 2-mercaptoethane sulfonate, glutathione, or another suitable thiol compound

PB141

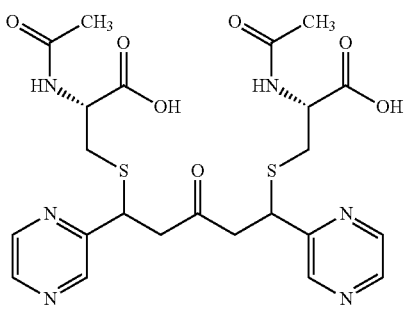

(NAC adduct of PB137)

PB142

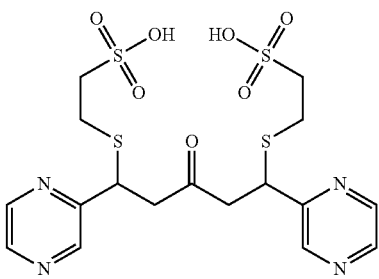

(mercaptoethane sulfonate adduct of PB137)

PB143

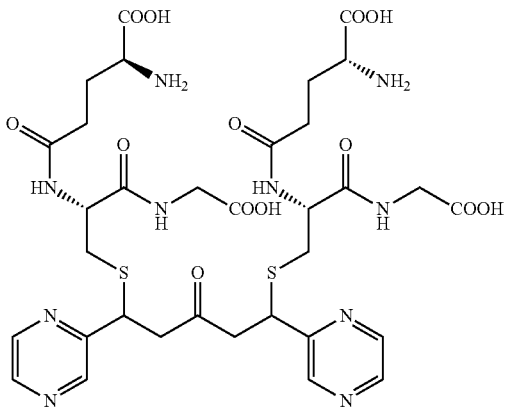

(glutathione adduct to PB137)

PB151

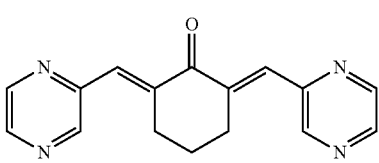

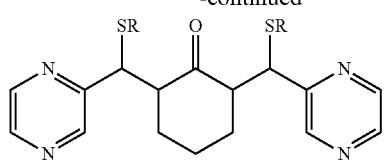
Thiol adduct of PB151, wherein —SR may be derived from N-acetylcysteine, 2-mercaptoethane sulfonate, glutathione, or another suitable thiol compound
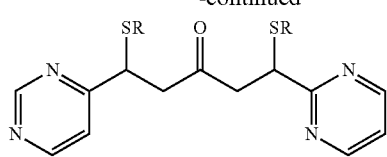
Thiol adduct of PB161, wherein —SR may be derived from N-acetylcysteine, 2-mercaptoethane sulfonate, glutathione, or another suitable thiol compound
PB157
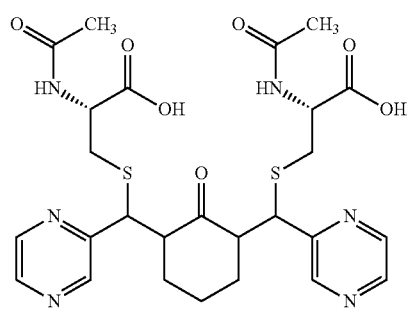
PB167
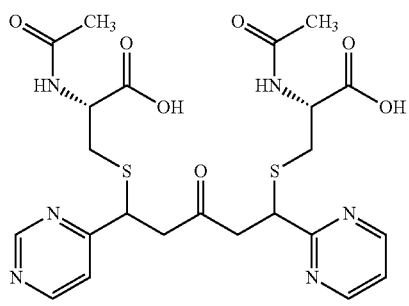
PB158
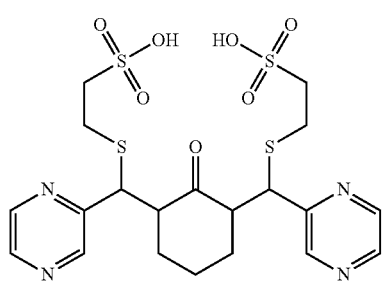
PB168
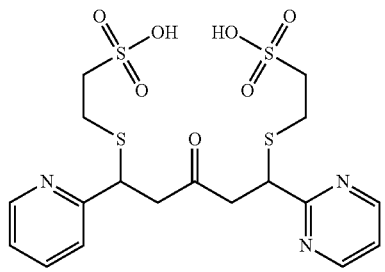
PB159
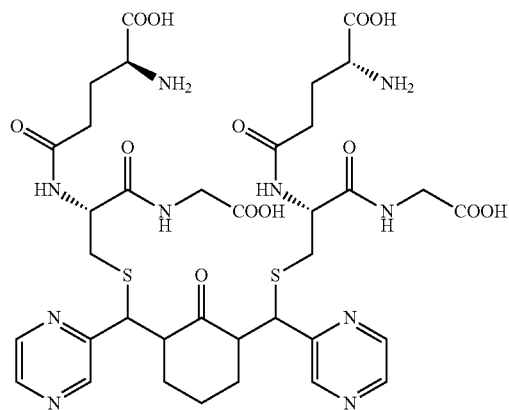
PB 169
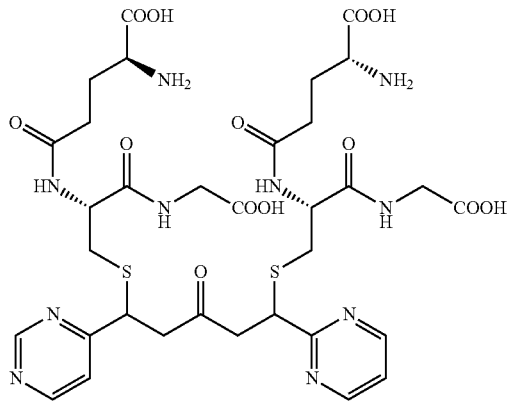
(glutathione adduct of PB 161)
PB161
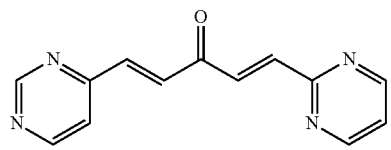
PB171

-continued

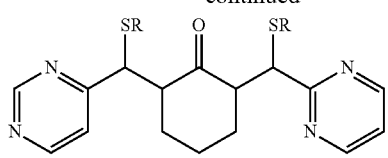

Thiol adduct of PB171, wherein —SR may be derived from N-acetylcysteine, 2-mercaptoethane sulfonate, glutathione, or another suitable thiol compound

PB177

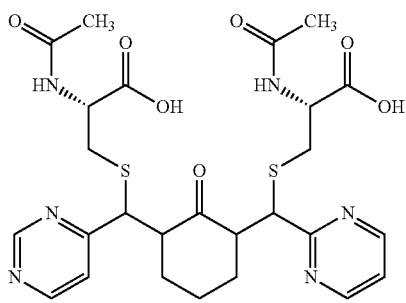

(NAC adduct of PB171)

PB178

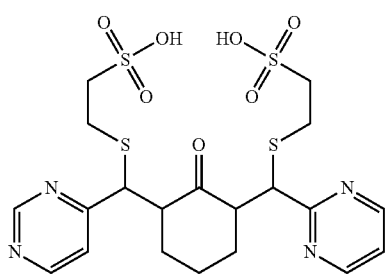

(mercaptoethanesulfonate adduct of PB171)

PB179

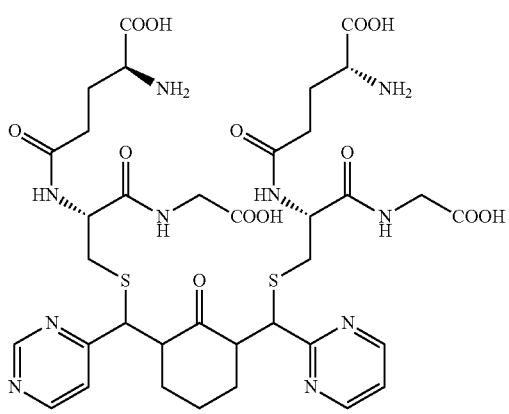

(glutathione adduct of PB171)

PB200

-continued

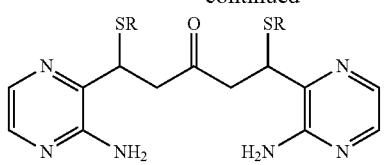

Thiol adducts of PB200, wherein —SR may be derived from N-acetylcysteine, 2-mercaptoethane sulfonate, glutathione, or another suitable thiol compound

PB201

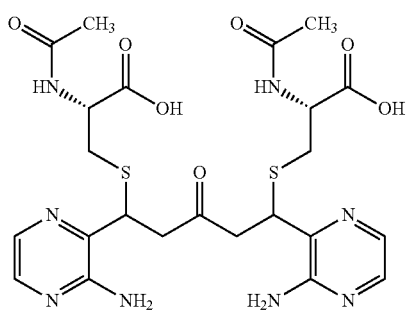

(NAC adduct of PB200)

PB202

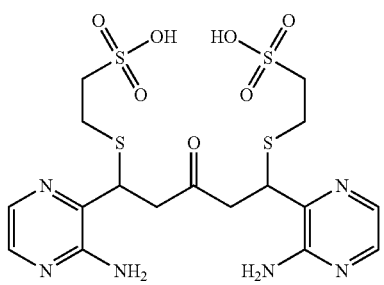

(mercaptoethanesufonate adduct of PB200)

PB203

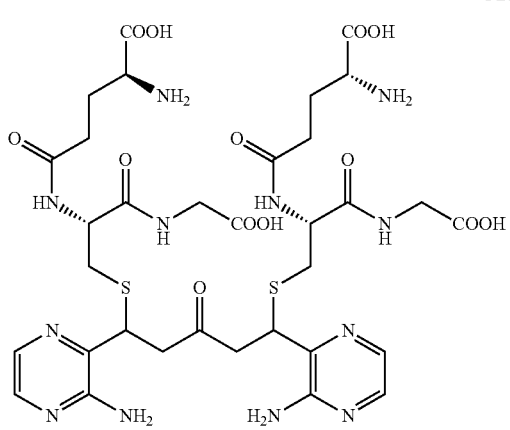

(glutathione adduct of PB200)

PB204

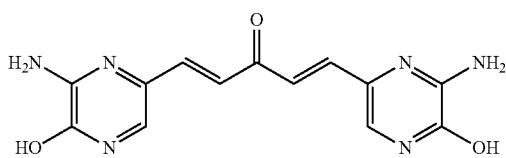

-continued

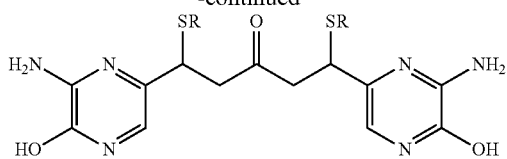

Thiol adduct of PB204, wherein —SR may be derived from N-acetylcysteine, 2-mercaptoethane sulfonate, glutathione, or another suitable thiol compound

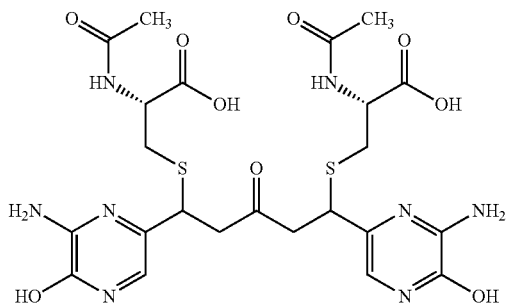

(NAC adduct of PB204)

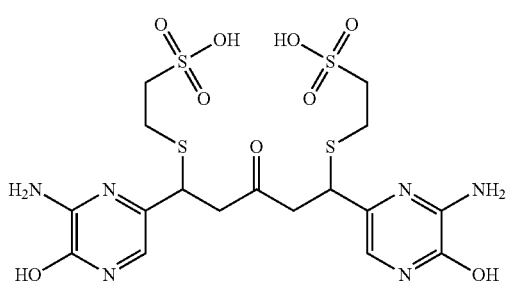

(mercaptoethanesulfonate adduct of PB 204)

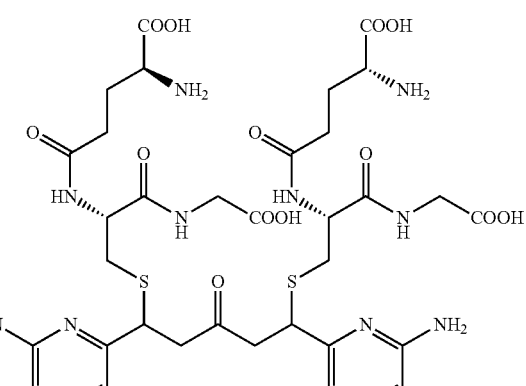

(glutathione adduct of PB204)

PB208

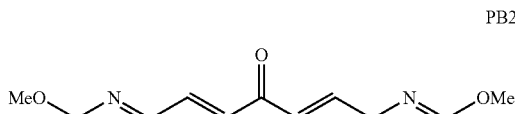

-continued

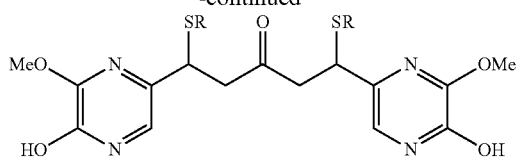

Thiol adduct of PB208, wherein —SR may be derived from N-acetylcysteine, 2-mercaptoethane sulfonate, glutathione, or another suitable thiol compound

PB205

PB209

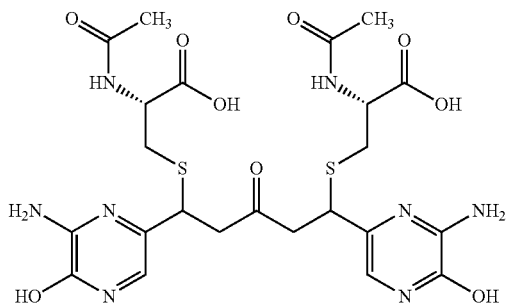

(NAC adduct of PB208)

PB206

PB210

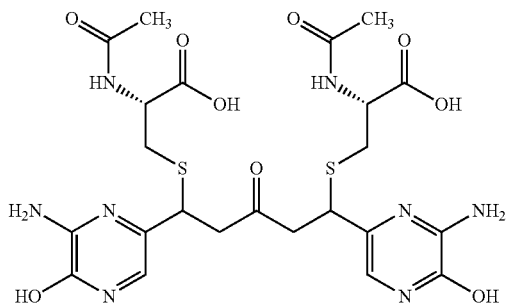

(mercaptoethanesulfonate adduct of PB208)

PB207

PB211

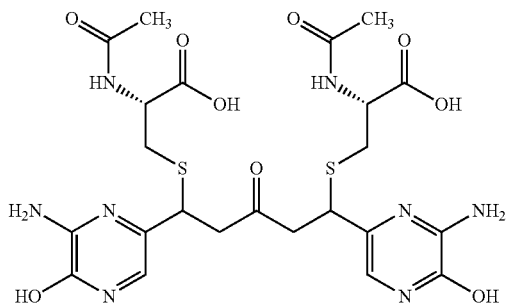

(glutathione adduct of PB208)

PB212

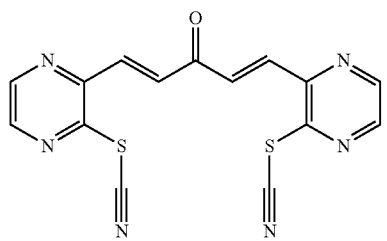

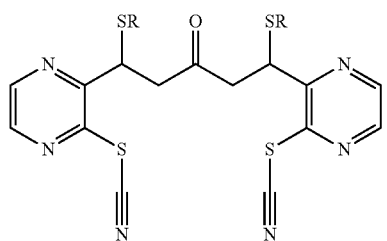

Thiol adduct of PB212, wherein —SR may be derived from N-acetylcysteine, 2-mercaptoethane sulfonate, glutathione, or another suitable thiol compound

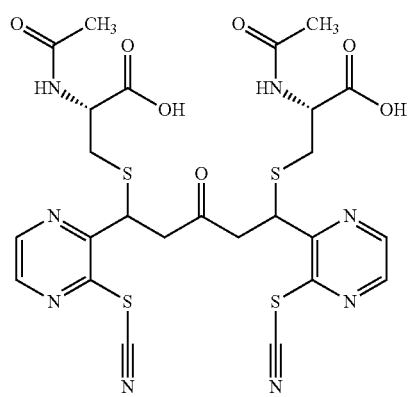

(NAC adduct of PB212)

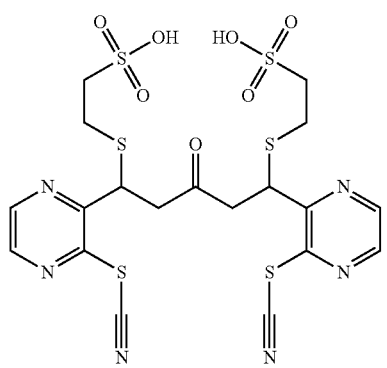

(mercaptoethanesulfonate adduct of PB212

PB215

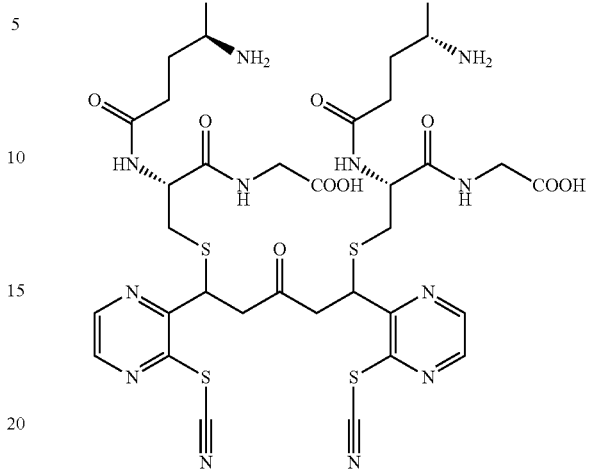

(glutathione adduct of PB212

PB213

PB216

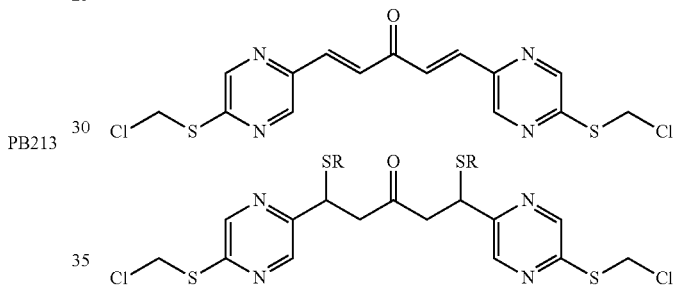

This adduct of PB216, wherein —SR may be dervived from N-acetylcysteine, 2-mercaptoethane sulfonate, glutathione, or another suitable thiol compound

PB217

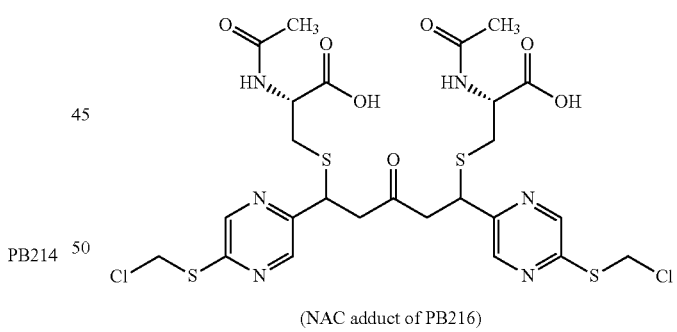

(NAC adduct of PB216)

PB214

PB218

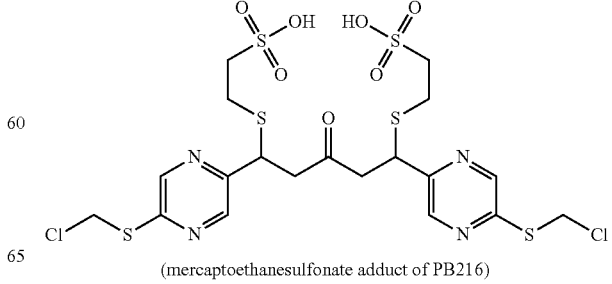

(mercaptoethanesulfonate adduct of PB216)

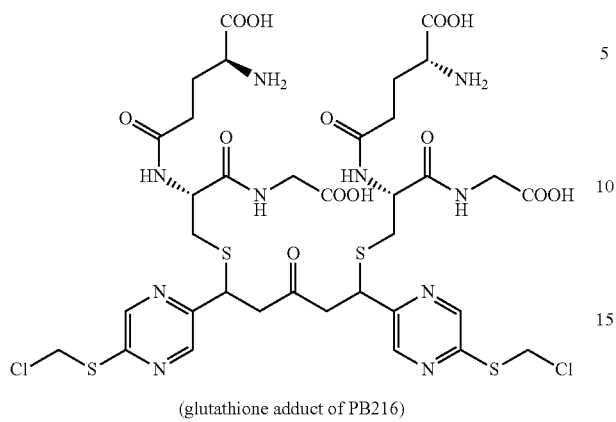
PB219
(glutathione adduct of PB216)

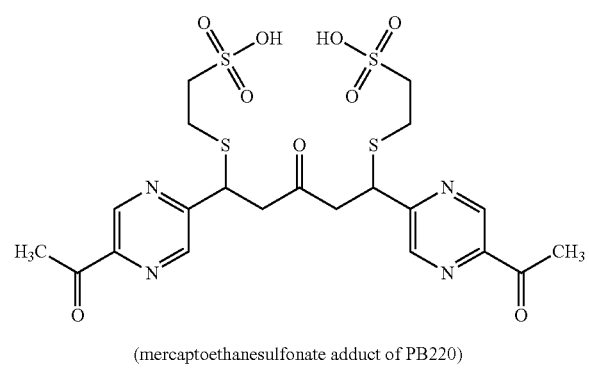
PB222
(mercaptoethanesulfonate adduct of PB220)

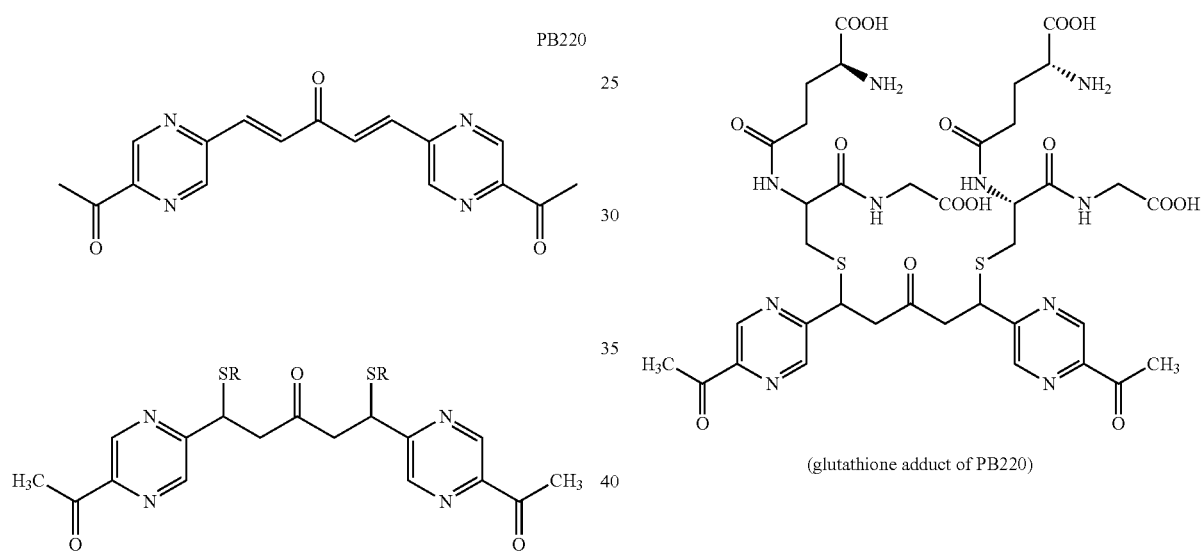

PB220

PB223
(glutathione adduct of PB220)

Thiol adduct of PB220, wherein —SR may be derived from N-acetylcysteine, 2-mercaptoethane sulfonate, glutathione, or another suitable thiol compound

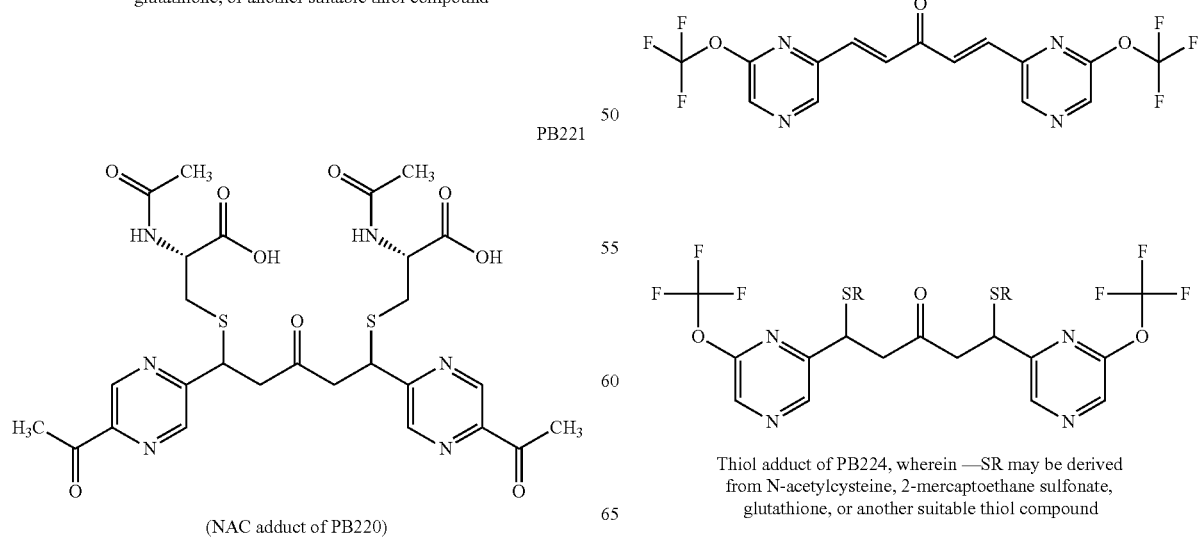

PB221
(NAC adduct of PB220)

PB224

Thiol adduct of PB224, wherein —SR may be derived from N-acetylcysteine, 2-mercaptoethane sulfonate, glutathione, or another suitable thiol compound

PB225

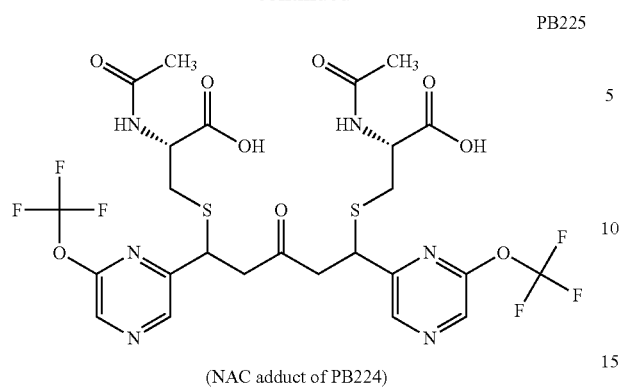

(NAC adduct of PB224)

PB229

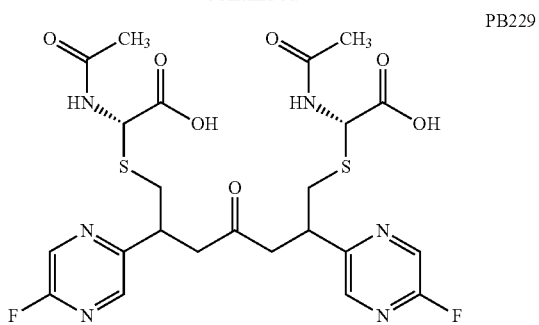

(NAC adduct of PB228)

PB226

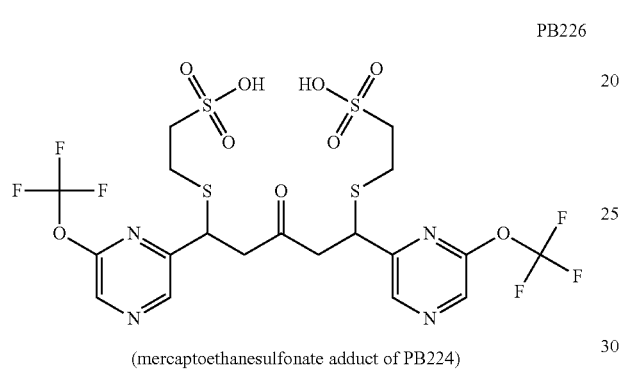

(mercaptoethanesulfonate adduct of PB224)

PB230

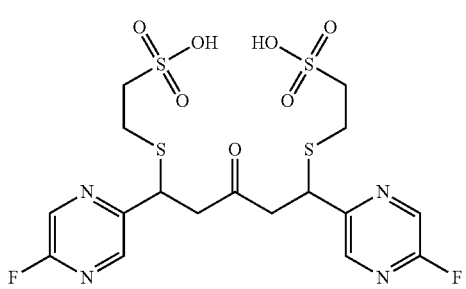

(mercaptoethanesulfonate adduct of PB228)

PB227

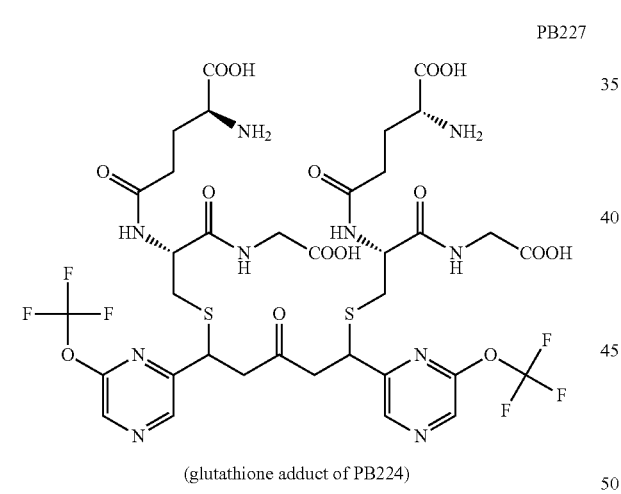

(glutathione adduct of PB224)

PB231

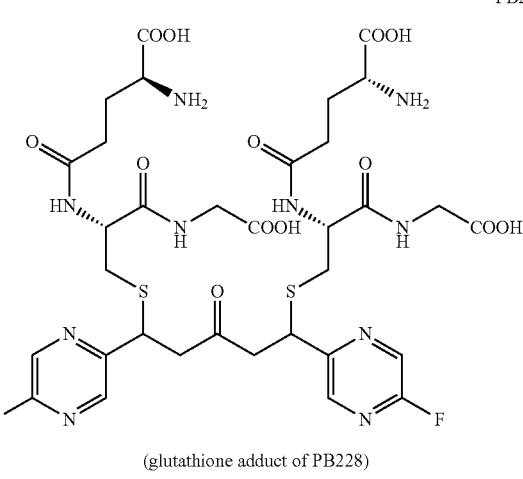

(glutathione adduct of PB228)

PB228

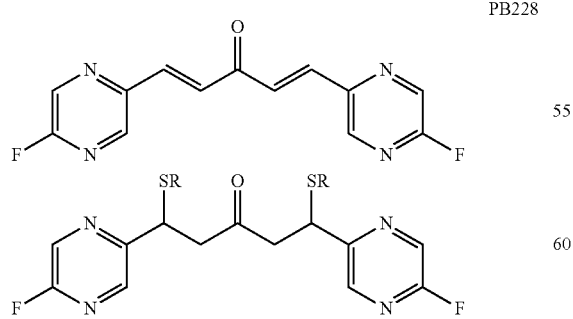

Thiol adduct of PB228, wherein —SR may be derived from N-acetylcysteine, 2-mercaptoethane sulfonate, glutathione, or another suitable thiol compound

PB232

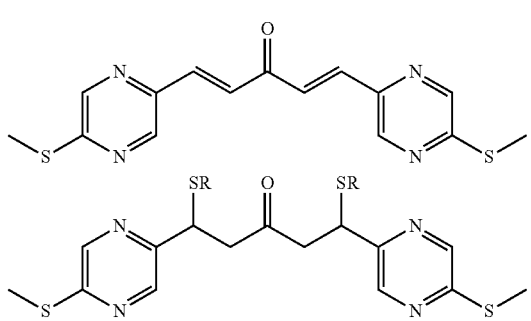

Thiol adduct of PB232, wherein —SR may be derived from N-acetylcysteine, 2-mercaptoethane sulfonate, glutathione, or another suitable thiol compound

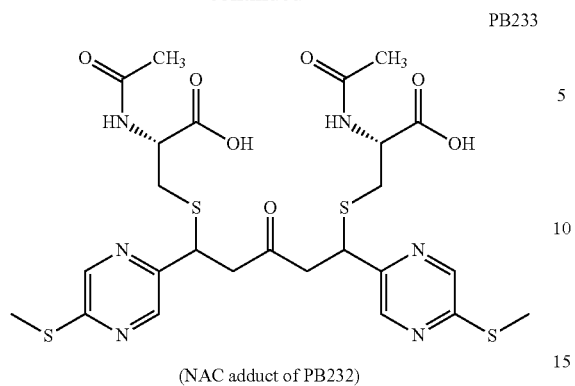

PB233

(NAC adduct of PB232)

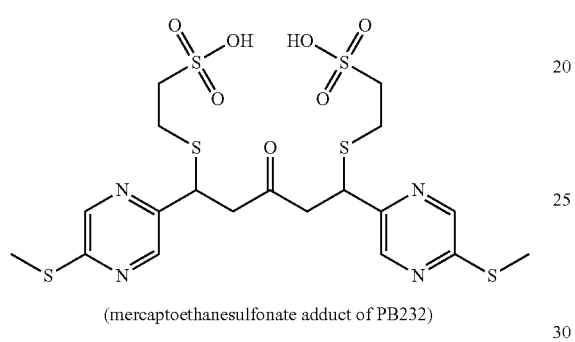

PB234

(mercaptoethanesulfonate adduct of PB232)

PB235

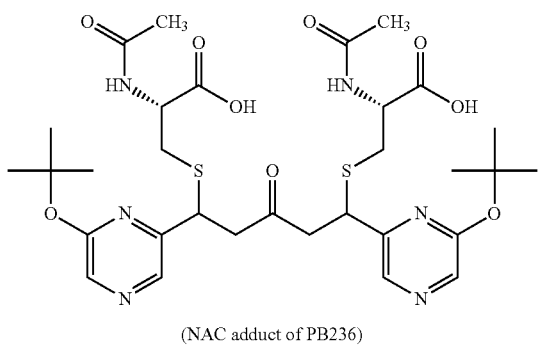

PB237

(NAC adduct of PB236)

PB238

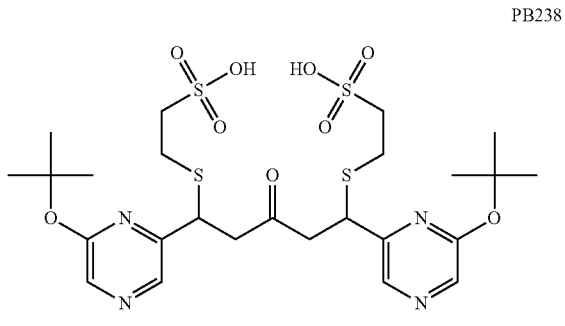

(mercaptoethanesulfonate adduct of PB236)

PB239

(glutathione adduct of PB 232)

PB236

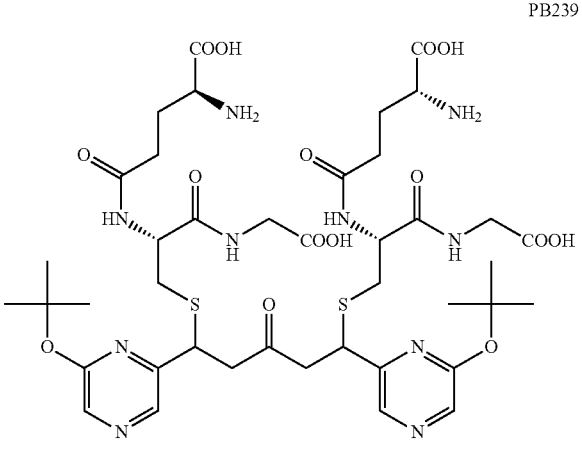

Thiol adduct of PB236, wherein —SR may be derived from N-acetylcysteine, 2-mercaptoethane sulfonate, glutathione, or another suitable thiol compound (glutathione adduct of PB236)

PB240

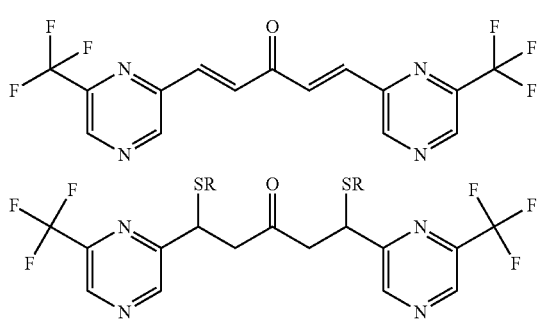

Thiol adduct of PB240, wherein —SR may be derived from N-acetylcysteine, 2-mercaptoethane sulfonate, glutathione, or another suitable thiol compound -continued

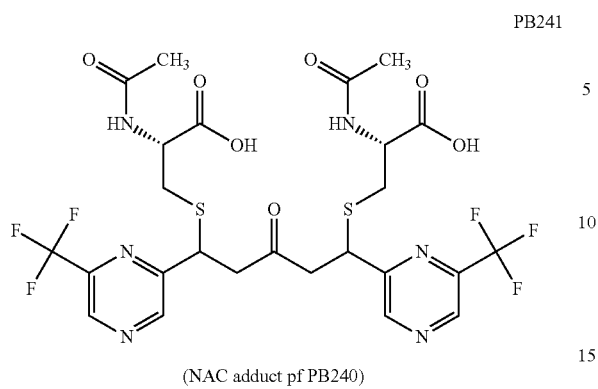

PB241

(NAC adduct pf PB240)

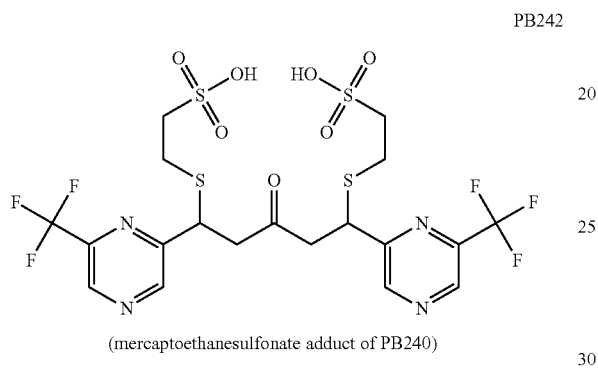

PB242

(mercaptoethanesulfonate adduct of PB240)

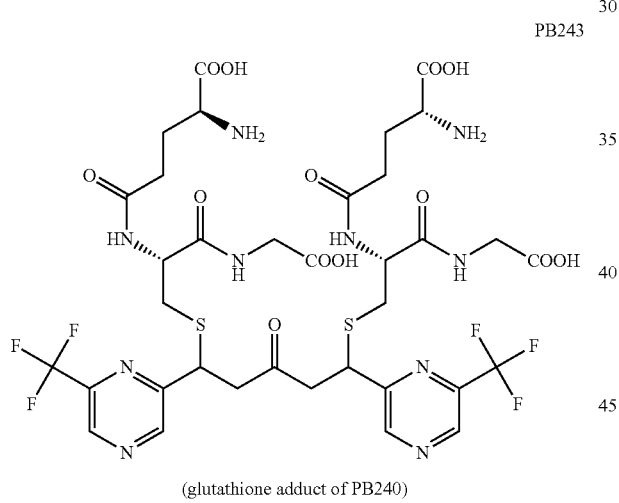

PB243

(glutathione adduct of PB240)

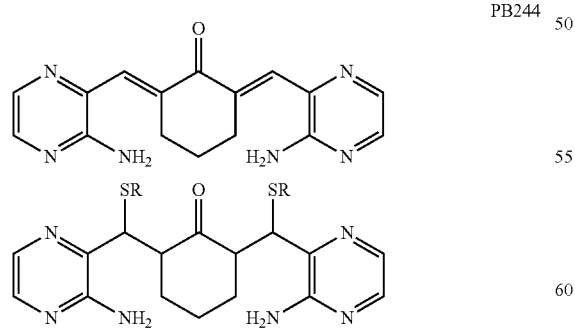

PB244

Thiol adduct of PB244, wherein —SR may be derived from N-acetylcysteine, 2-mercaptoethane sulfonate, glutathione, or another suitable thiol compound -continued

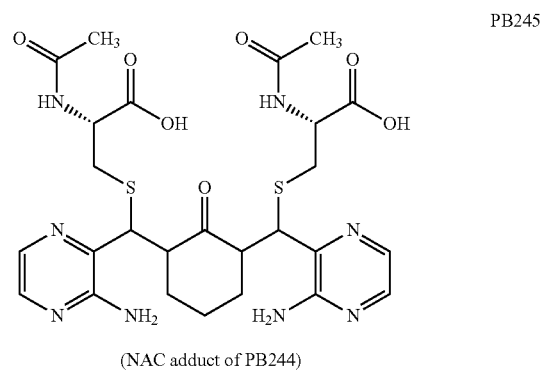

PB245

(NAC adduct of PB244)

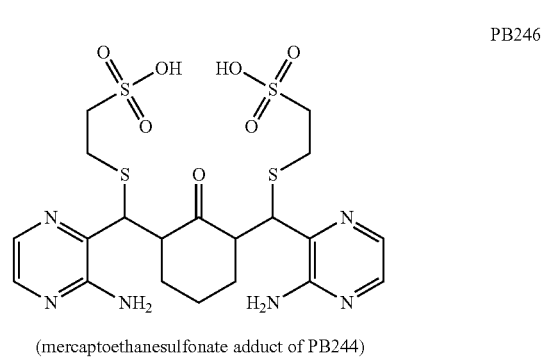

PB246

(mercaptoethanesulfonate adduct of PB244)

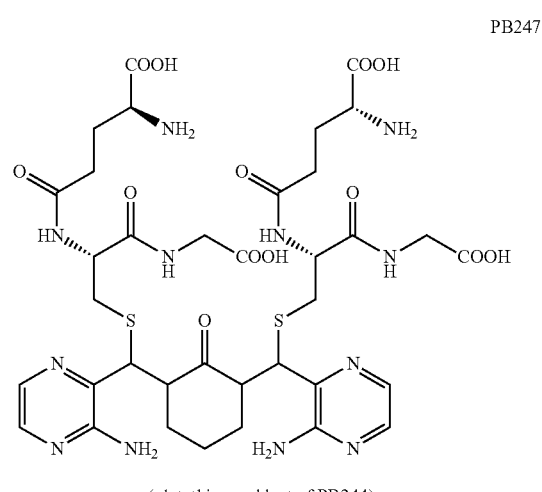

PB247

(glutathione adduct of PB244)

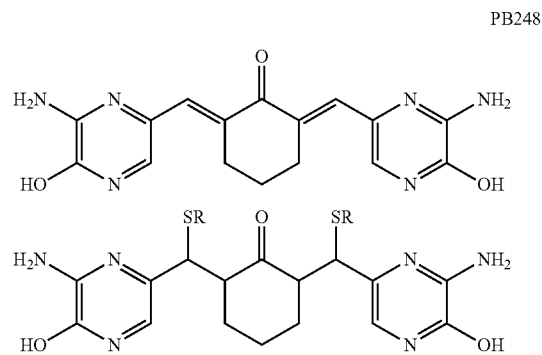

PB248

Thiol adduct of PB248, wherein —SR may be derived from N-acetylcysteine, 2-mercaptoethane sulfonate, glutathione, or another suitable thiol compound PB249
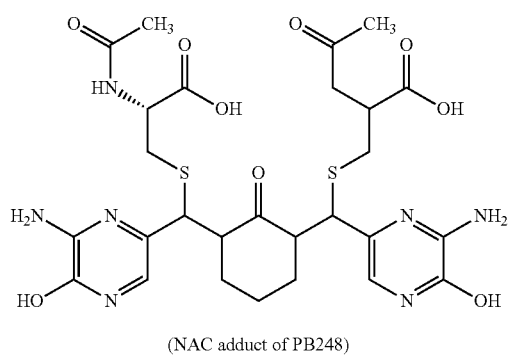
(NAC adduct of PB248)
PB250
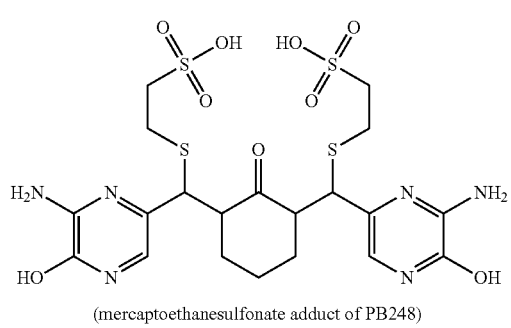
(mercaptoethanesulfonate adduct of PB248)
PB251
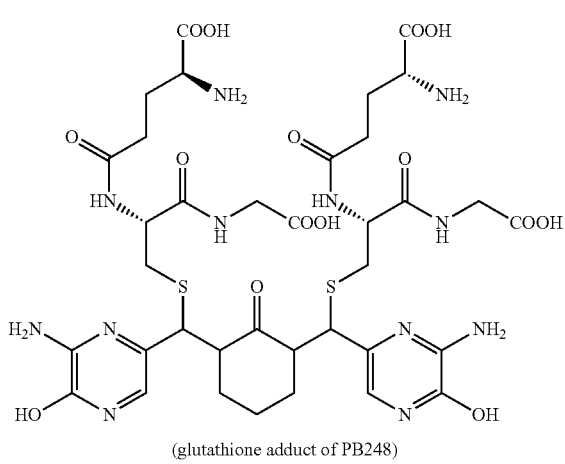
(glutathione adduct of PB248)
PB252
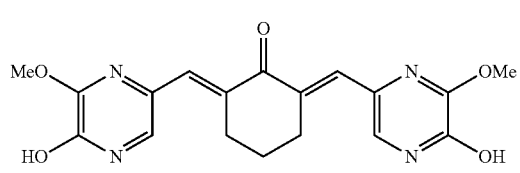
Thiol adduct of PB252, wherein —SR may be derived from N-acetylcysteine, 2-mercaptoethane sulfonate, glutathione, or another suitable thiol compound
PB253
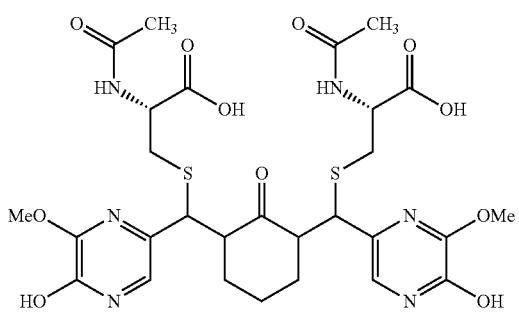
(NAC adduct of PB252)
PB254
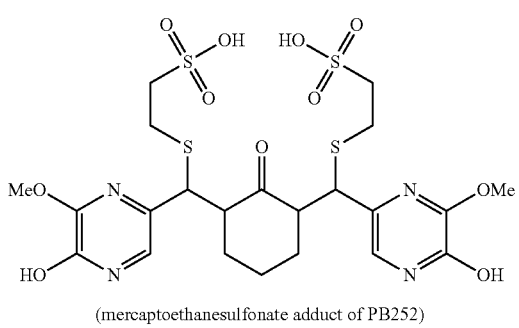
(mercaptoethanesulfonate adduct of PB252)
PB255
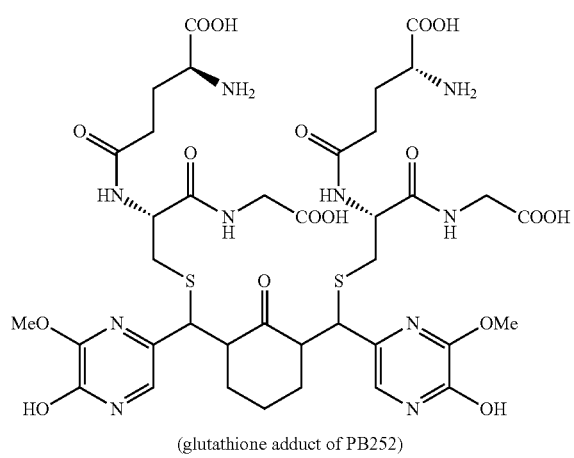
(glutathione adduct of PB252)
PB256
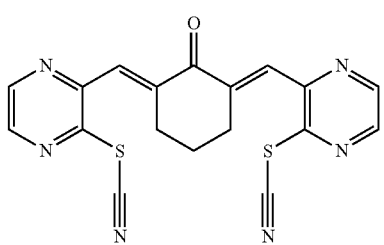

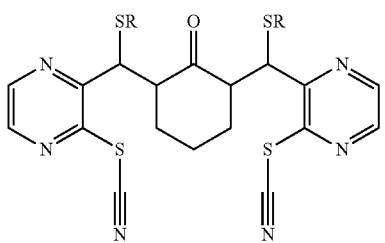

Thiol adduct of PB256, wherein —SR may be derived from N-acetylcysteine, 2-mercaptoethane sulfonate, glutathione, or another suitable thiol compound

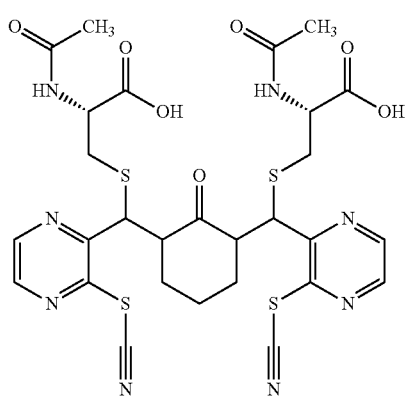

(NAC adduct of PB256)

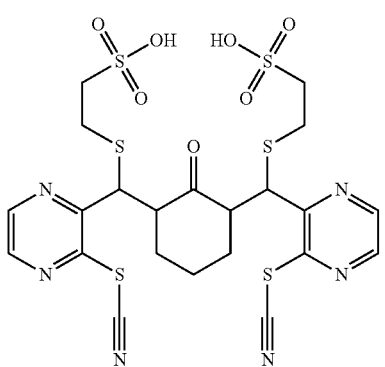

(mercaptoethanesulfonate adduct of PB256)

PB259

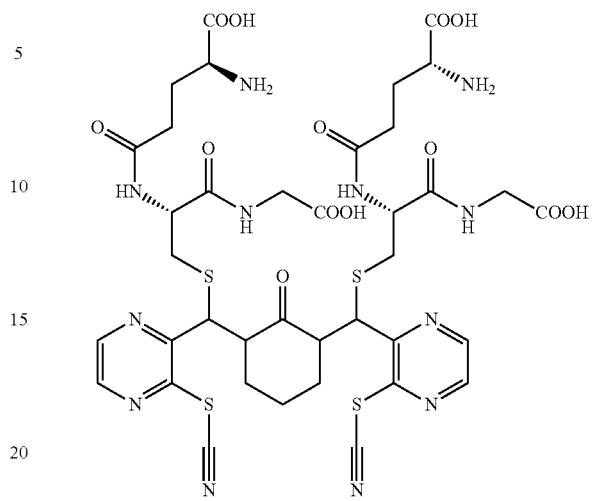

(glutathione adduct of PB256)

PB260

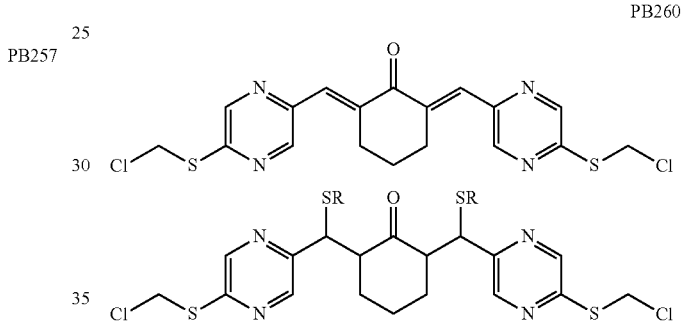

This adduct of PB260, wherein —SR may be derived from N-acetylcysteine, 2-mercaptoethane sulfonate, glutathione, or another suitable thiol compound

PB261

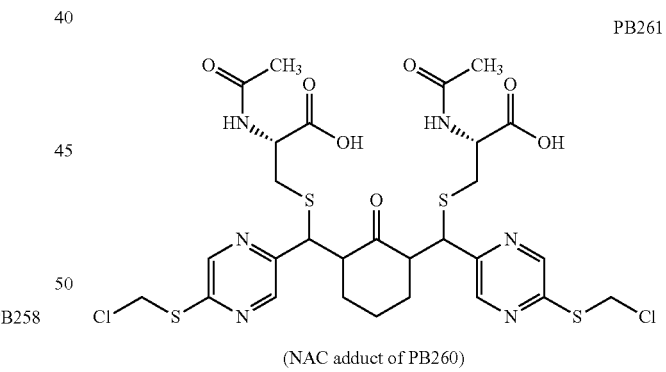

(NAC adduct of PB260)

PB262

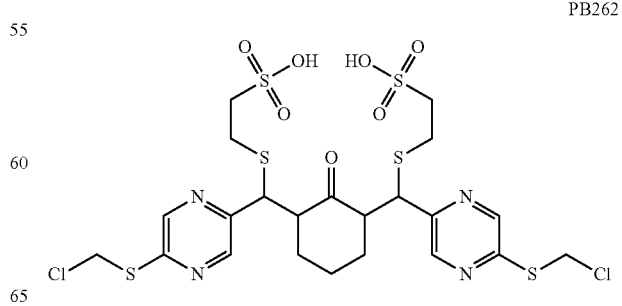

(mercaptoethanesulfonate adduct of PB260)

PB263

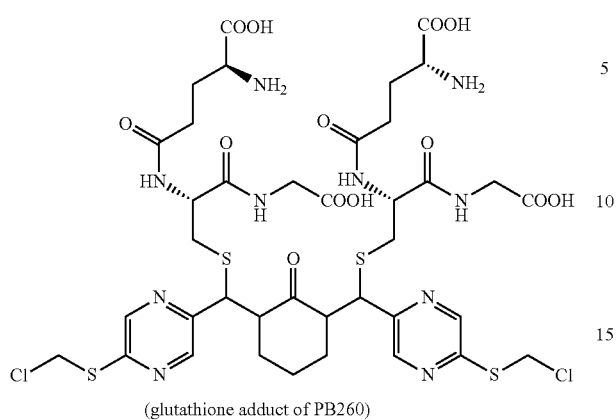
(glutathione adduct of PB260)

PB264

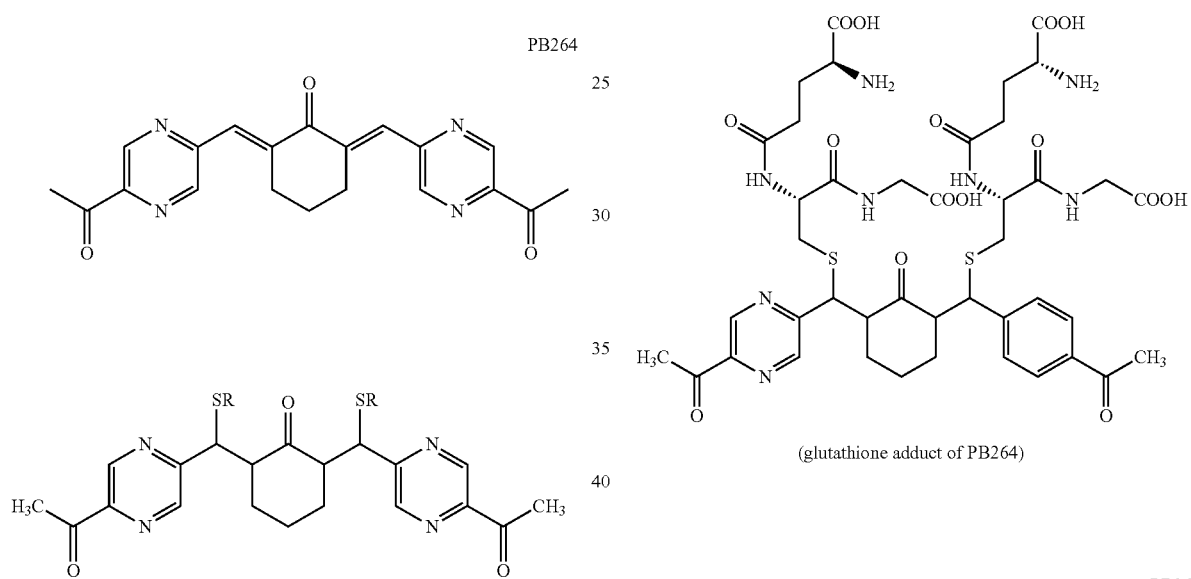

This adduct of PB264, wherein —SR may be derived from N-acetylcysteine, 2-mercaptoethanesulfonate sulfonate, glutahione, or another suitable thiol compound

PB265

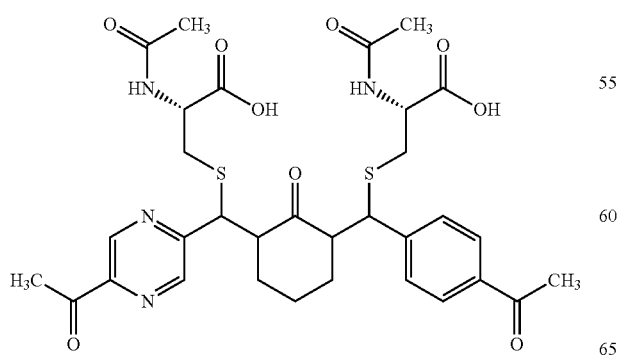
(NAC adduct of PB264)

PB266

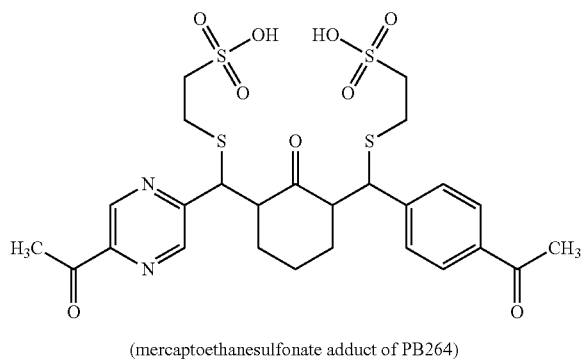
(mercaptoethanesulfonate adduct of PB264)

PB267

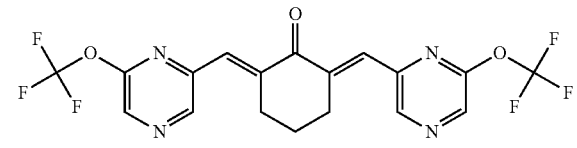
(glutathione adduct of PB264)

PB268

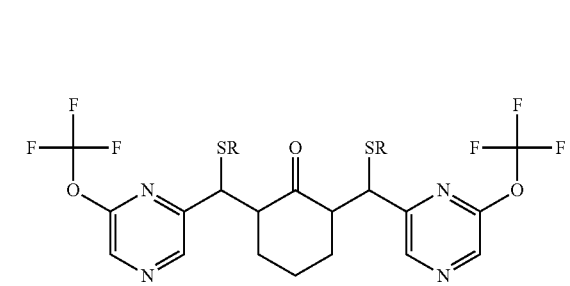

Thiol adduct of PB268, wherein —SR may be derived from N-acetylcysteine, 2-mercaptoethane sulfonate, glutahione, or another suitable thiol compound -continued

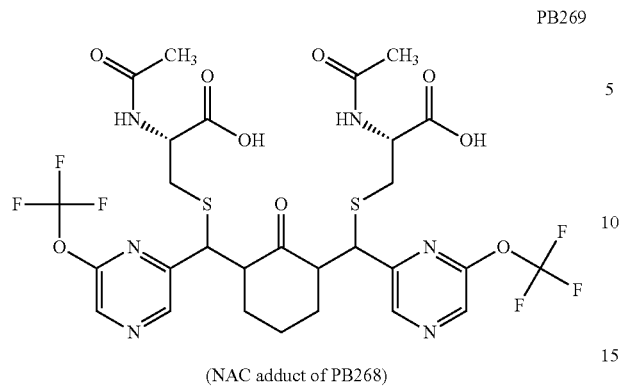

(NAC adduct of PB268) PB269

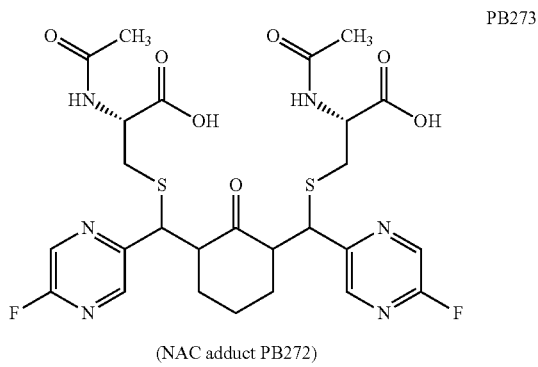

(NAC adduct PB272) PB273

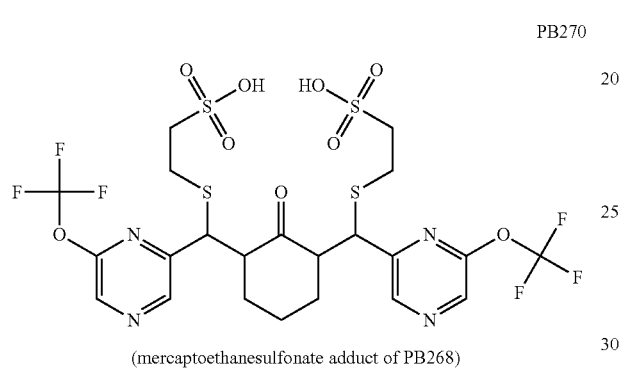

(mercaptoethanesulfonate adduct of PB268) PB270

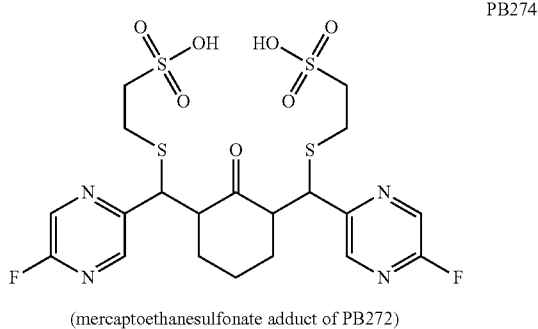

(mercaptoethanesulfonate adduct of PB272) PB274

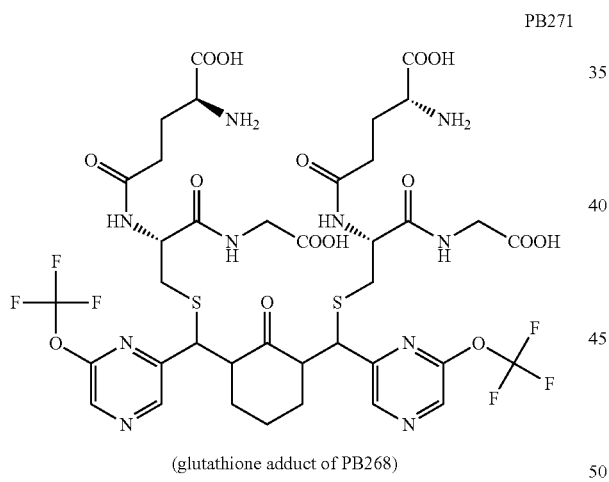

(glutathione adduct of PB268) PB271

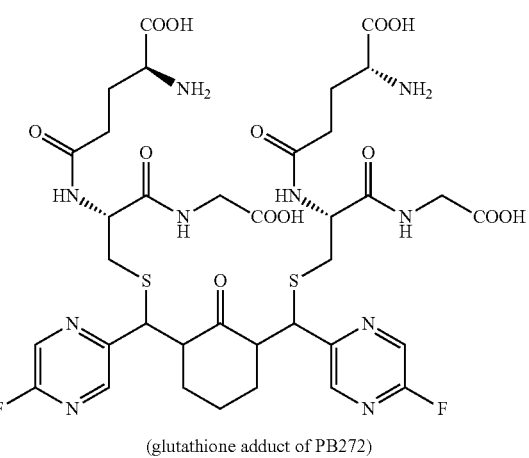

(glutathione adduct of PB272) PB275

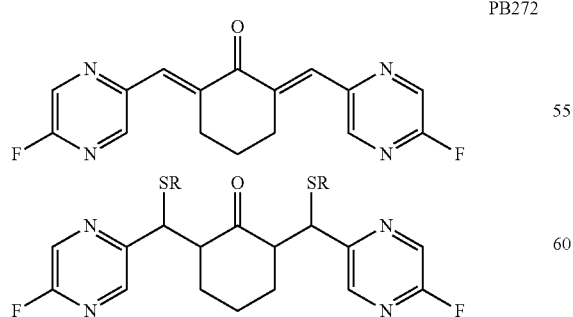

PB272

Thiol adduct of PB272, wherein —SR may be derived from N-acetylcysteine, 2-mercaptoethane sulfonate, glutathione, or another suitable thiol compound

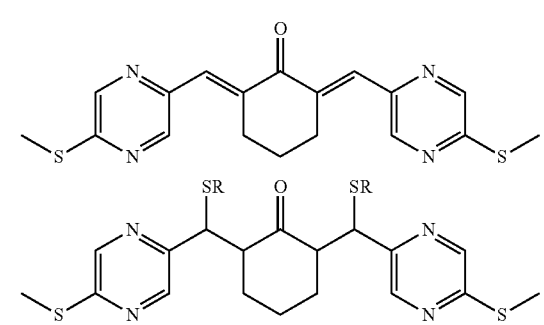

PB276

Thiol adduct of PB276, wherein —SR may be derived from N-acetylcysteine, 2-mercaptoethane sulfonate, glutathione, or another suitable thiol compound

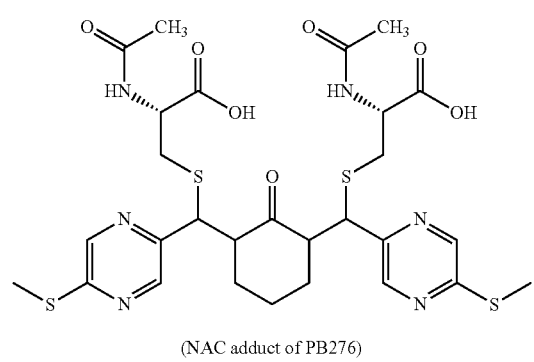

(NAC adduct of PB276) PB277

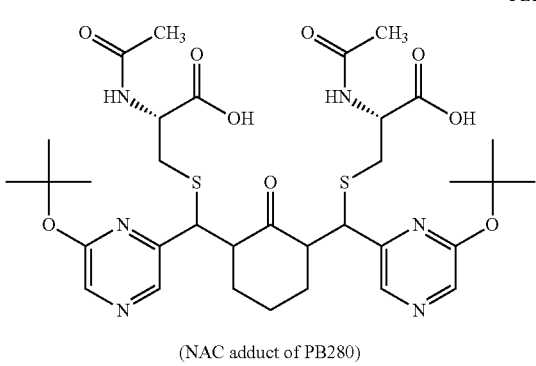

(NAC adduct of PB280) PB281

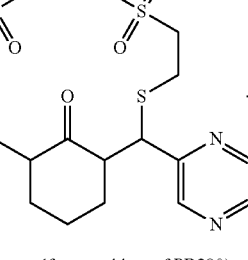

(mercaptoethanesulfonate adduct of PB276) PB278

(mercaptoethanesulfonate adduct of PB280) PB282

(glutathione adduct of PB276) PB279

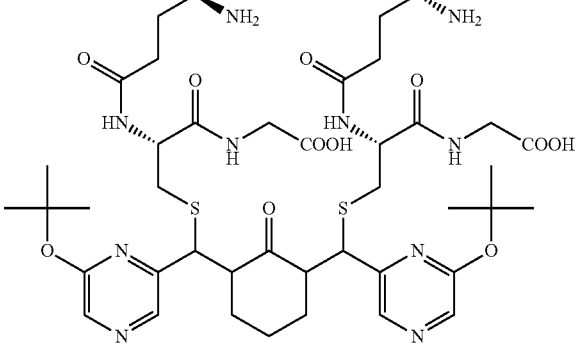

(glutathione adduct of PB280) PB283

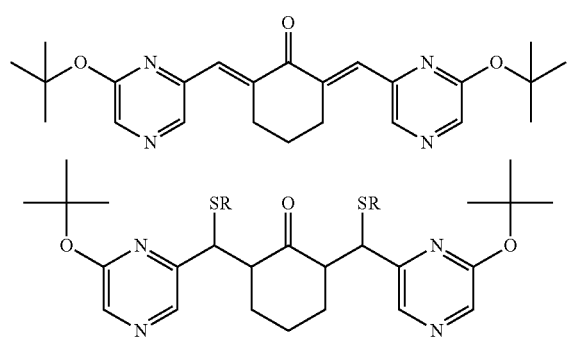

PB280

(Thiol adduct of PB289, wherein —SR may be derived from N-acetylcysteine, 2-mercaptoethane sulfonate glutathione, or another suitable thiol compound

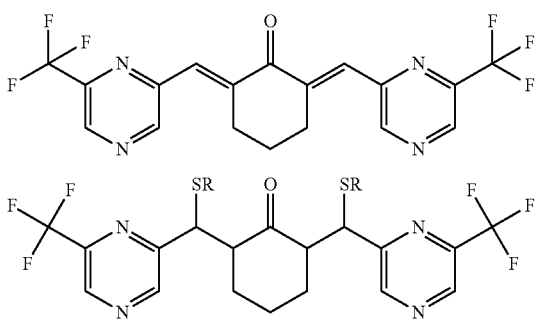

PB284

(Thiol adduct of PB284, wherein —SR may be derived from N-acetylcysteine, 2-mercaptoethane sulfonate, glutathione, or another suitable thiol compound -continued

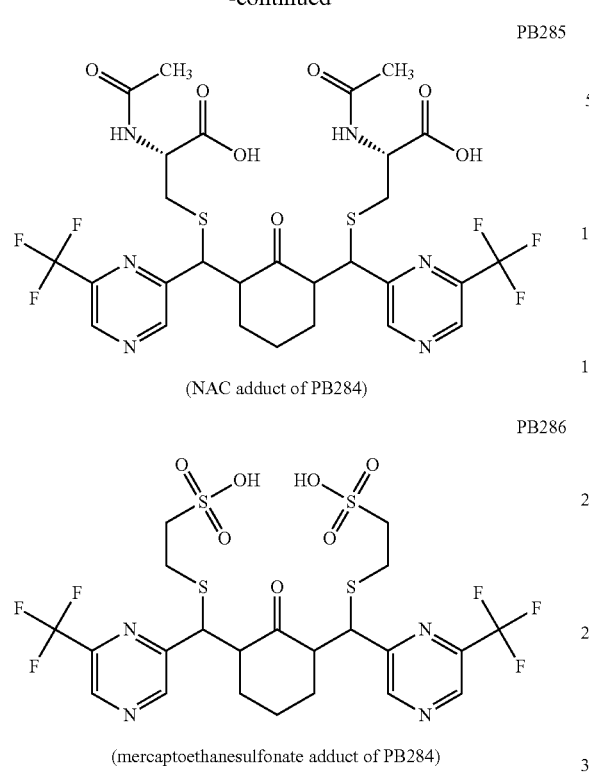

PB285
(NAC adduct of PB284)

PB286
(mercaptoethanesulfonate adduct of PB284)

PB287
(glutathione adduct of PB284)

PB288
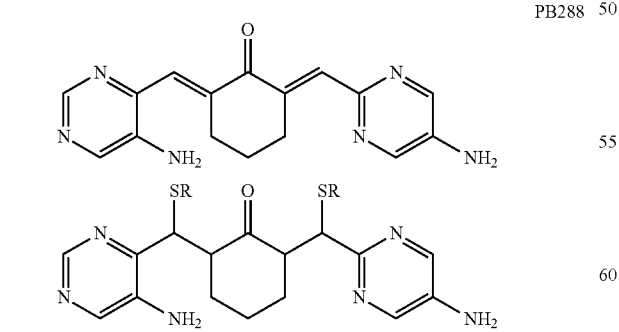

Thiol adduct of PB288, wherein —SR may be derived from N-acetylcysteine, 2-mercaptoethane sulfonate, glutathione, or another suitable thiol compound -continued

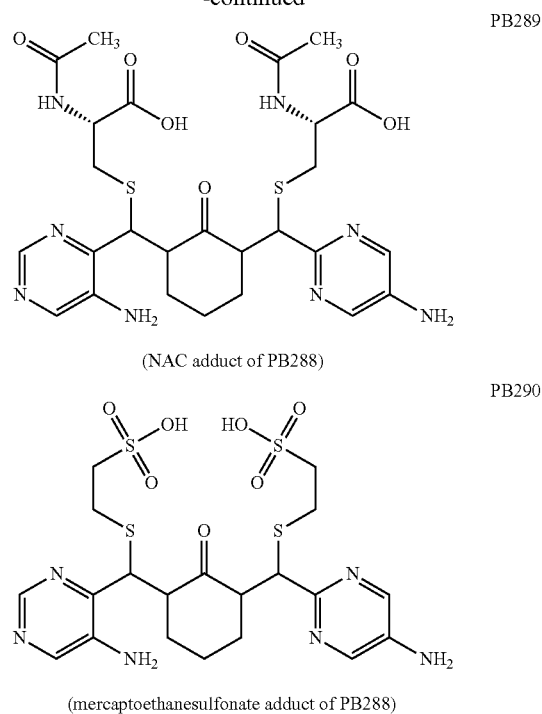

PB289
(NAC adduct of PB288)

PB290
(mercaptoethanesulfonate adduct of PB288)

PB291
(glutathione adduct of PB288)

PB292
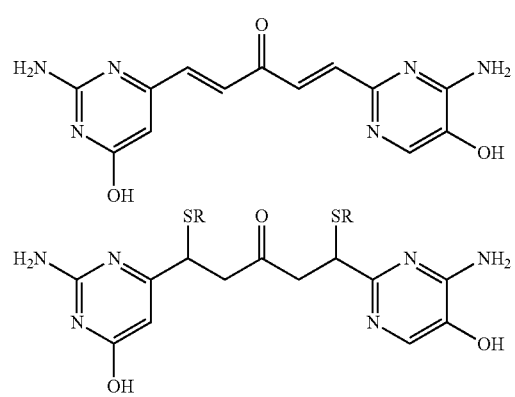

Thiol adduct of PB292, wherein —SR may be derived from N-acetylcysteine, 2-mercaptoethane sulfonate, glutathione, or another suitable thiol compound PB293
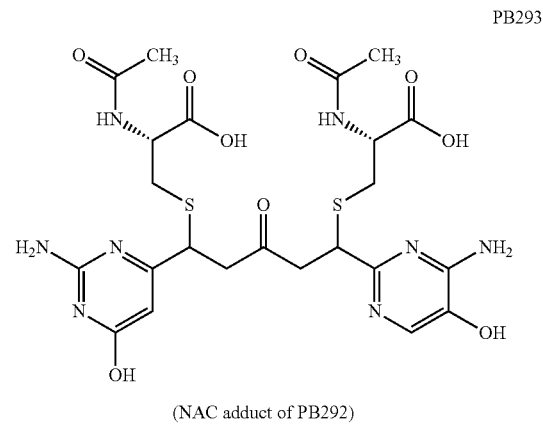
(NAC adduct of PB292)
PB294
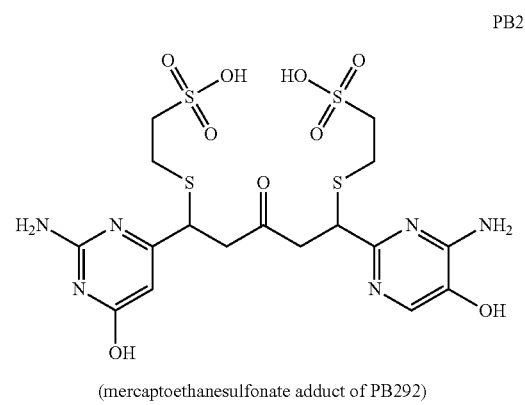
(mercaptoethanesulfonate adduct of PB292)
PB295
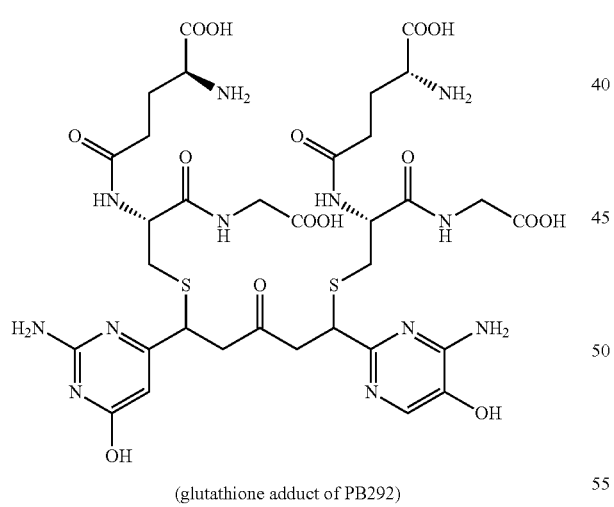
(glutathione adduct of PB292)
PB296
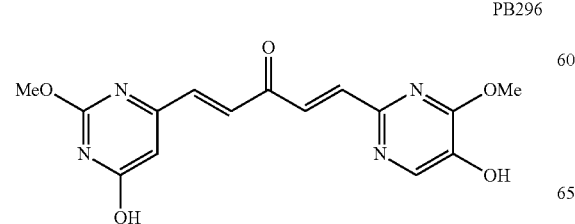
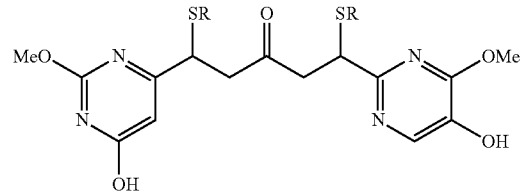
Thiol adduct of PB296, wherein —SR may be derived from N-acetylcysteine, 2-mercaptoethane sulfonate, glutathione, or another suitable thiol compound
PB297
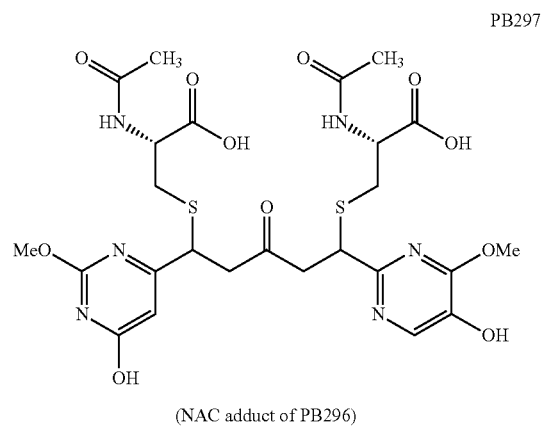
(NAC adduct of PB296)
PB298
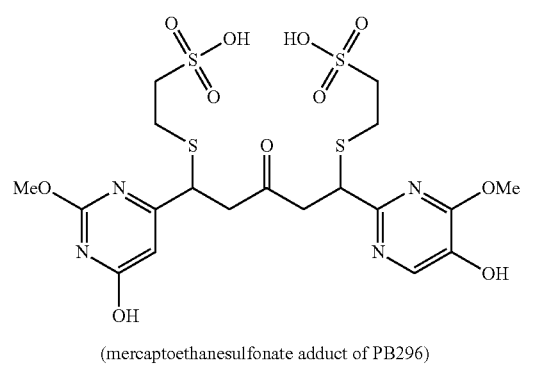
(mercaptoethanesulfonate adduct of PB296)
PB299
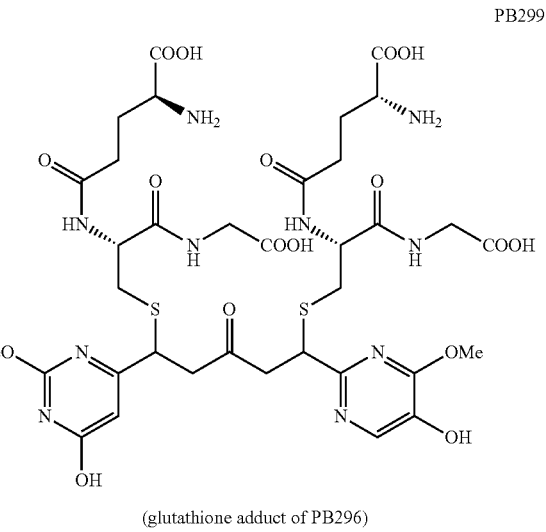
(glutathione adduct of PB296)

PB300

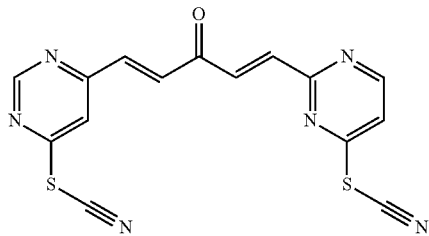

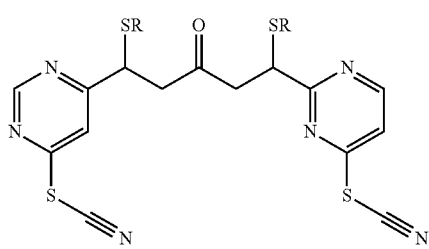

Thiol adducct of PB300, wherein —SR may be derived from N-acetylcysteine, 2-mercaptoethane sulfonate, glutathione, or another suitable thiol compound

PB301

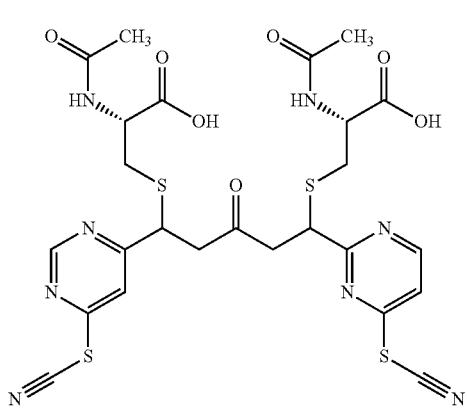

(NAC adduct of PB300)

PB302

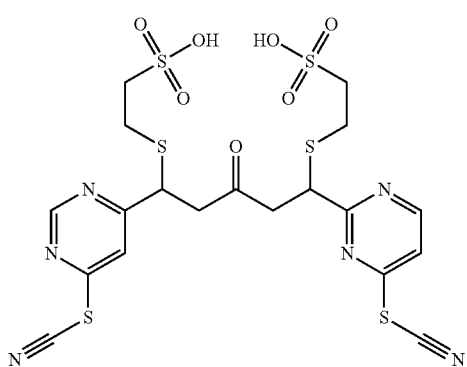

(mercaptoethanesulfonate adduct of PB300)

PB303

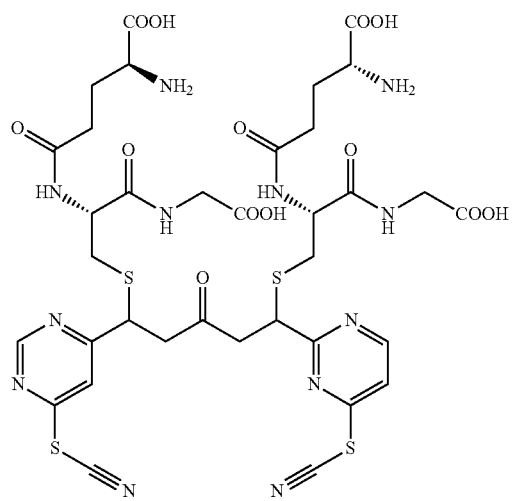

(glutathione adduct of PB300)

PB304

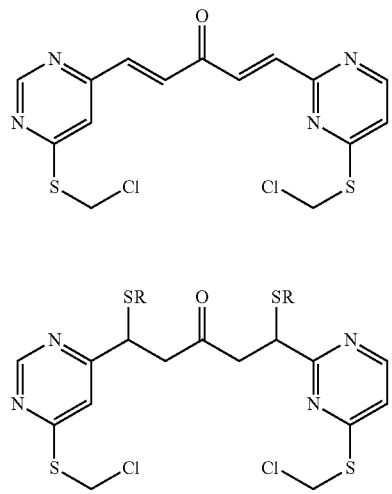

Thiol addict pf PB304, wherein —SR may be derived from N-acetylcysteine, 2-mercaptoethane sulfonate, glutathione, or another suitable thiol compound

PB305

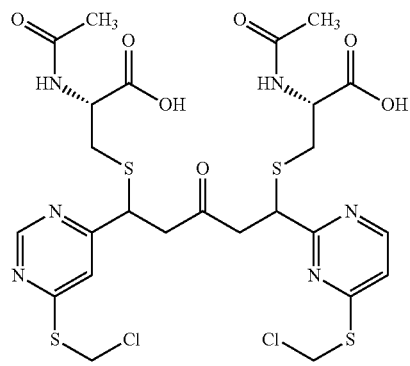

(NAC adduct of PB304)

PB306
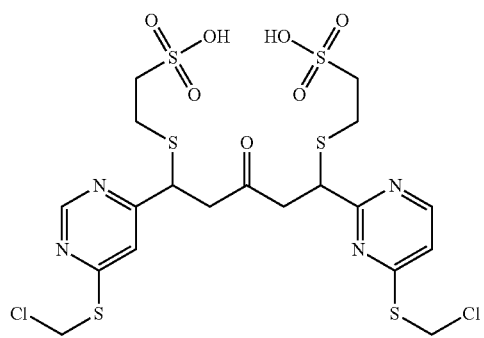
(mercaptoethanesulfonate adduct of PB304)
PB307
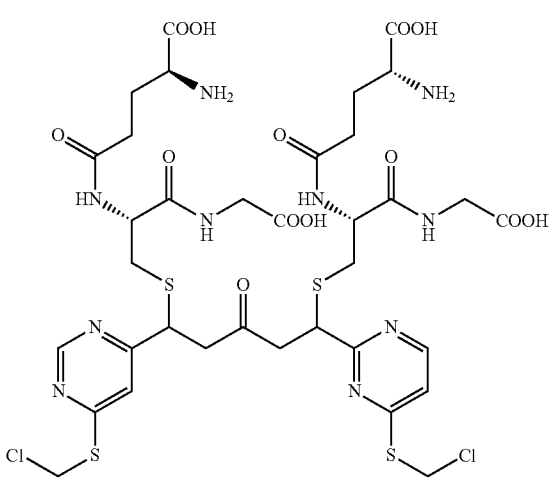
(glutathione adduct of PB304)
PB308
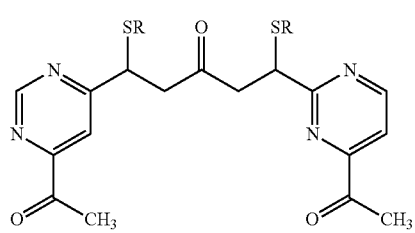
Thiol adduct of PB308, wherein —SR may be derived from N-acetylcysteine, 2-mercaptoethane sulfonate, glutathione, or another suitable thiol compound
PB309
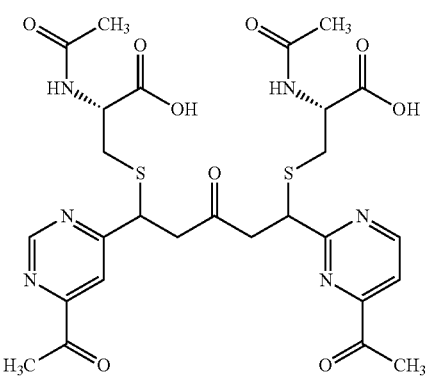
(NAC adduct of PB308)
PB310
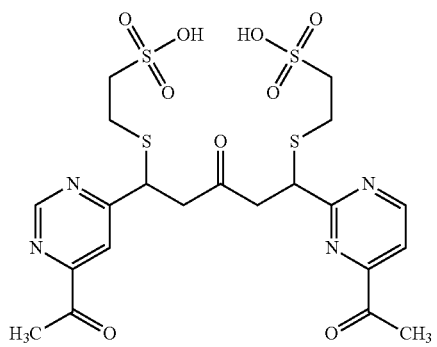
(mercaptoethanesulfonate adduct of PB308)
PB311
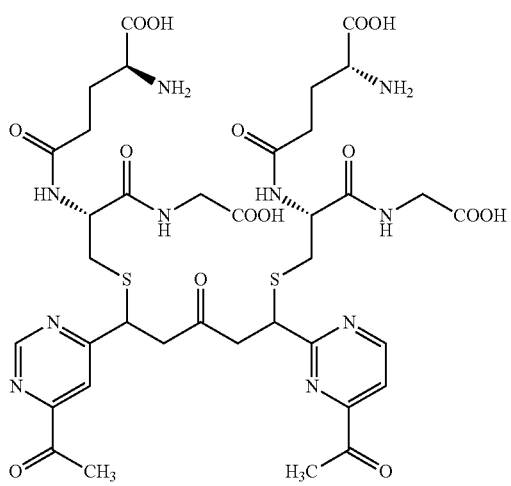
(glutathione adduct of PB308)
PB312
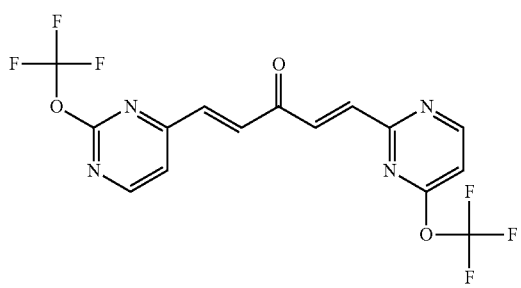

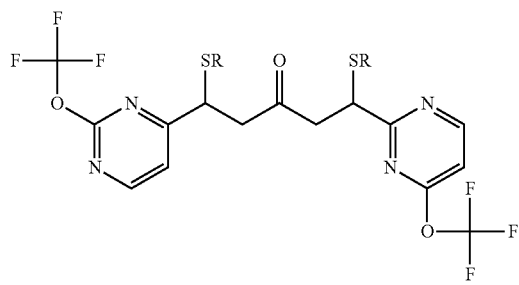

Thiol adduct of PB312, wherein —SR may be derived from N-acetylcysteine, 2-mercaptoethane sulfonate, glutathione, or another suitable compound

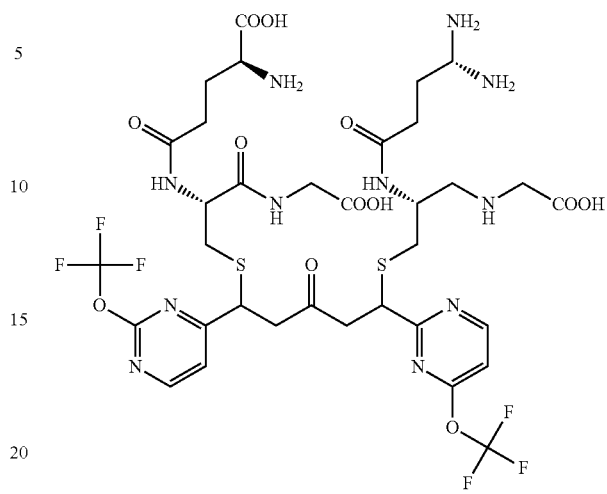

(glutathione adduct of PB312)

PB313

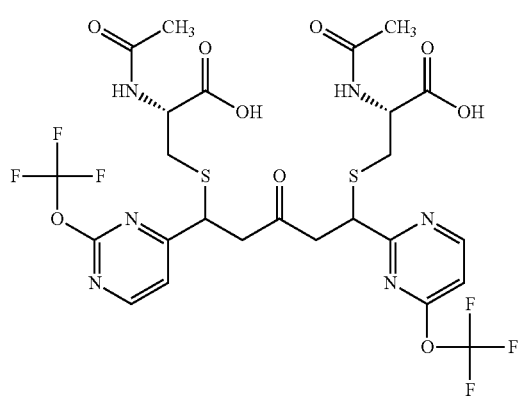

(NAC adduct of PB312)

PB315

PB316

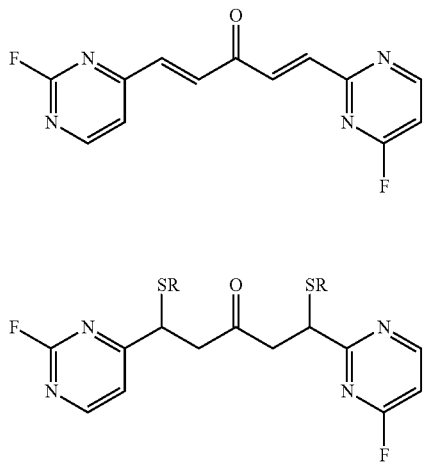

Thiol adduct of PB316, wherein —SR may be derived from N-acetylcysteine, 2-mercaptoethane sulfonate, glutahione, or anoter suitable thiol compound

PB314

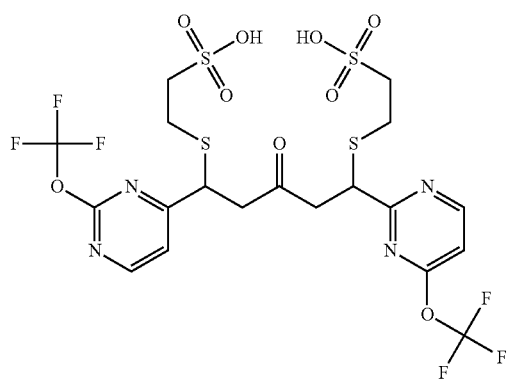

(mercaptoethanesulfonate adduct of PB312)

PB317

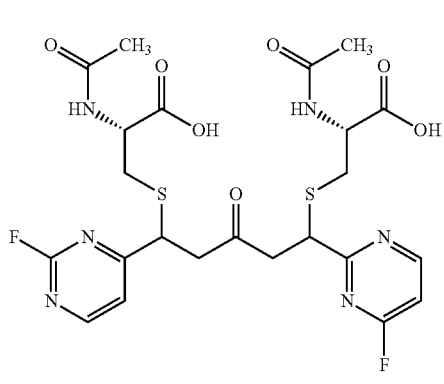

(NAC adduct of PB316)

PB318
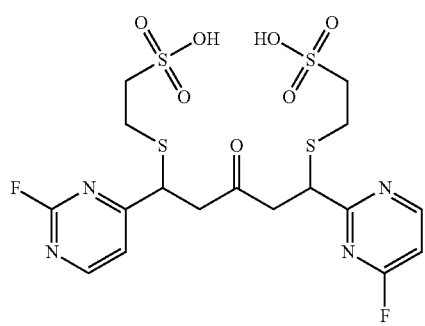
(mercaptoethanesulfonate adduct of PB316)
PB321
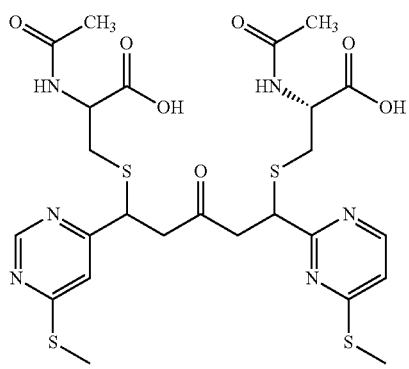
(NAC adduct of PB320)
PB319
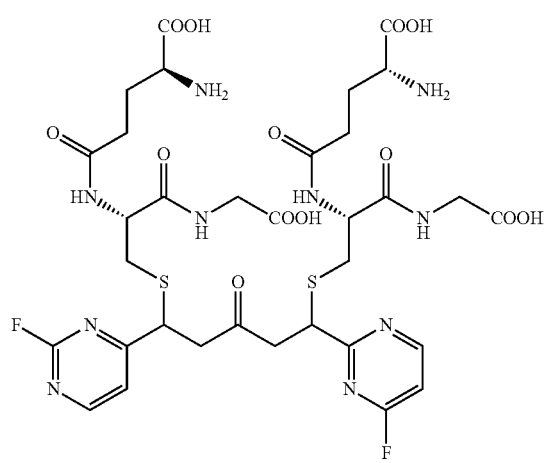
(glutathione adduct of PB316)
PB322
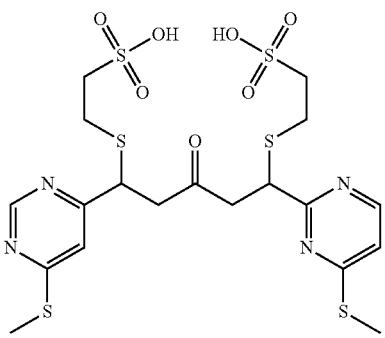
(mercaptoethanesulfonate adduct of PB320)
PB320
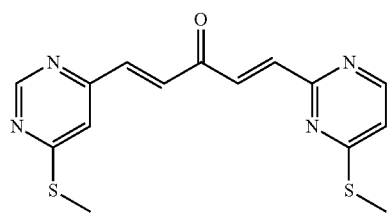
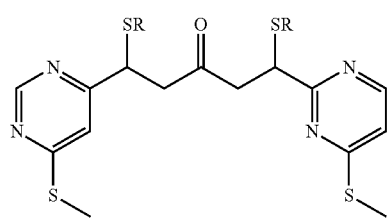
Thiol adduct of PB320, wherein —SR may be derived from N-acetylcysteine, 2-mercaptoethane sulfonate, glutathione, or another suitable thiol compound
PB323
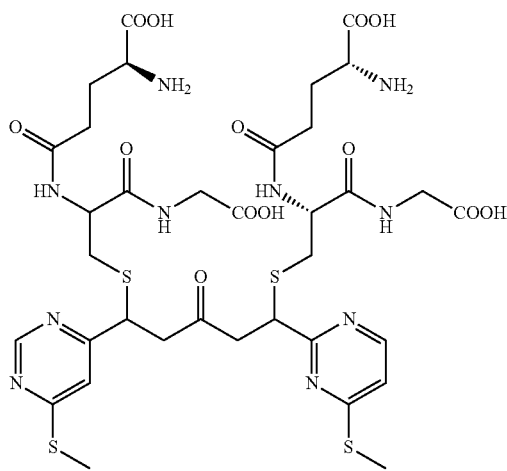
(glutathione adduct of PB320)
PB324
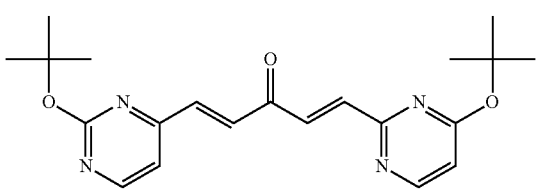

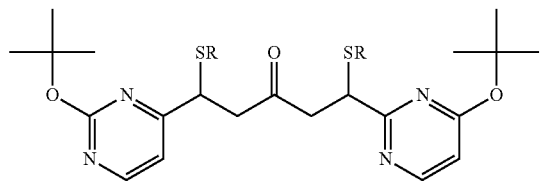

Thiol adduct of PB324, wherein —SR may be derived from N-acetylcysteine, 2-mercaptoethane sulfonate, glutathione, or another suitable thiol compound

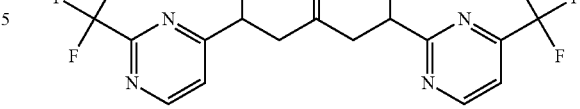

Thiol adduct of PB328, wherein —SR may be derived from N-acetylcysteine, 2-mercaptoethane sulfonate, glutathione, or another suitable thiol compound

PB325

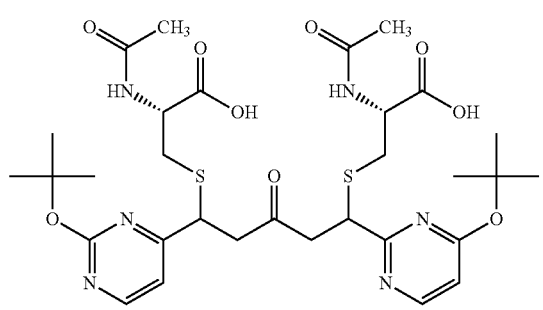

(NAC adduct of PB324)

PB329

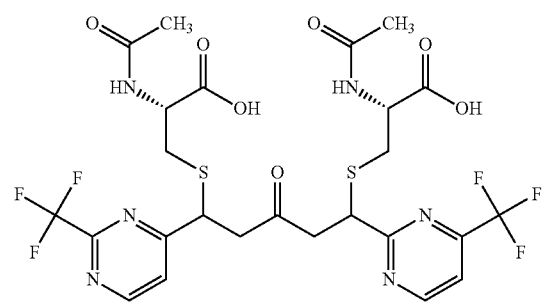

(NAC adduct of PB328)

PB326

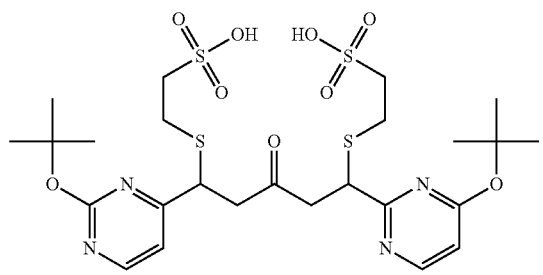

(mercaptoethanesulfonate adduct of PB324)

PB330

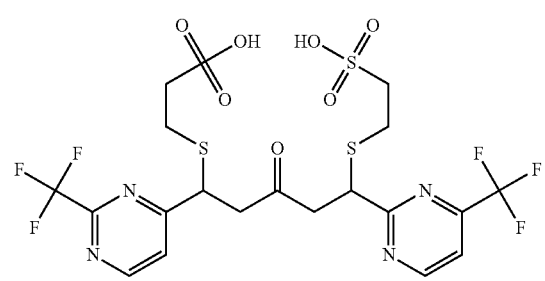

(mercaptoethanesulfonate adduct of PB328)

PB327

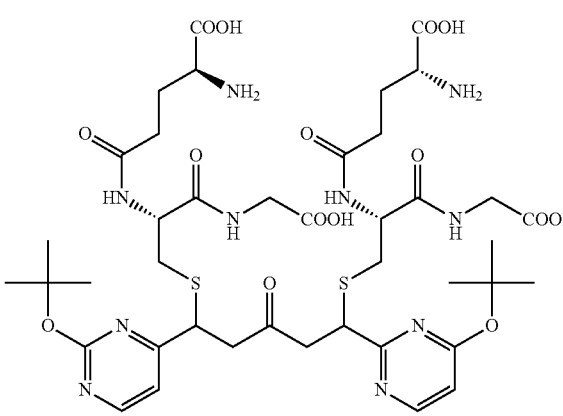

(glutathione adduct of PB324)

PB331

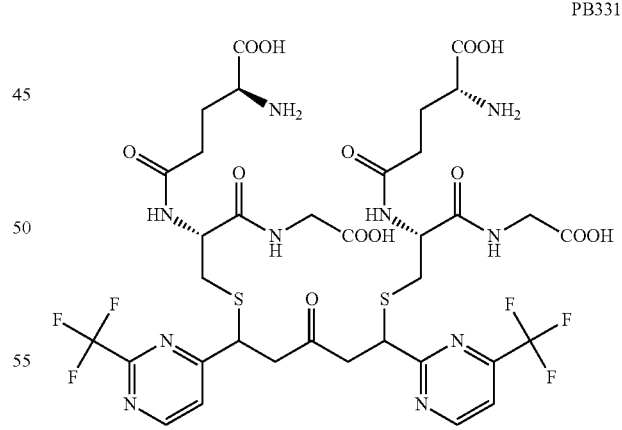

(glutathione adduct of PB328)

PB328

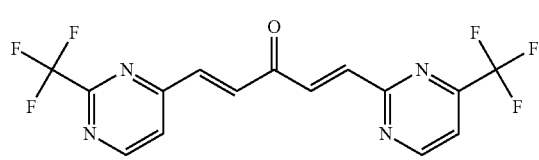

PB332

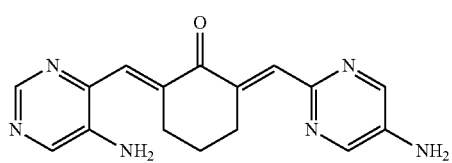

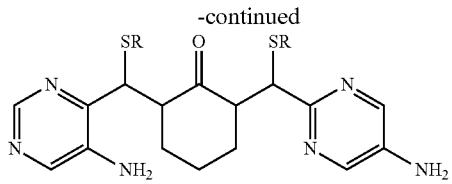

Thiol adduct of PB332, wherein —SR may be derived from N-acetylcysteine, 2-mercaptoethane sulfonate, glutathione, or another suitable thiol compound

PB333

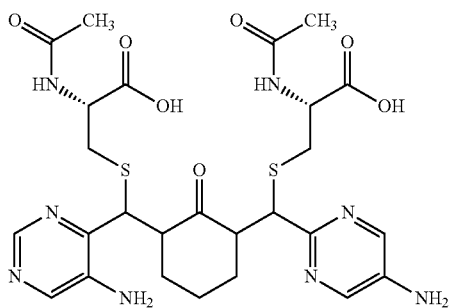

(NAC adduct of PB332)

PB334

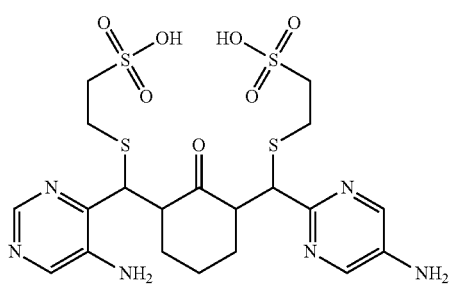

(mercpatoethanesulfonate adduct of PB332)

PB335

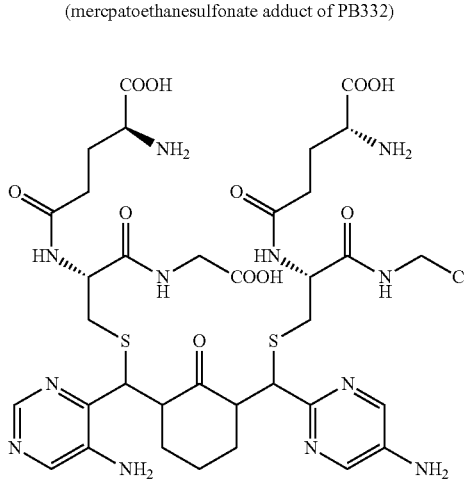

(glutathione adduct of PB332)

PB336

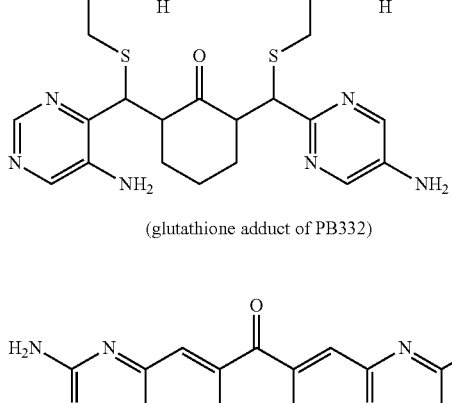

PB337

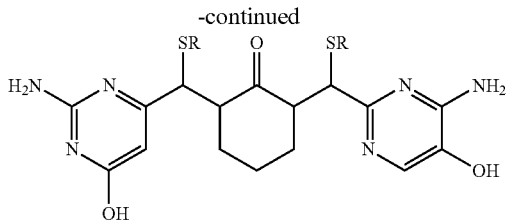

Thiol adduct of PB336, wherein —SR may be derived from N-acetylcysteine, 2-mercaptoethane sulfonate, glutathione, or another suitable thiol compound

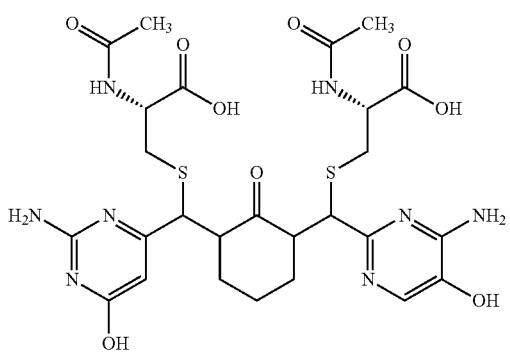

(NAC adduct of PB336)

PB338

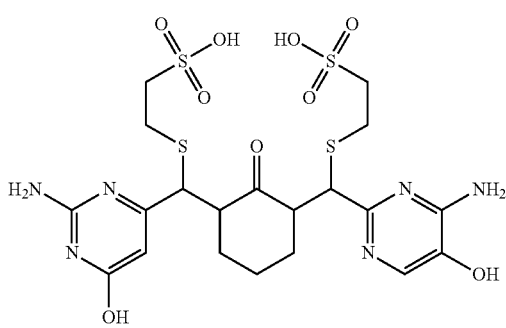

(mercaptoethanesulfonate adduct of PB336)

PB339

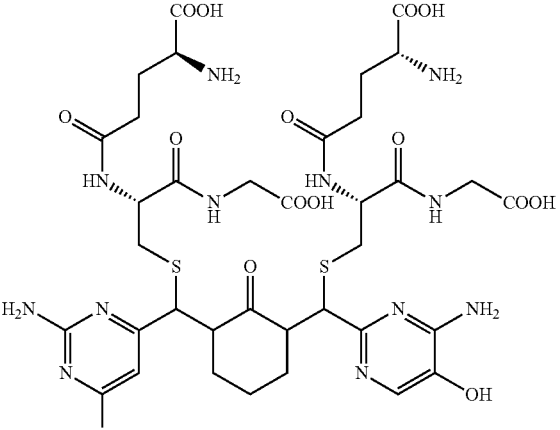

(glutathione adduct of PB336)

PB340

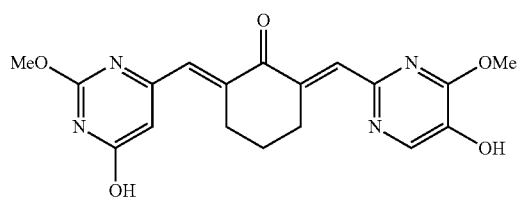

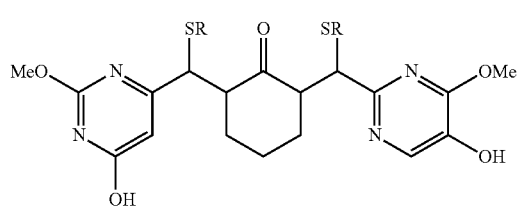

Thiol adduct of PB340, wherein —SR may be derived from N-acetylcysteine, 2-mercaptoethane sulfonate, glutathione, or another suitable thiol compoumd

PB341

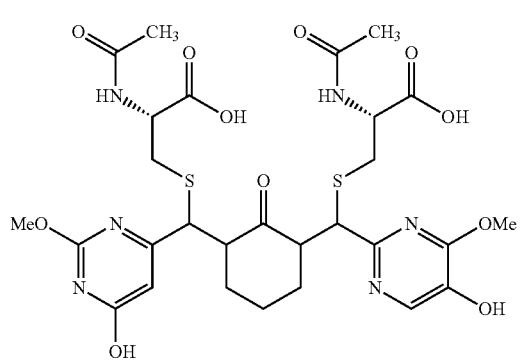

(NAC adduct of PB340)

PB342

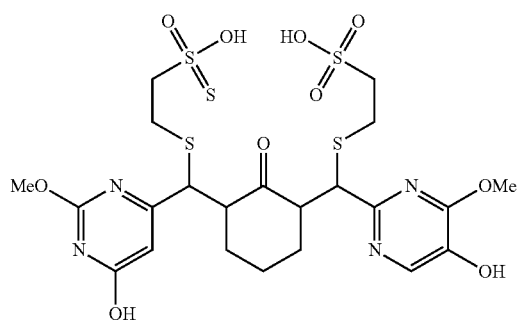

(mercaptoethanesulfonate adduct of PB340)

PB343

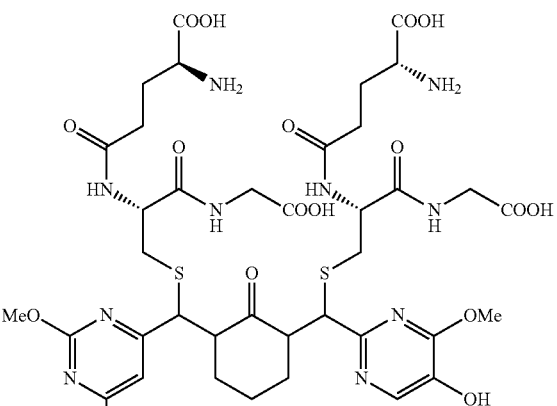

(glutathione adduct of PB340)

PB344

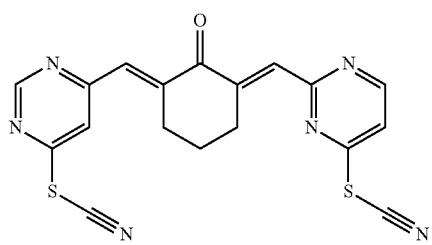

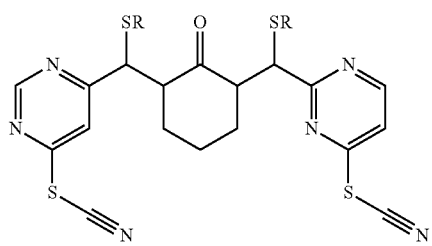

Thiol adduct of PB344, wherein —SR may be derived from N-acetylcysteine, 2-mercaptoethane sulfonate, glutathione, or another suitable thiol compound

PB345

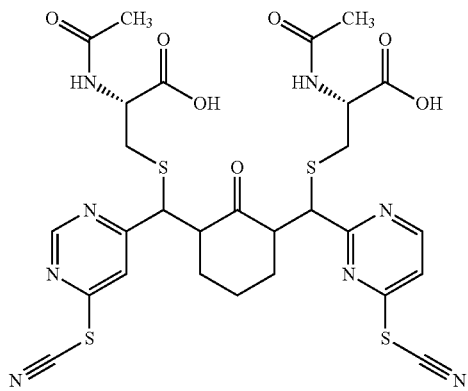

(NAC adduct of PB344)

PB346
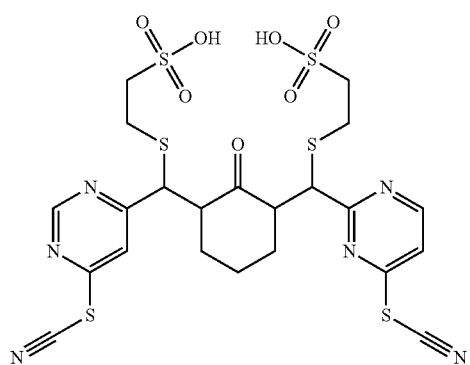
(mercaptoethanesulfonate adduct of PB344)
PB349
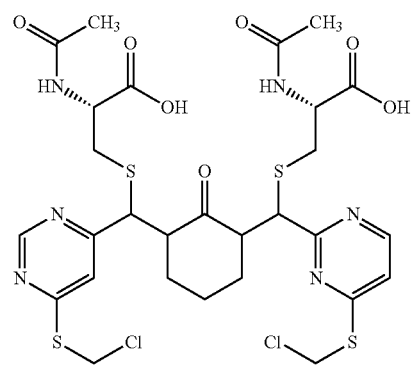
(NAC adduct of PB348)
PB347
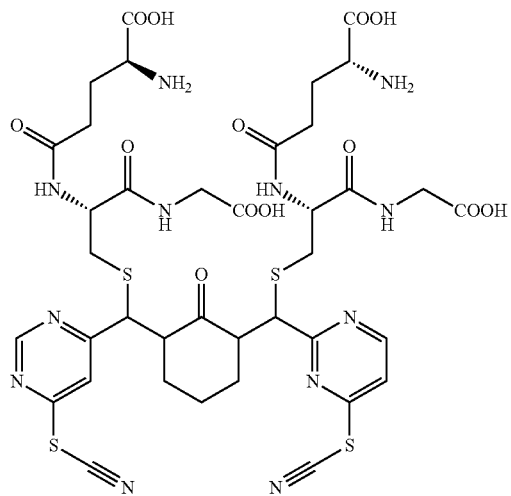
(glutathione adduct of PB344)
PB350
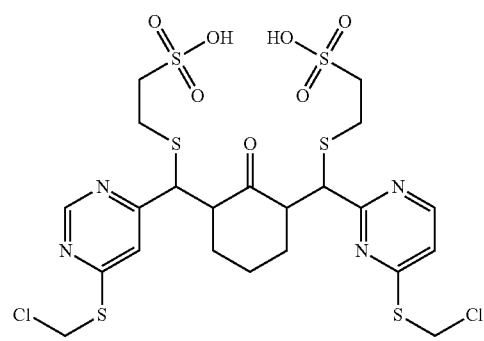
(mercaptoethanesulfonate adduct of PB348)
PB348
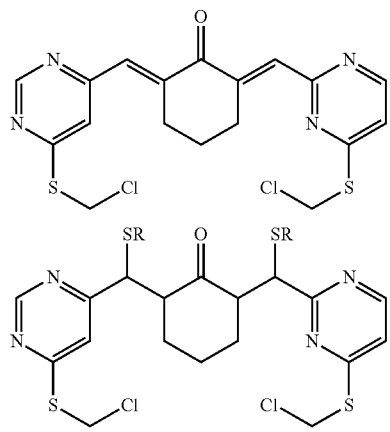
Thiol aduct of PB348, wherein —SR may be derived from N-acetylcysteine, 2-mercaptoethane sulfonate, glutathione, or another suitable thiol compound
PB351
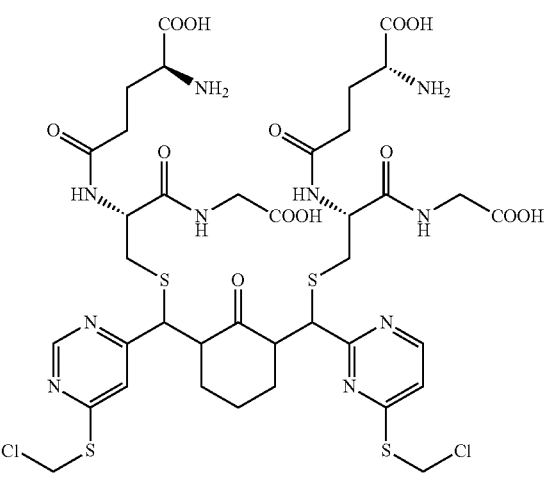
(glutathione adduct of PB348)
PB352
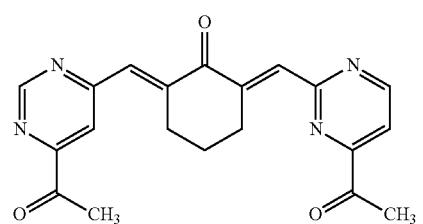

-continued

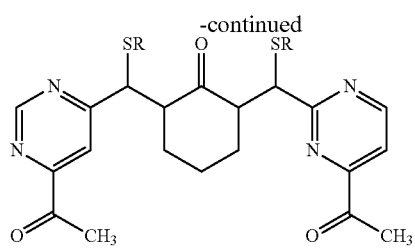

Thiol adduct of PB352, wherein —SR may be derived from N-acetylcysteine, 2-mercaptoethane sulfonate, glutathione, or another suitable thiol compound

PB353

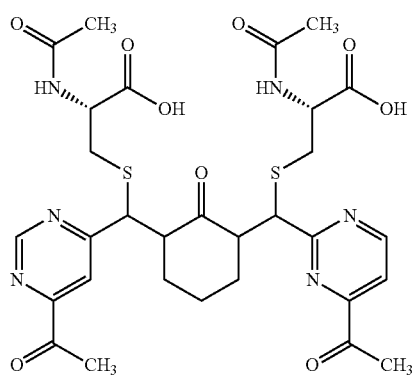

(NAC adduct of PB352)

PB354

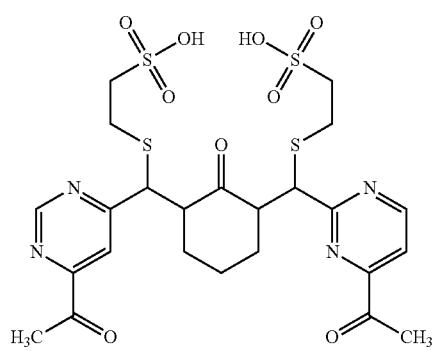

(mercaptoethanesulfonate adduct of PB352)

PB355

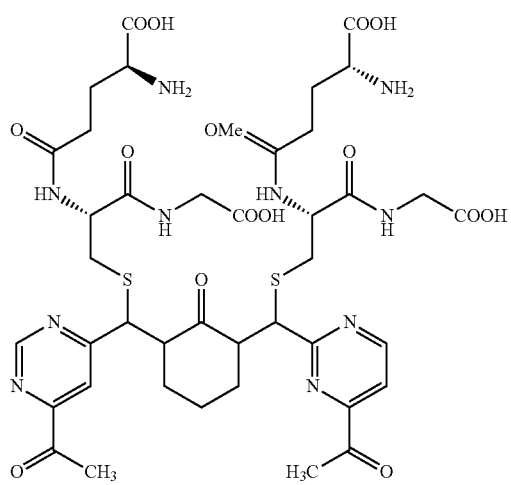

(glutathione adduct of PB352)

-continued

PB356

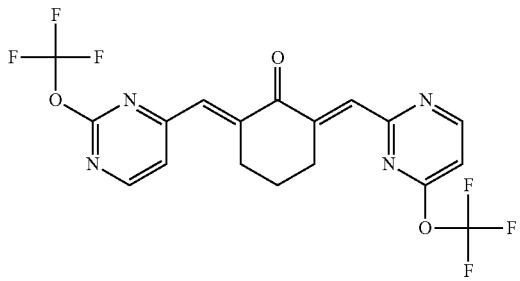

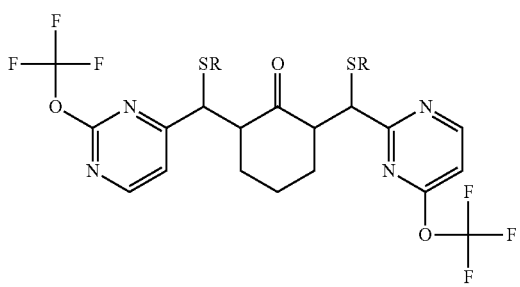

Thiol adduct of PB356, wherein —SR may be derived from N-acetylcysteine, 2-mercaptoethane sulfonate, glutathione, or another suitable thiol compound

PB357

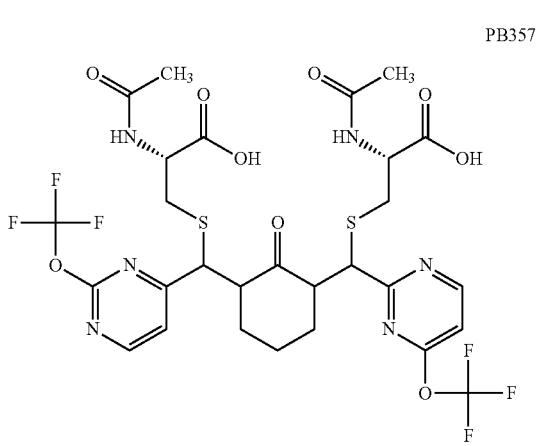

(NAC adduct of PB356)

PB358

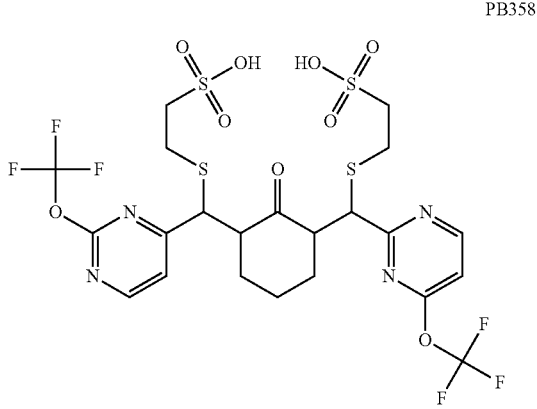

(mercaptoethanesulfonate adduct of PB356)

PB359

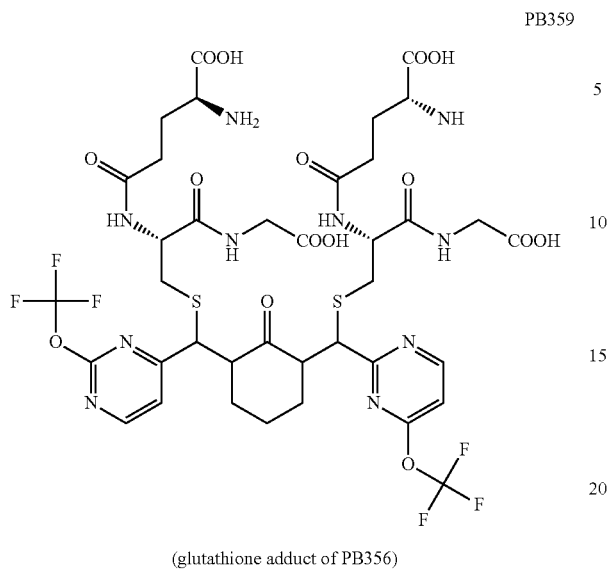

(glutathione adduct of PB356)

PB360

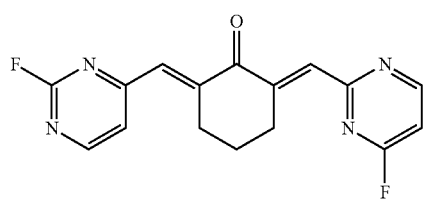

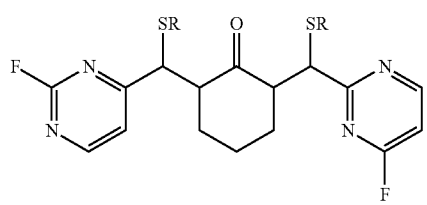

Thiol adduct of PB360, wherein —SR may be derived from N-acetylcysteine, 2-mercaptoethane sulfonate, glutathione, or another suitable thiol compound

PB361

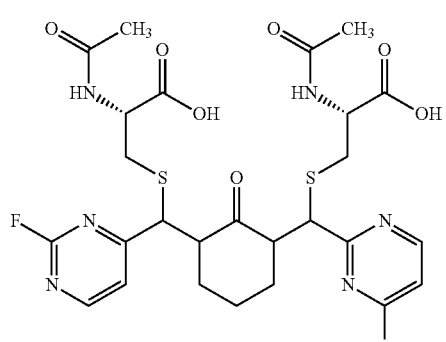

(NAC adduct of PB360)

PB362

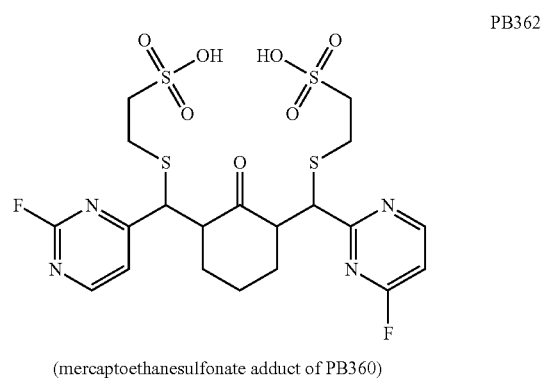

(mercaptoethanesulfonate adduct of PB360)

PB363

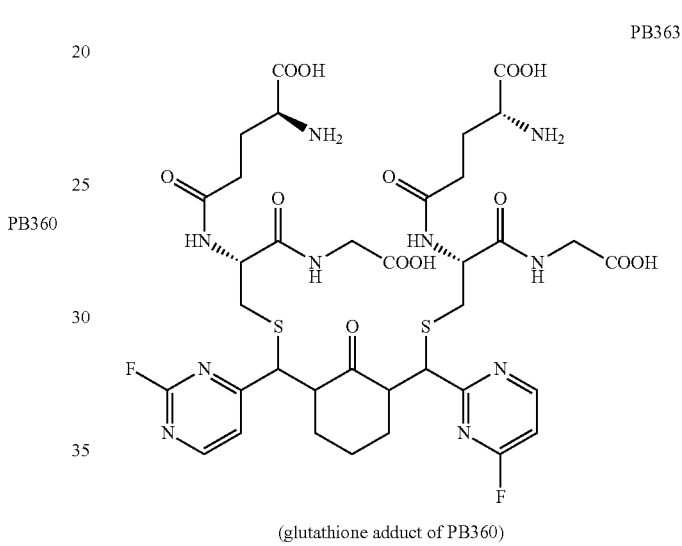

(glutathione adduct of PB360)

PB364

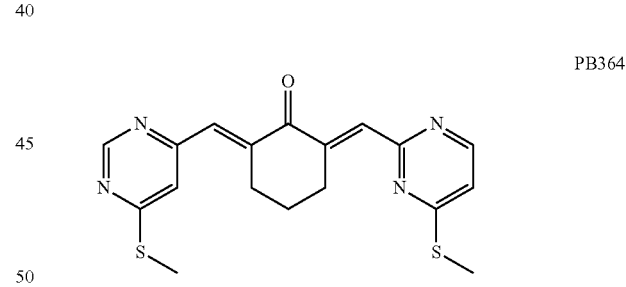

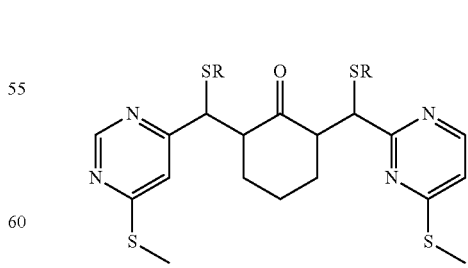

Thiol adduct of PB364, wherein —SR may be derived from N-acetylcysteine, 2-mercaptoethane sulfonate, glutathione, or another suitable thiol compound PB365
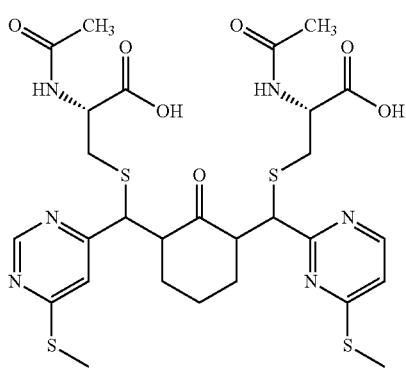
(NAC adduct of PB364)
PB366
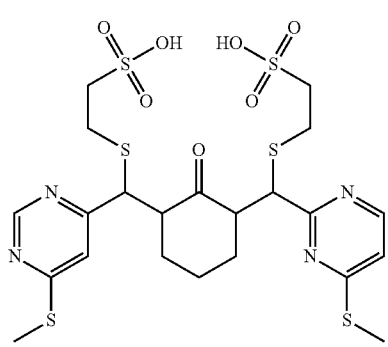
(mercaptoethanesulfonate adduct of PB364)
PB367
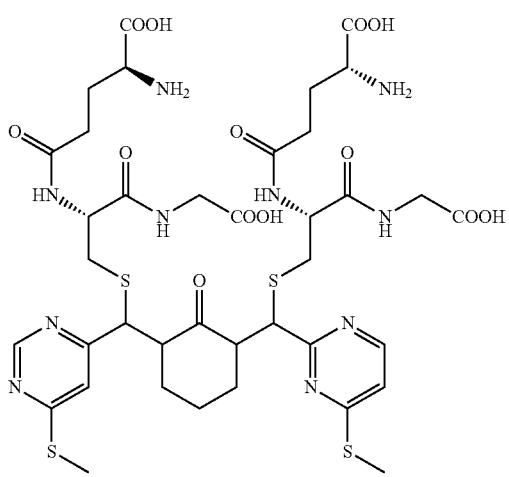
(glutathione adduct of PB364)
PB368
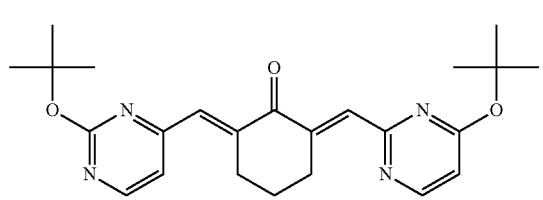
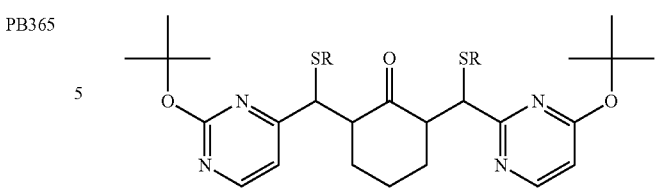
Thiol adduct of PB368, wherein —SR may be derived from N-acetylcysteine, 2-mercaptoethane sulfonate, glutathione, or another suitable thiol compound
PB369
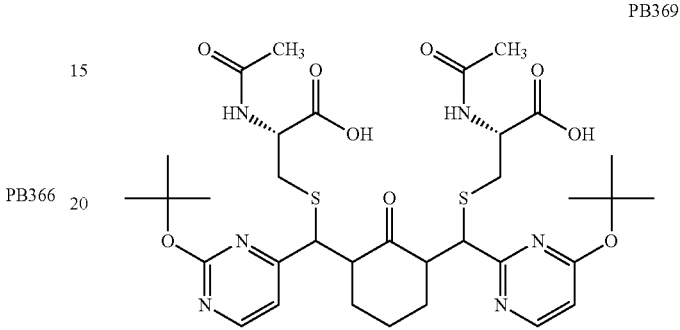
(NAC adduct of PB368)
PB370
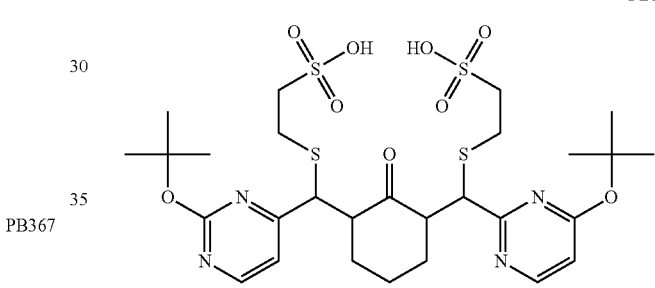
(mercaptoethanesulfonate adduct of PB368)
PB371
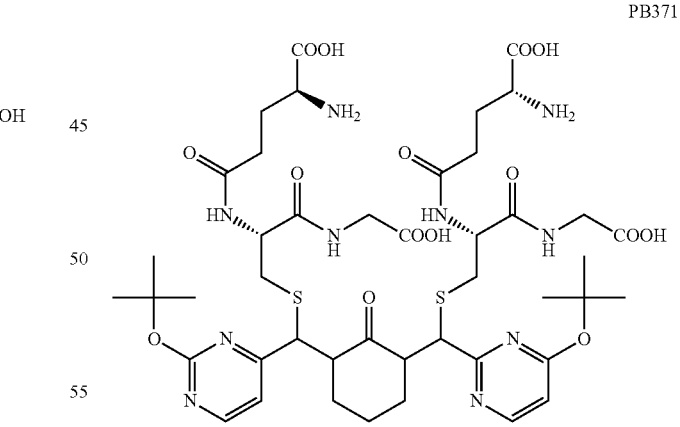
(glutathione adduct of PB368)
PB372
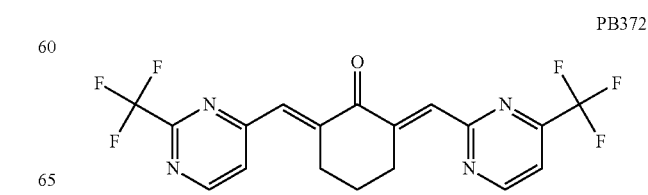

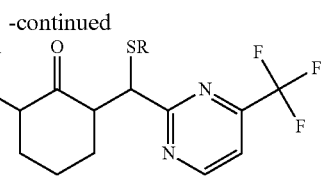

Thiol adduct of PB372, wherein —SR may be derived from N-acetylcysteine, 2-mercaptoethane sulfonate, glutathione, or another suitable thiol compound

PB373

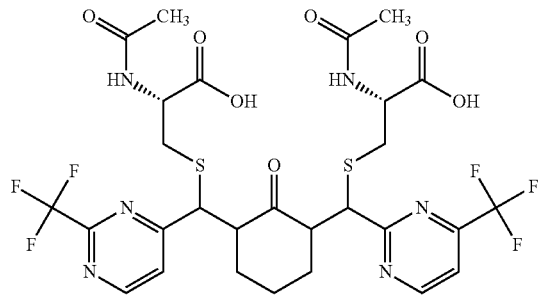

(NAC adduct of PB372)

PB374

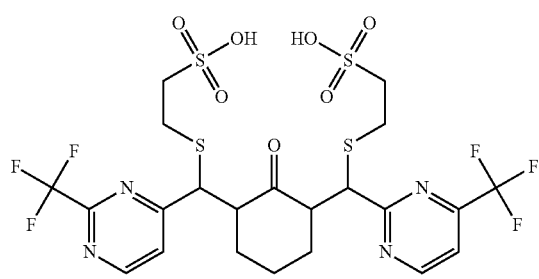

(mercaptoethanesulfonate adduct of PB372)

PB375

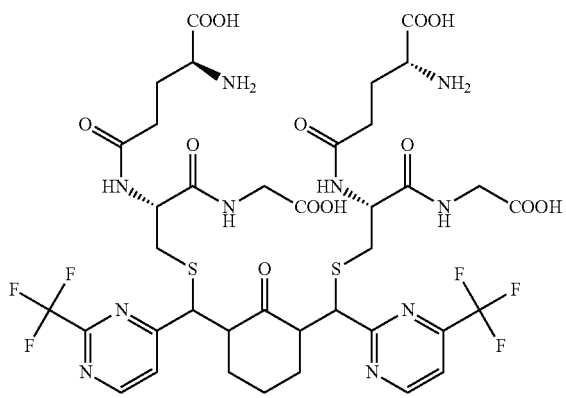

(glutathione adduct of PB372)

Pharmaceutical Compositions and Methods of Use

In certain embodiments, the compounds described herein may be useful for treating pulmonary diseases, such as lung diseases. The lung is the site of a wide variety of diseases and pathological conditions. Illustrative pulmonary diseases include pulmonary fibrosis, chronic obstructive pulmonary disease (COPD), asthma, cystic fibrosis, acute lung injury (ALI), acute respiratory distress syndrome, pulmonary hypertension, lung cancer and pulmonary manifestations of cystic fibrosis.

In certain embodiments, the compounds disclosed herein are antioxidants. For example, the compounds may oxidize radicals (e.g., oxidants, cations, etc.) that are deleterious to lung tissue.

In certain embodiments, the compounds disclosed herein may be useful for treating ischemia-reperfusion injury.

In certain embodiments, the compounds disclosed herein may inhibit NF-κB activity.

In certain embodiments, the compounds disclosed herein may inhibit lung fibroblast proliferation.

In certain embodiments, the compounds disclosed herein may inhibit myofibroblast differentiation.

In certain embodiments, the compounds described herein may be useful in ameliorating or preventing acute and chronic rejection of transplanted organs, particularly lungs.

Also disclosed herein are methods for efficiently delivering the compounds directly to the lung via formulations capable of producing either nebulized aerosols or dry powders suitable for inhalation.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface-active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, polylactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under sterile conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.25 mg/kg body weight to about 250 mg/kg body weight, such as about 1.0 mg/kg to about 100 mg/kg body weight, or about 5 mg/kg to about 50 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, an anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Example 1

General Synthesis of a PB Compound

A solution of pyrazine-2-carbaldehyde (4.62 mmol) in absolute ethanol (1 ml) is added drop-wise at room temperature over a period of 10 min, with slow stirring, to a solution of NaOH (0.75 mmol) and a ketone (acetone) in a mixture of absolute ethanol and $H_2O_2$ (14 ml; 1:1 ratio). The solution will turn yellow in color followed by formation of a yellow precipitate within 10 min. The reaction is stirred for 6 h at room temperature, after which the yellow solid is removed by filtration and washed with water; the organic phase is then dried over anhydrous $MgSO_4$ and concentrated in vacuo to give a pale yellow powder representing PB137 at 97% purity.

Example 2

Synthesis of PB Compounds with Acetone

A solution of pyrazine-2-carbaldehyde [or 3-aminopyrazine-2-carbaldehyde; 6-amino-5-hydroxypyrazine-2-carbaldehyde; 5-hydroxy-6-methoxypyrazine-2-carbaldehyde; 3-thiocyanatopyrazine-2-carbaldehyde; 5-(chloromethylthio) pyrazine-2-carbaldehyde; 5-acetylpyrazine-2-carbaldehyde; 6-(trifluoromethoxy) pyrazine-2-carbaldehyde; 5-fluoropyrazine-2-carbaldehyde; 5-(methylthio) pyrazine-2-carbaldehyde; 5-(chloromethylthio) pyrazine-2-carbaldehyde; 6-tert-butoxypyrazine-2-carbaldehyde; 5-acetylpyrazine-2-carbaldehyde; 6-trifluoromethoxypyrazine-2-carbaldehyde; 6-amino-5-hydroxypyrazine-2-carbaldehyde; 5-hydroxy-6-methoxypyrazine-2-carbaldehyde; or 6-(trifluoromethyl) pyrazine-2-carbaldehyde: (4.62 mmol)] in absolute ethanol (1 ml) is added drop-wise at room temperature over a period of 10 min, with slow stirring, to a solution of NaOH (0.75 mmol) and acetone in a mixture of absolute ethanol and $H_2O_2$ (14 ml; 1:1 ratio). The solution will turn yellow in color followed by formation of a yellow precipitate within 10 min. The reaction is then stirred for 6 h at room temperature, after which the yellow solid is removed by filtration and washed with water; the organic phase is dried over anhydrous $MgSO_4$ and concentrated in vacuo to give a pale yellow powder representing the desired PB compound at 97% purity.

Example 3

Synthesis of PB Compounds with Cyclohexanone

A solution of pyrazine-2-carbaldehyde [or 3-aminopyrazine-2-carbaldehyde; 6-amino-5-hydroxypyrazine-2-carbaldehyde; 5-hydroxy-6-methoxypyrazine-2-carbaldehyde; 3-thiocyanatopyrazine-2-carbaldehyde; 5-(chloromethylthio) pyrazine-2-carbaldehyde; 5-acetylpyrazine-2-carbaldehyde; 6-(trifluoromethoxy) pyrazine-2-carbaldehyde; 5-fluoropyrazine-2-carbaldehyde; 5-(methylthio) pyrazine-2-carbaldehyde; 5-(chloromethylthio) pyrazine-2-carbaldehyde; 6-tert-butoxypyrazine-2-carbaldehyde; 5-acetylpyrazine-2-carbaldehyde; 6-trifluoromethoxypyrazine-2-carbaldehyde; 6-amino-5-hydroxypyrazine-2-carbaldehyde; 5-hydroxy-6-methoxypyrazine-2-carbaldehyde; or 6-(trifluoromethyl) pyrazine-2-carbaldehyde: (4.62 mmol)]) in absolute ethanol (1 ml) is added drop-wise at room temperature over a period of 10 min, with slow stirring, to a solution of NaOH (0.75 mmol) and cyclohexanone in a mixture of absolute ethanol and $H_2O_2$ (14 ml; 1:1 ratio). The solution will turn yellow in color followed by formation of a yellow precipitate within 10 min. The reaction is stirred for 6 h at room temperature, after which the yellow solid is removed by filtration and washed with water; the organic phase is dried over anhydrous $MgSO_4$ and concentrated in vacuo to give a pale yellow powder representing the desired PB compound at 97% purity.

Example 4

Purification of PB137

PB137 synthesized at 94-97% purity is dissolved in ethanol at a temperature of 70° C. by adding it slowly using an addition funnel, with slow stirring, until a clear solution forms. Once the clear solution as formed, charcoal is added and the hot reaction mixture is rapidly filtered through a bed of Celite. The filtrate is cooled overnight at 4° C. to form pale yellow colored crystals representing PB137 at 99% purity. The purity and identity was confirmed by LC-MS analysis.

Example 5

Synthesis of Thiol Conjugate

N-acetyl-cysteine (NAC) (123 mg, 0.4 mmol) is dissolved in 7 ml of 50% aqueous ethanol and the pH of the resulting solution adjusted to ~7.8 using 1 N NaOH. PB137 (36 mg, 0.2 mmol) is dissolved in 3 ml of ethanol, and then added to the solution described above. The mixture is stirred at ambient temperature under $N_2$ for 3 h. The solvent is then evaporated and the crude product purified by reverse phase HPLC using a gradient of 0.05% TFA in $CH_3CN$. The overall yield of PB141 is 97%.

Example 6

Nebulization of PB141

PB141 was dissolved in water or different concentrations of PBS and aerosols were generated using a micropump nebulizer (Buxco Research Systems, Wilmington, N.C.) flowing at 10 L of air/min. Aerosol droplet size was measured with an Andersen cascade impactor. The concentration of PB141 during a 30-min nebulization period was measured by collecting samples during nebulization and analyzing them by spectrophotometer in three independent experiments. Results demonstrated droplet sizes in the optimum 1-2 μm range (FIG. 1). Nebulization was optimal for a solution of PB141 in 2% saline, although a formulation in pure water was also effective.

Example 7

TRAP Assay

The anti-oxidant activity of PB141 or PB157 was determined by the ability of these compounds to react with the pre-formed radical monocation of 2, 2'-azinobis-(3-ethylbenzothiazoline)-6-sulfonic acid ($ABTS^+$). ABTS (1.8 mmol) was reacted overnight with potassium persulfate (0.63 mmol) in double distilled water, at room temperature in the dark, to generate the dark blue $ABTS^+$ radical cation. This radical cation has a maximum absorption at 734 nm Immediately prior to the experiment, $ABTS^+$ was diluted with absolute ethanol to an absorbance of approximately 0.7 at 734 nm. PB141 or PB157 (10 μmol) was added to $ABTS^+$ (1 ml) and mixed by vortexing. The reaction was allowed to stabilize for 5 min and the absorbance was measured. The anti-oxidant activities of these compounds were determined by their ability to quench the color of the radical cation. Troxol (10 μmol) was used as reference standard. Antioxidant activity of the two compounds was clearly demonstrated. Results for PB141 shown in FIG. 2.

Example 8

FRAP Assay

The antioxidant activity of PB141 or PB157 was determined by ferric reduction/anti-oxidant power (FRAP) assay in which the compounds are reacted with ferric tripyridyltriazine complex. The ferric complex was prepared at room temperature by reaction of ferric chloride (16.7 mmol) and 2,4,6-trispyridyl-s-triazine (8.33 mmol) in pH 3.6 acetate buffer (0.25 M). The FRAP reagent was used immediately after preparation. PB141 or PB157 (10 μmol) was added to the FRAP reagent (1 ml) and mixed by vortexing. The reaction was allowed to stabilize for 5 min and the absorbance was measured. The antioxidant activities of these compounds were determined by the ability to reduce the ferric complex to a purple ferrous complex, monitored at 593 nm. Troxol (10 μmol) was used as reference standard. Antioxidant activity of the two compounds was highly significant and approximately equal. Results for PB141 shown in FIG. 2.

Example 9

PB141 Exhibits Short Half-Life in the Systemic Circulation

PB141 was dissolved in water as described above and delivered to mice by aerosolization. At 10, 20, 40, 60, 80, 100, 120, 140, 160, 180, 200, 220 and 240 min following PB141 delivery blood samples were collected from the retro-orbital plexus of mice under light anesthesia. Plasma was prepared by centrifuging the blood at 2000×g for 5 min and stored frozen at −80±10° C. until analysis. Two hundred microliters of plasma was spiked with various concentrations of PB141 (to create standard curve) or β-estradiol (internal standard) followed by two volumes of ethyl acetate. Samples were mixed for 5 min on a rocker and centrifuged at 5,000 rpm for 10 min at room temperature. The supernatant was transferred to a clean glass tube and dried under nitrogen at 40'C. Samples were reconstituted in 100 μl of mobile phase, and 50 μl was injected onto the HPLC system, a Waters 717 UV detector, and a Waters 515 pump (Milford, Mass.). A visible wavelength of 430 nm was used to detect PB141 and 280 nm to detect β-estradiol.

PB141 separation was accomplished by using the isocratic HPLC method. Samples were injected onto an Apollo reversed-phase $C_{18}$ column, 150-mm×3.9-mm×5-µm particle size (Alltech Associates, Deerfield, Ill.). The column was operated at a flow rate of 1 ml/min at room temperature. The mobile phase consisted of 1% (wt/vol) citric acid solution, adjusted to pH 3.0 using a 45% potassium hydroxide solution, in HPLC grade water, which was mixed with tetrahydrofuran in a 50:50 (vol/vol) ratio. The solution was filtered through a 0.2-µm filter. Rapid disappearance of PB141 from the blood was observed (FIG. 4).

Example 10

Nebulized Delivery of PB141 is Non-Toxic to Lung and Other Tissues

PB141 (25 mg/kg or 250 mg/kg) was aerosolized to mice daily for up to 30 consecutive days. The standard dose used in efficacy studies is 25 mg/kg for 1-10 days. At the conclusion of each experiment blood was collected and the lungs were excised and examined histopathologically for evidence of injury or toxicity. Serum levels of creatinine and aspartate (AST) and alanine (ALT) aminotransferases were measured using enzyme-linked immunosorbent assay (ELISA) kits (R&D Systems, Minneapolis, Minn.) according to the manufacturer's instructions. At the end of 30 days' exposure, other organs were also excised and similarly examined (data not shown). No evidence of injury or toxicity was found in any study (FIG. 5A, B).

Example 11

PB141 Upregulates Activity of the Antioxidant Transcription Factor Nrf2 and Inhibits the Pro-Inflammatory Transcription Factor NF-κB in Airway Epithelial Cells BEAS-2B cells were cultured in Dulbecco's modified Eagle's medium (DMEM) containing 10% heat-inactivated fetal bovine serum, penicillin, and streptomycin (100 IU/ml). Monolayer cultures were treated with different concentrations of PB141 for 24 h. Cells were then isolated and the DNA-binding activity of the antioxidant transcription factor Nrf2 was determined. The nuclear concentration of Nrf2 was also determined by Western blotting. PB141 increased both nuclear localization and DNA-binding activity of Nrf2 in a concentration-dependent manner (FIG. 6A, C). In some experiments monolayer cultures were deprived of serum for 24 h, pre-treated with different concentrations of PB141 for 1 h, then exposed to LPS for 6 h. Nuclear proteins were prepared and were used to quantify DNA-binding activity of the p65 subunit of NF-κB. PB141 inhibited NF-κB activity in a concentration-dependent manner, with almost complete inhibition being observed at a concentration of 1 μM (FIG. 6B). In other experiments, no cytotoxicity was observed at concentrations as high as 10 μM (data not shown).

In other experiments, acute lung injury was induced by intratracheal (i.t.) injection of endotoxin [lipopolysaccharide (LPS)] prepared from *Escherichia coli* O111:B6 (Sigma-Aldrich; St. Louis, Mo.). Thirty minutes later different concentrations of PB141 in isotonic saline were nebulized and delivered into cage air for 30 min using a micropump nebulizer (Buxco Research Systems, Wilmington, N.C.) fitted at the chamber inlet and flowing at 10 L of air/min. PBS was similarly delivered as a control. Nuclear proteins were prepared from lung samples and their concentrations were determined and used to quantify DNA-binding activity of the p65 subunit of the pro-inflammatory transcription factor NF-κB. PB141 inhibited the LPS-induced upregulation of NF-κB in a concentration-dependent manner (FIG. 5C).

Example 12

PB141 and PB157 Induce Apoptosis but are not Cytotoxic

To evaluate cell viability, apoptosis, and cytotoxicity, the Apo Tox-Glo Triplex assay was used according to the manufacturer's instructions (Promega, Madison, Wis.). Briefly, the BEAS-2B cells were plated at $2\times10^4$ cells/well in 100 μl medium in an opaque walled, clear-bottomed, 96-well plate. After 24 hr culture, they were treated for a further indicated time with different concentrations of PB141 or PB157. At the end of the culture period, 20 μl viability/cytotoxicity reagent was added to each well, mixed by orbital shaking (300 r.p.m. for 30 s) and incubated for 30 min at 37° C. Fluorescence was then measured with excitation at 400 nm and emission at 505 nm to assess cell viability, and 485 nm excitation and 520 nm emission to assess cytotoxicity; both were quantified as relative fluorescence units (RFU). Then, 100 μl Caspase-Glo 3/7 reagent was added to each well, mixed by orbital shaking (300 r.p.m. for 30 s) and incubated for 30 min at room temperature Luminescence was measured to assess caspase activation as a marker of apoptosis and quantified as relative luminescence units. Results for PB141 and PB157 were similar. Both compounds induced apoptosis without exhibiting cytotoxicity (data not shown).

Example 13

Nebulization of PB141 Solution Provides Efficient Delivery into the Lungs and Prevents Pulmonary Fibrosis Lung fibrosis was induced by methods previously reported in literature of the relevant art. Briefly, 50 μl of bleomycin sulfate in saline or 0.1 mg of NIEHS crocidolite asbestos (N 10 μm in length) was administered intratracheally into anesthetized mice. In some experiments fibrosis was induced by the following standard X-ray exposure procedure: Anesthetized mice at the age of 10-12 weeks were immobilized, with a lead shield excluding all but the thoracic cavity. Animals were then irradiated with a single dose of 14.5 Gy from a cesium source (J. L. Shepherd and Associates, San Fernando, Calif.) at a dose rate of 1.65 Gy/min. $LD_{50}$ for C57BL/6J mice is 14.5 Gy. At this dose, survival is sufficient to permit adequate numbers of animals for long-term analyses.

After induction of pulmonary fibrosis using the methods as described above, PB141 (25 mg/kg) dissolved in normal saline was delivered for 30 min via a micropump nebulizer (Buxco Research Systems, Wilmington, N.C.) fitted at the chamber inlet. After 21 days, bronchoalveolar lavage fluid (BALF) samples were obtained and analyzed for cellular infiltration by hemocytometer and differential staining of cells. Pulmonary fibrosis was assessed from lung homogenates by estimating total lung collagen content using the Sircol Collagen Assay kit (Biocolor) and hydroxyproline content using a hydroxyproline assay kit (BioVision, Mountain View, Calif.) according to the manufacturer's instructions. Lung histology sections were assessed by morphometry, hematoxylin and eosin (H&E) staining, and Masson's trichrome staining. Delivery of the nebulized PB141 composition effectively prevented inflammatory cell infiltration, collagen production, and myofibroblast differentiation, which indicated that effective doses of PB141 were delivered into the lungs. Repeated pulmonary dosing of the solution (25 mg/kg) significantly reduced pulmonary fibrosis (FIG. 9 shows results for bleomycin induction only). The solution was well tolerated even with intratracheal administration.

Figure 8A:
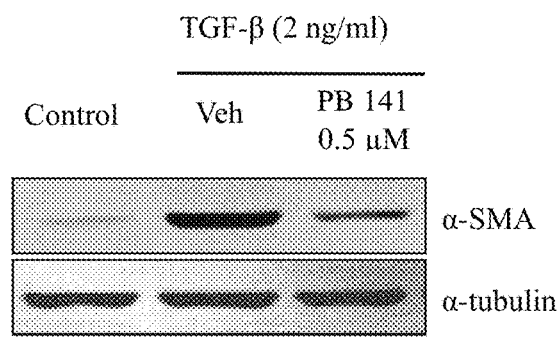
FIGS. 8A-8C show that PB141 inhibits TGF-β-induced myofibroblast differentiation. IMR-90 cells were cultured in Dulbecco's modified Eagle's medium (DMEM) containing 10% heat-inactivated fetal bovine serum, penicillin, and streptomycin (100 IU/ml). Monolayer cultures were deprived of serum for 24 h, pre-treated with 0.5 μM PB141 or with vehicle (saline) for 1 h, and then exposed to 2 ng/ml TGF-β for 24 h.
Figure 8B:
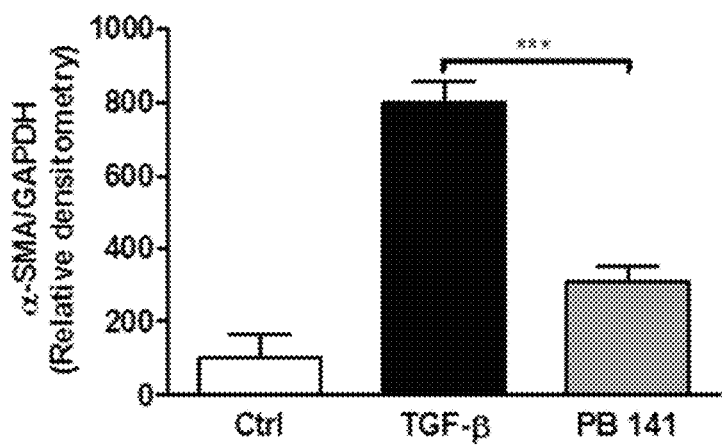
Figure 8C:
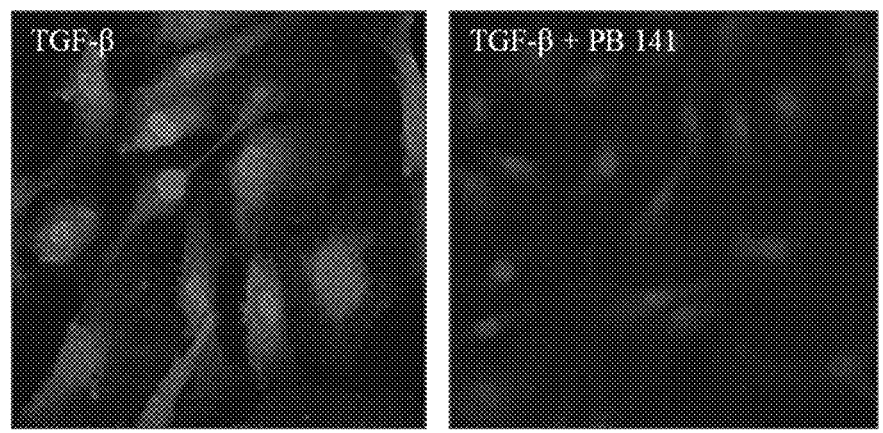
Figure 9A:
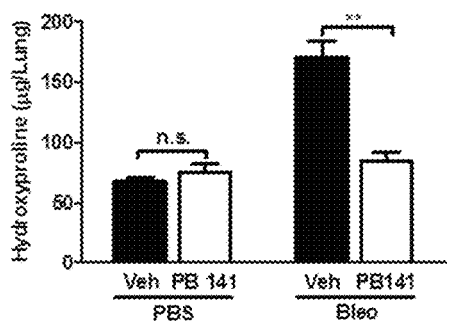
FIGS. 9A-9D show that nebulized PB141 reduces bleomycin-induced pulmonary fibrosis. Induction of pulmonary fibrosis by intratracheal injection of bleomycin sulphate (BLM; 0.05 units) was followed by nebulization of PB141 (25 mg/kg) or vehicle (saline) and delivery to cage air via a micropump nebulizer. After 21 days lung samples were obtained.
Figure 9B:
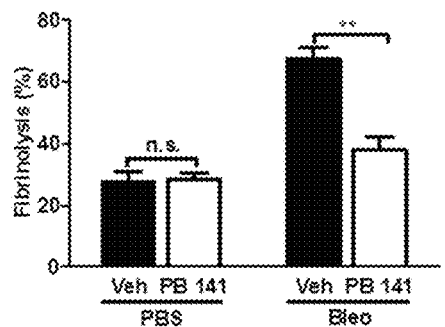
Figure 9C:
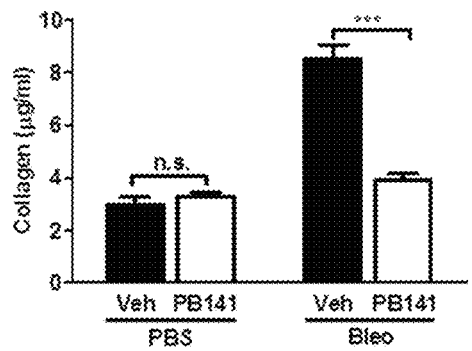
Figure 9D:
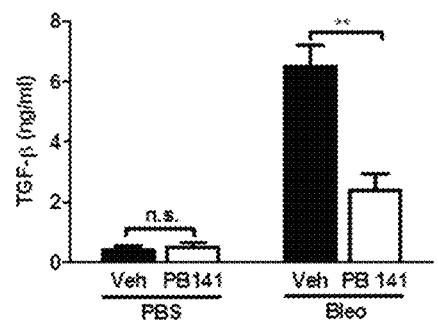
Figure 10F:
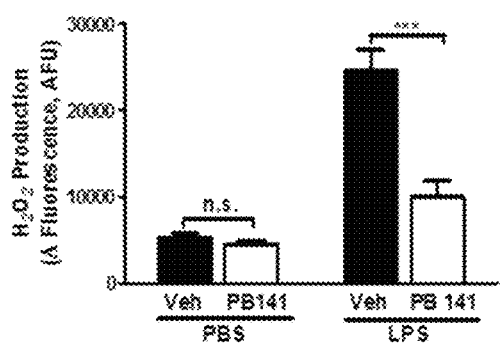
Figure 10G:
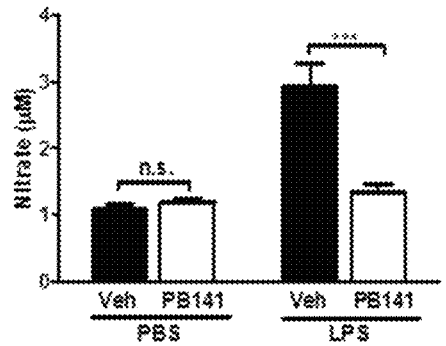
Figure 10H:
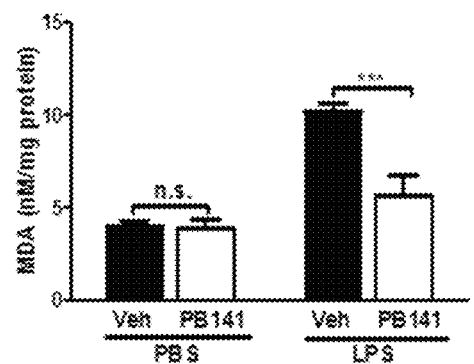
Figure 10I:
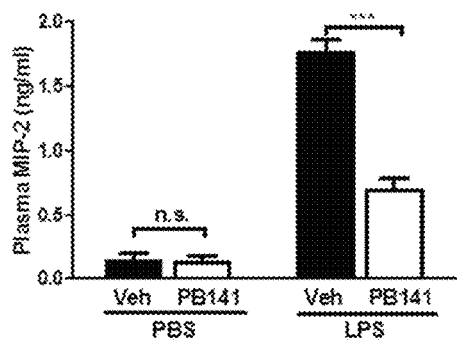
Figure 10J:
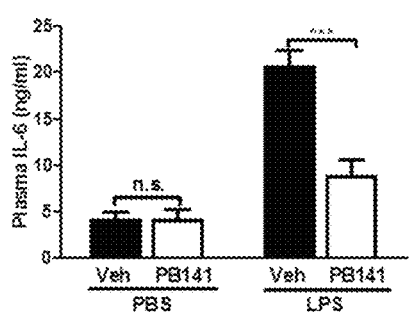
Figure 10K:
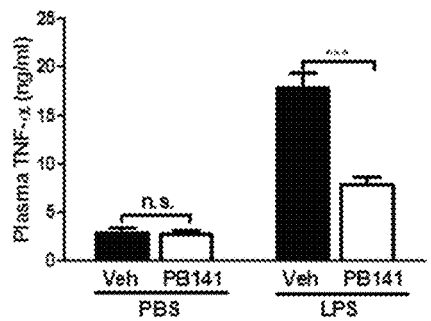
Figure 10L:
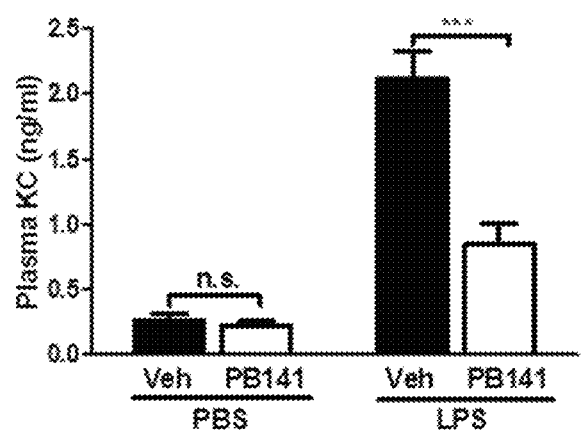

Additional in vitro experiments were performed using normal human fetal lung fibroblasts (IMR-90; Institute for Medical Research, Camden, N.J.) or fibroblasts grown from mechanically dissociated surgical lung biopsy of histologically normal or usual interstitial pneumonia (UIP) patients. Cells were serum-starved for 24 hr and treated with recombinant 2 mg/ml TGF-β (R&D Systems, Minneapolis, Minn.) for 24 h. In some experiments cells were pretreated with 0.1 to 1 μM PB141 prior to TGF-β treatment. Total cell protein extracts were prepared and assayed for cell proliferation and myofibroblast markers by western blot. Immunohistochemical staining was performed for α-SMA following treatment. Pretreatment with PB141 inhibited proliferation (FIG. 7) and differentiation to myofibroblasts by human lung fibroblasts, including those from UIP patients (FIG. 8).

Example 14

Nebulization of PB141 Solution Provides Efficient Delivery into the Lungs and Prevents Lung Injury Acute lung injury was induced by intratracheal injection of endotoxin (lipopolysaccharide; LPS) prepared from *Escherichia coli* 0111:B6 (Sigma-Aldrich; St. Louis, Mo.) into anesthetized mice. In other experiments, systemic sepsis was induced by intraperitoneal injection of endotoxin. Thirty minutes later PB141 (25 mg/kg) or vehicle (saline) was delivered to mice for 30 minutes via a micropump nebulizer (Buxco Research Systems, Wilmington, N.C.) fitted at the chamber inlet. Extent of lung injury after 5.5 h and systemic sepsis after 12 h were assessed by measuring lung tissue myeloperoxidase activity, polymorphonuclear neutrophil (PMN) count in bronchoalveolar lavage fluid, lung vascular permeability, pulmonary edema, and cytokine generation. Lung histology sections were assessed microscopically for evidence of inflammation and injury following hematoxylin and eosin (H&E) staining.

Figure 11A:
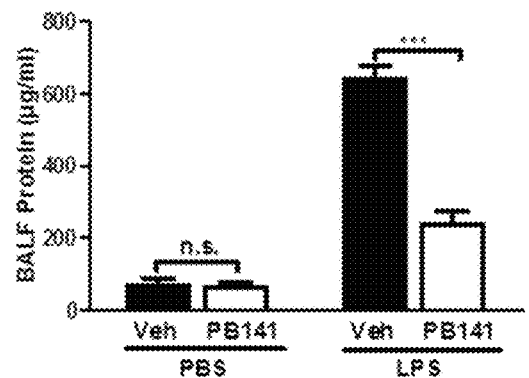
FIGS. 11A-11C show that nebulized PB141 reduces LPS-induced lung injury. Induction of ALI by intratracheal injection of LPS (50 μg) was followed 30 min later by nebulization of PB141 (25 mg/kg) or vehicle (saline) and delivery to cage air via a micropump nebulizer. After a further 5.5 h, BAL fluid and lung samples were obtained.
Figure 11B:
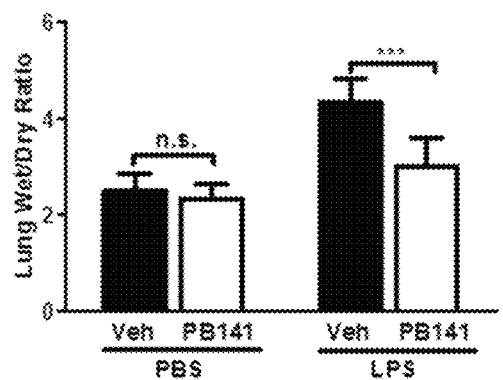
Figure 11C:
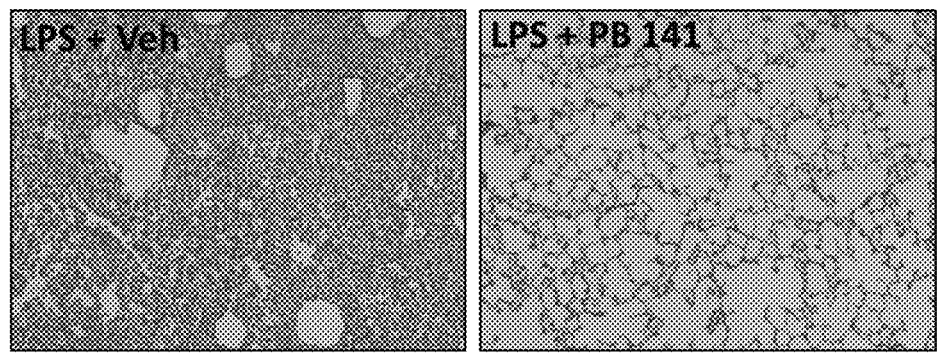
Figure 12:
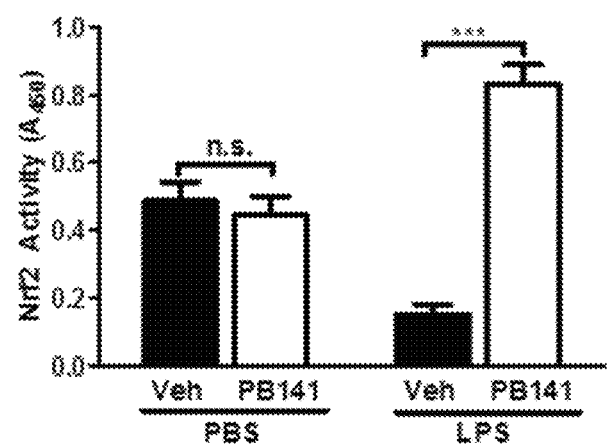
FIG. 12 shows that PB141 reverses the LPS-induced decrease in transcription factor Nrf2 activity. Induction of ALI by intratracheal injection of LPS (50 μg) was followed 30 min later by nebulization of PB141 (25 mg/kg) or vehicle (saline) and delivery to cage air via a micropump nebulizer. After another 5.5 h lungs were excised and DNA-binding activity of the transcription factor Nrf2 was determined. Data is representative of one of two independent experiments with n=4-6 mice per group; ***p<0.001.

As shown in FIG. 10, delivery of the PB141 solution via nebulization effectively prevented PMN infiltration into the alveolar space, as shown by both decreased PMN count in BAL fluid and decreased lung myeloperoxidase activity. PB141 also reduced vascular permeability (FIG. 11A), edema (FIG. 11B), oxidant stress (FIG. 10F-H) and cytokine generation (FIG. 10 I-L). Decreased lung injury was seen histologically in lungs of mice receiving the nebulized PB141 solution (FIG. 11C).

Figure 13:
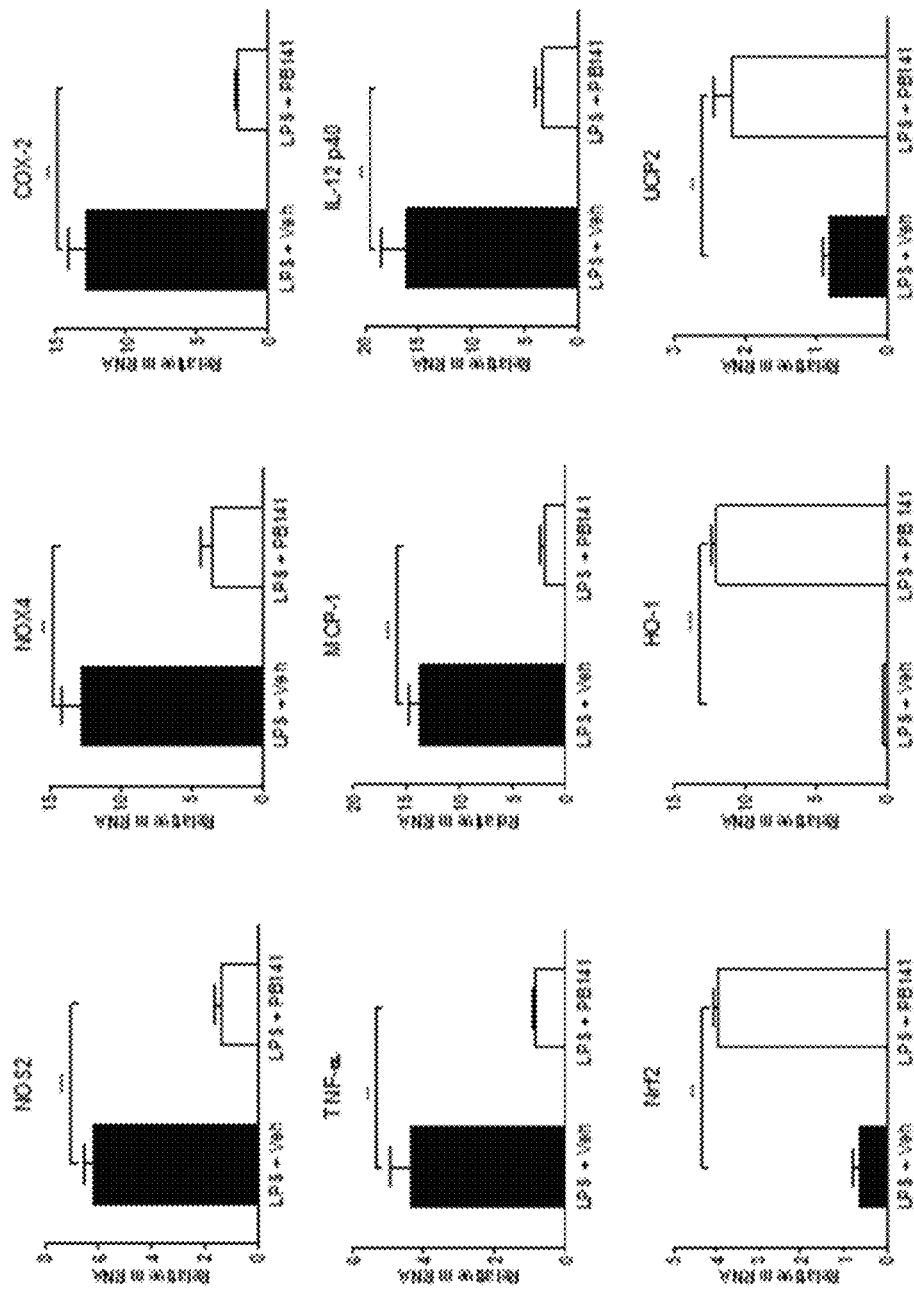
FIG. 13 shows that PB141 reduces inflammatory gene and increases antioxidant gene transcription in LPS-activated alveolar macrophages. Induction of ALI by intratracheal injection of LPS (50 μg) was followed 30 min later by nebulization of PB141 (25 mg/kg) or vehicle (saline) and delivery to cage air via a micropump nebulizer. After another 5.5 h BAL fluid was obtained. Alveolar macrophages were isolated from the BAL fluid and plated in DMEM+10% FBS. After 1 h, RNA was isolated and expression of the indicated genes was determined using real-time PCR; results were normalized to values for the housekeeping genes glyceraldehyde-3-phosphate dehydrogenase (GAPDH) and 9s rRNA. Data are representative of one of two independent experiments with n=6-8 mice per group; P<0.01; *P<0.001.

For additional in vitro studies, after the treatment described above alveolar macrophages were isolated from the BAL fluid and plated in DMEM+10% FBS. After 1 h, RNA was isolated and expression of the different genes was determined using real-time PCR; results were normalized to values for the housekeeping genes glyceraldehyde-3-phosphate dehydrogenase (GAPDH) and 9s rRNA. Macrophages from mice treated with PB141 showed decreased transcription of inflammatory genes and increased transcription of antioxidant genes (FIG. 13). In other experiments, PMNs were isolated from peripheral blood of endotoxin-treated mice by hetastarch exchange transfusion. PMN adhesion was assessed with the Cytoselect Leukocyte-Endothelium Adhesion Assay kit (CBA-210; Cell Biolabs) and transendothelial PMN migration was determined with the Cytoselect Leukocyte Transmigration Assay kit (CBA-212; Cell Biolabs). Cells from mice treated with PB141 showed decreased PMN adhesion and transendothelial migration.

Example 15

Nebulization of a PB141 Solution Provides Efficient Delivery into the Lungs and Prevents Lung Cancer A/J mice were injected intraperitoneally on days 1, 3, and 5 with 50 mg/kg of 4-methylnitrosamino-1-(3-pyridyl)-1-butanone (NNK; Chemsyn Science Laboratories, Lenexa, Kans.) dissolved in saline. The mice were then held for 8 weeks to allow development of preinvasive lesions: alveolar hyperplasias and adenomas. In some experiments cancer was induced by X-ray irradiation as follows: The mice were placed into a polycarbonate cage and separated with hard paper. Whole body irradiation for systemic damage was performed using a linear accelerator (MEVATRON PRIMUS®; SIEMENS Medical Solutions, CA, USA) that produces 6 MV photons. The linear accelerator was positioned at a source-to-skin distance of 100 cm and irradiation was delivered at a dose rate of 3.0 Gy/min. PB141 (25 mg/kg) or vehicle (saline) was delivered to mice for 30 min/day for eight weeks via a micropump nebulizer (Buxco Research Systems, Wilmington, N.C.).

Figure 14A:
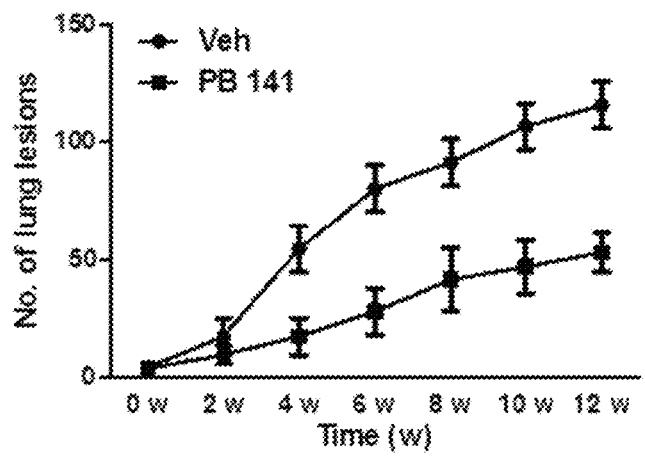
FIGS. 14A-14B show that nebulized PB141 reduces 4-methylnitrosamino-1-(3-pyridyl)-1-butanone (NNK)-induced lung tumorigenesis in A/J mice. Induction of lung tumorigenesis by intraperitoneal (i.p.) injection on days 1, 3, and 5 with 50 mg/kg of NNK dissolved in saline was followed by nebulization of PB141 (25 mg/kg) or vehicle (saline) and delivery to cage air via a micropump nebulizer. After 8 weeks the lung was examined histologically following H&E staining (FIG. 14A) Number of lung lesions.
Figure 14B:
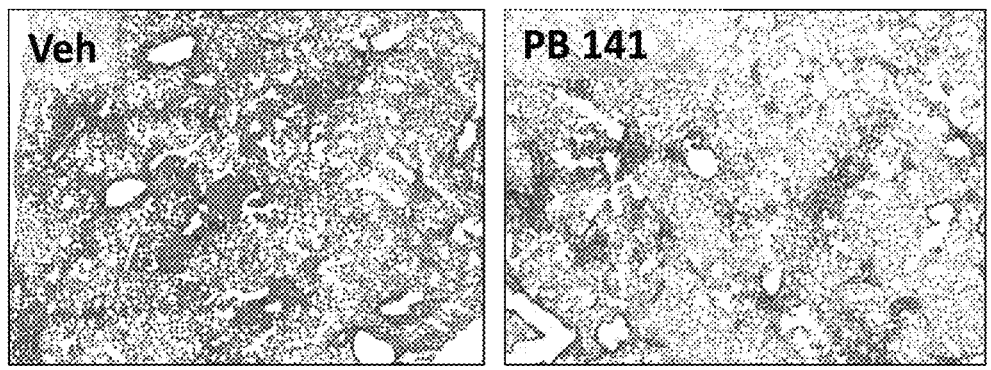

Mice were euthanized following the eight-week treatment period. Lung histology sections were stained by hematoxylin and eosin (H&E). Lung lesions were quantified by determining the incidence and prevalence of pulmonary pleural surface tumors, counting both the right and left lungs of each mouse. The researcher performing adenoma assessment was blind to the treatment employed. Hyperplastic and neoplastic lesions of the lungs were scored according to the International Classification of Rodent Tumors in 6 or 7 sections per lung. Sections were further assessed for morphometry and Ki67 immunohistochemistry. Delivery of PB141 significantly (~40%) inhibited tumor progression, premalignant lung cancer, and cell proliferation in the A/J mouse model (FIG. 14).

For further in vitro studies, human lung adenocarcinoma cell lines (NCI-H661, NCI-H441 and NCIH1299) were obtained from American Type Culture Collection. Cells were treated with 1 μM NNK for 1 hr. In some experiments cells were pretreated with 1 to 5 μM PB141 before treatment with NNK. Cell proliferation was assessed by BrdU proliferation kit (Roche Applied Science). Apoptosis was assessed by TUNEL assay. Treatment with PB141 significantly decreased cell proliferation and induced apoptosis in NNK-induced lung adenocarcinoma cells (data not shown).

Example 16

Nebulization of a PB141 Solution Provides Efficient Delivery into the Lungs and Prevents COPD Mice were exposed 5 days per week for 4 wk (sub-acute exposure) to the smoke of five cigarettes (Reference Cigarette 2R4F without filter; University of Kentucky) administered four times per day with a 30-min smoke-free interval between exposures. An optimal smoke:air ratio of 1:6 was obtained. In preventive studies, tobacco smoke exposure was paralleled by delivery of a nebulized solution containing PB141 (25 mg/kg) or vehicle (saline) via a micropump nebulizer (Buxco Research Systems, Wilmington, N.C.). At the conclusion of smoke exposure the extent of lung inflammation was assessed by counting polymorphonuclear neutrophils (PMNs) in bronchoalveolar lavage fluid and measuring lung vascular permeability, edema, pulmonary lymphoid aggregation, and generation of inflammatory chemokines and cytokines. Emphysema was assessed by destruction of alveolar walls, quantitated as the destructive index (DI), and by enlargement of alveolar spaces, quantitated by the mean linear intercept (Lm). Airway remodeling was assessed by staining collagen in the airway wall and by measuring the amount of fibronectin. Lung histology sections were assessed for inflammation and injury following hematoxylin and eosin (H&E) staining Lymphoid aggregates were quantification by morphometric analysis.

Figure 18:
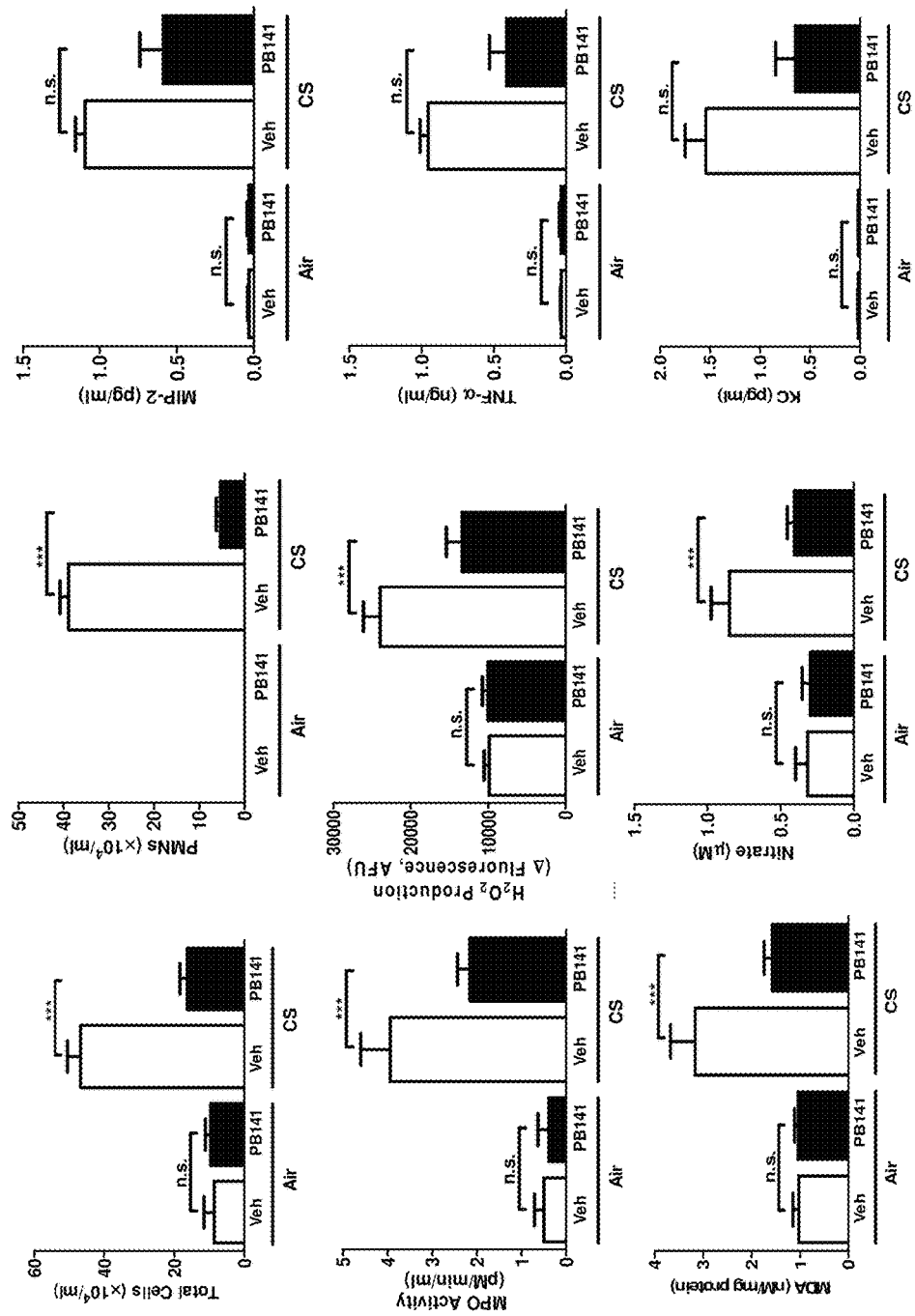
FIG. 18 shows that nebulized PB141 reduces infiltration of inflammation-related cells into pulmonary spaces and production of inflammatory mediators in a murine model of chronic obstructive pulmonary disease (COPD). COPD was induced by exposure of mice to whole-body cigarette smoke for 5 days, at the end of which the mice were euthanized and cells and levels of mediators were obtained from the pulmonary airspace by bronchoalveolar lavage. Some mice received PB141 (25 mg/kg) simultaneously with the cigarette smoke (A-I).

As shown in FIG. 18, delivery of a nebulized PB141 solution significantly decreased the cigarette smoke-induced increases of inflammatory cells in the lungs, pulmonary lymphoid aggregates, generation of inflammatory chemokines and cytokines, airway wall remodeling, development of pulmonary hypertension, and emphysema. Furthermore, administration of PB141 by nebulization improved the phagocytic ability of alveolar macrophages.

For further in vitro studies, bronchial epithelial cells, THP cells (obtained from American Type Culture Collection), and alveolar macrophages (isolated from bronchial lavage fluid of humans and mice) were cultured and exposed to 10% cigarette smoke extract (CSE) prepared by smoking two cigarettes into RPMI medium according to the Federal Trade Commission (FTC) protocol. In some experiments cells were pretreated with 1 to 5 µM PB141 before the cigarette smoke extract treatment. Pretreatment with PB141 decreased epithelial cell permeability, inflammatory chemokine and cytokine production, and ROS generation. It also improved the phagocytic ability of mouse and human alveolar macrophages.

Example 17

Nebulization of a PB141 Solution Provides Efficient Delivery into the Lungs and Prevents Asthma Allergen induced asthma was produced in mice by initial sensitization by intraperitoneal injection of OVA on days 0 and 7 and challenge by intratracheal injection of OVA on even-numbered days 14 through 22. Thirty minutes following each OVA challenge, PB141 (25 mg/kg) or vehicle (saline) was nebulized into the cage air for 30 min. Twenty-four hours following the last challenge and nebulization. airway hyperresponsiveness to methacholine challenge was measured noninvasively by whole body plethysmography (WBP; Buxco Research Systems, Wilmington, N.C.) and, invasively by computer-controlled ventilator (flexiVent; SCIREQ Inc., Montreal, Canada). Cellular Infiltration into the airspace was assessed by measuring myeloperoxidase activity in the lung and the number of polymorphonuclear neutrophils and eosinophils in bronchoalveolar lavage fluid (BALF). Lung inflammation was assessed by vascular permeability, edema, and cytokine generation. Anti-OVA IgE concentrations in the serum were measured using an ELISA kit (MD Bioproducts, St. Paul, Minn.). Lung histology sections were assessed by morphometry, with May-Grünwald-Giemsa or Periodic acid-Schiff (PAS) staining used for detection of mucopolysaccharide accumulation, Sirius Red or Masson's trichrome staining for detection of collagen deposition, and hematoxylin and eosin (H&E) staining for assessment of inflammation. Lung collagen content was determined by quantifying soluble collagen with the Sircol Collagen Assay Kit (Biocolor).

Figure 15A:
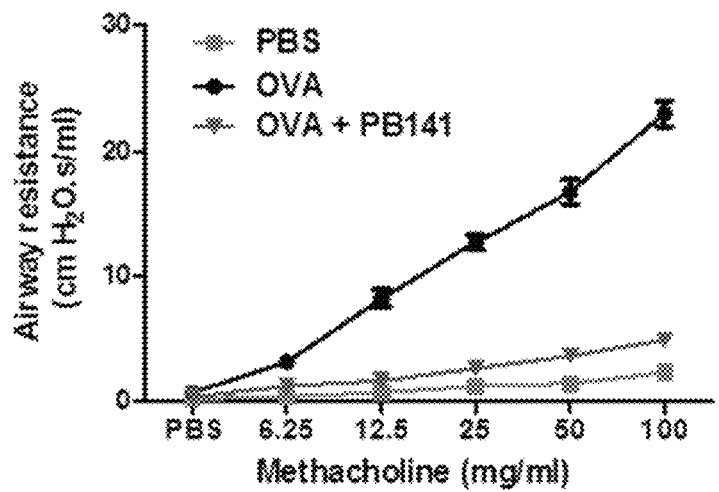
FIGS. 15A-15B show that nebulized PB141 reduces ovalbumin (OVA)-induced airway hyperresponsiveness. Allergen-induced asthma was produced in mice by initial sensitization by intraperitoneal (i.p.) injection of OVA on days 0 and 7 and challenge by intratracheal injection of OVA on even-numbered days 14 through 22. Thirty minutes following each OVA challenge, PB141 (25 mg/kg) or vehicle (saline) was nebulized and delivered to cage air via a micropump nebulizer. Twenty-four hours after the last challenge and nebulization; airway hyperresponsiveness to increasing concentrations of inhaled methacholine was determined by the forced oscillation (flexiVent) method.
Figure 15B:
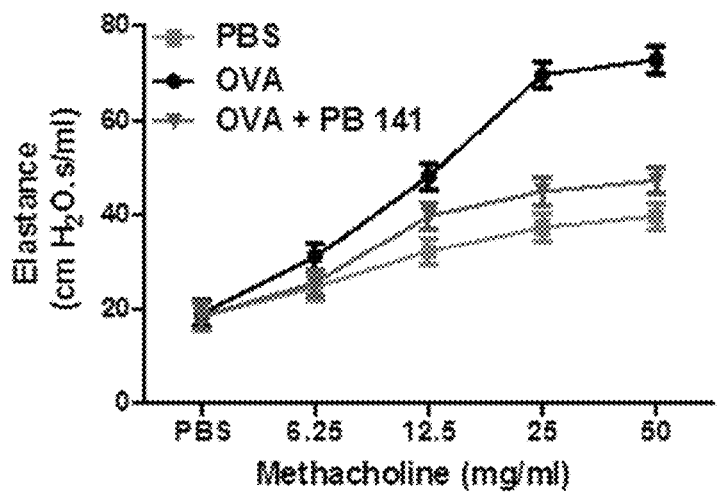
Figure 16A:
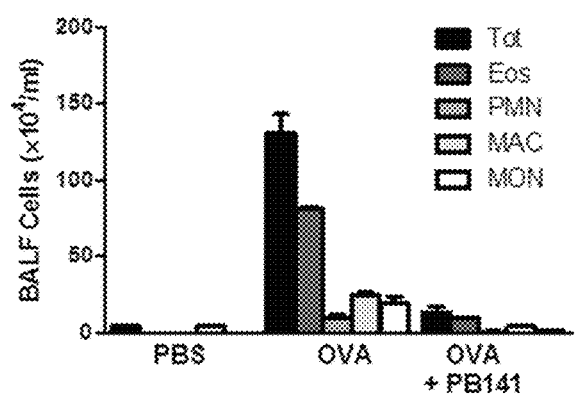
FIGS. 16A-16D show that nebulized PB141 reduces ovalbumin (OVA)-induced lung inflammation and oxidative damage. Allergen induced asthma was produced in mice by initial sensitization by intraperitoneal (i.p.) injection of OVA on days 0 and 7 and challenge by intratracheal injection of OVA on even-numbered days 14 through 22. Thirty minutes after each OVA challenge, PB141 (25 mg/kg) or vehicle (saline) was nebulized and delivered to cage air via a micropump nebulizer. Twenty-four hours following the last challenge and nebulization, BAL fluid, plasma, and lung samples were obtained.
Figure 16B:
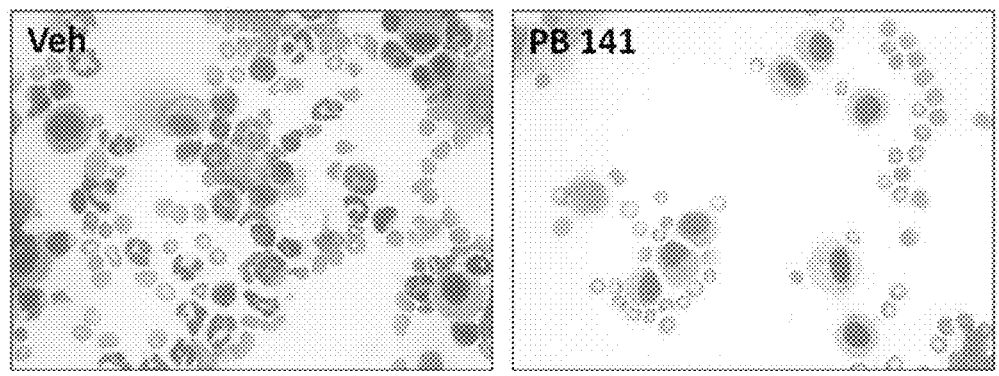
Figure 16C:
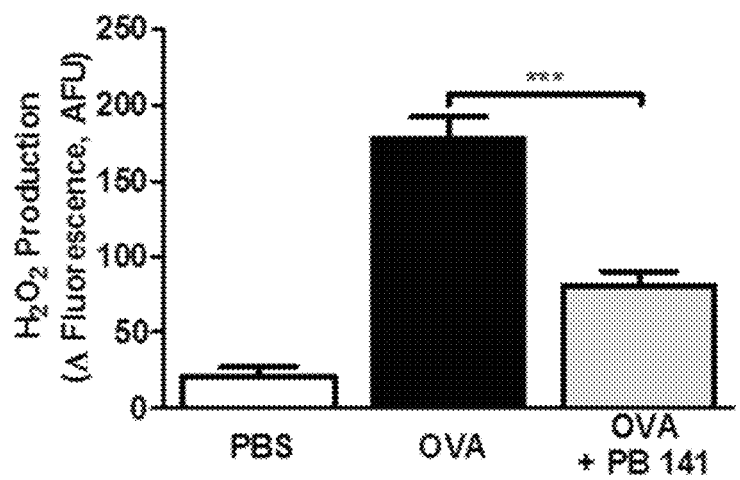
Figure 16D:
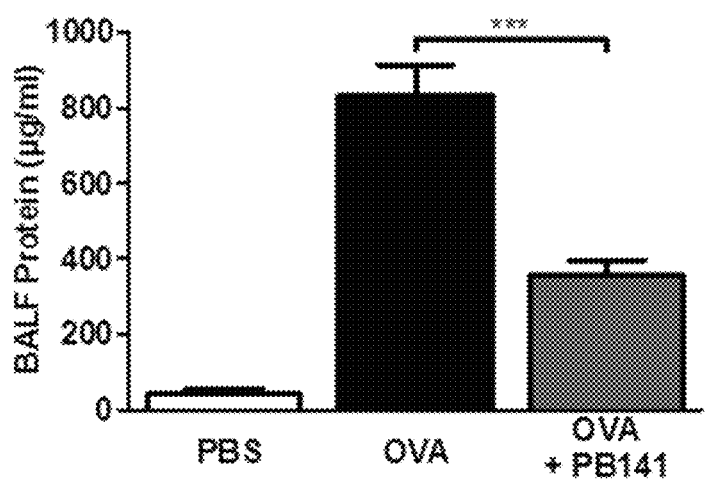
Figure 17A:
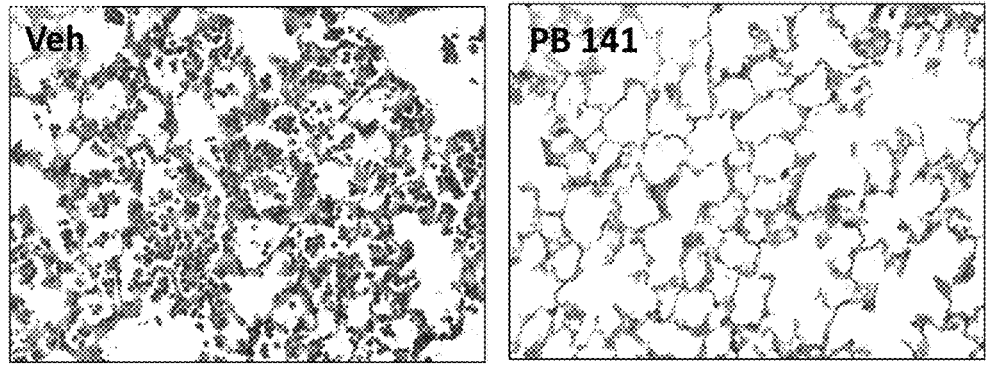
FIGS. 17A-17C show that nebulized PB141 reduces ovalbumin (OVA)-induced inflammatory cell infiltration and mucus production. Allergen-induced asthma was produced in mice by initial sensitization by intraperitoneal (i.p.) injection of OVA on days 0 and 7 and challenge by intracheal injection of OVA on even-numbered days 14 through 22. Thirty minutes after each OVA challenge, PB141 (25 mg/kg) or vehicle (saline) was nebulized and delivered to cage air via a micropump nebulizer. Twenty-four hours following the last challenge and nebulization lung samples were obtained. The lung was examined histologically following (FIG. 17A) H&E staining, (FIG. 17B) trichrome staining, and (FIG. 17C) periodic acid Schiffs (PAS) staining Data are representative of one of two independent experiments with n=7-10 mice per group.
Figure 17B:
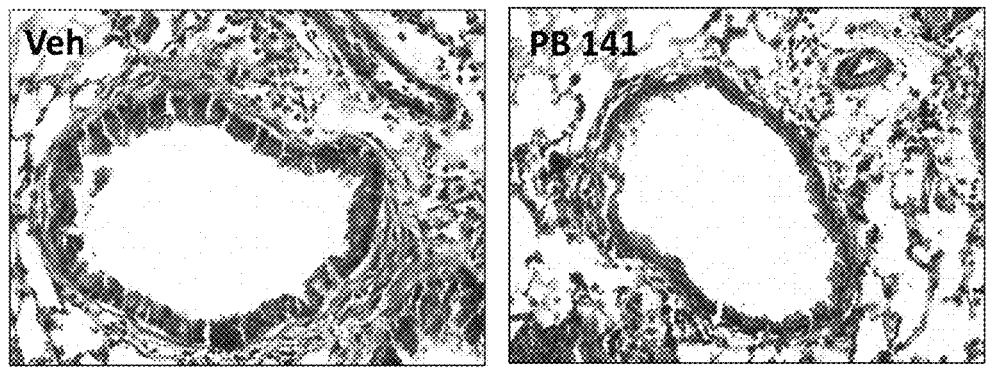
Figure 17C:
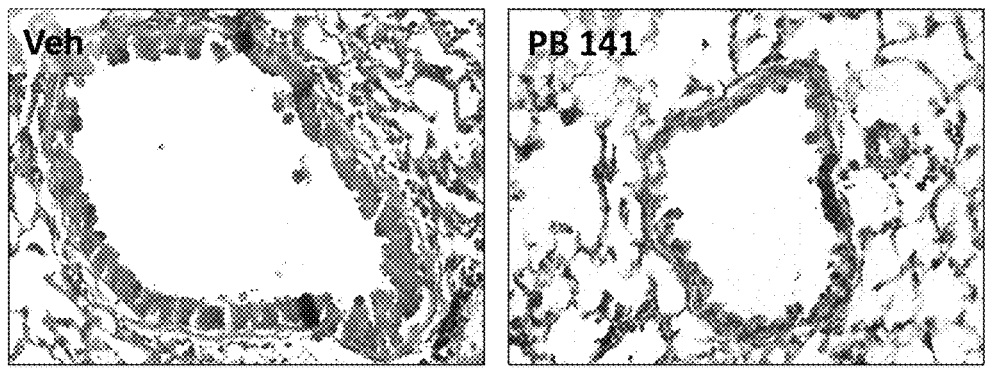

As shown in FIGS. 15-17, nebulized delivery of the PB141 solution significantly suppressed airway hyperresponsiveness while lessening airway remodeling and mucus accumulation. It suppressed the infiltration of inflammatory cells into the airspace and lung and attenuated the expression of cytokines, chemokines, and IgE in BALF and serum. PB141 administration also inhibited cytokine generation, iNOS expression, and NO production in lung epithelial cells (BEAS2B) stimulated with 10 ng/ml IFN-γ or IL-4/IL-13 for 6 h.

Example 18

Nebulization of a PB141 Solution Provides Efficient Delivery into the Lungs and Prevents Pulmonary Hypertension Pulmonary hypertension was induced in mice by exposing them to chronic hypoxia ($Fi_{O_2}$ 10%) for 3 weeks. Control mice breathed room air during the last 10 days of exposure, PB141 (25 mg/kg) or vehicle (saline) was nebulized into the cage air for 30 min via a nebulizer.

Pulmonary Delivery of PB141 Reduces Right Ventricular Systolic Pressure in Chronic Hypoxia-Induced Pulmonary Hypertension.

Figure 19:
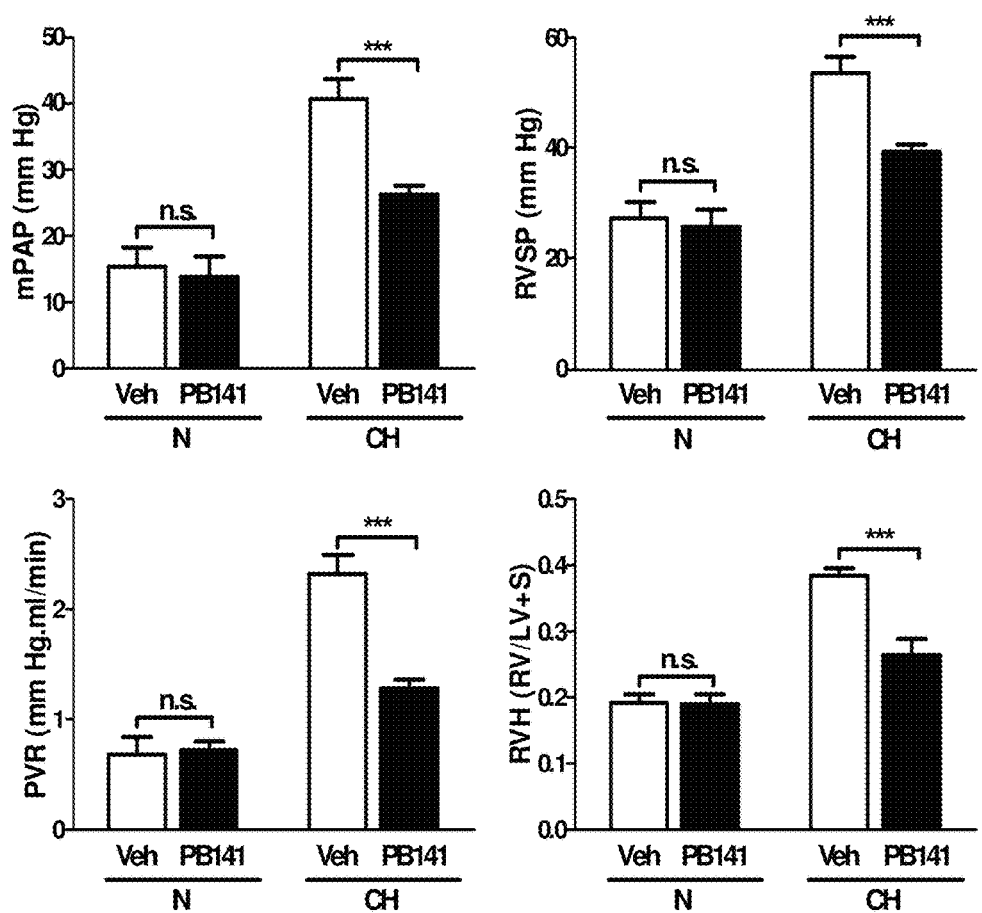
FIG. 19 shows that nebulized PB141 reduces chronic hypoxia (CH)-induced pulmonary hypertension and right ventricular hypertrophy. CH-induced pulmonary hypertension was produced in mice by exposing them to chronic hypoxia (CH; $FI_{O2}$ 10%) or room air (N; control) for 3 weeks. During the last 10 days of exposure, PB141 (25 mg/kg) or vehicle (saline) was nebulized and delivered to cage air via a micropump nebulizer. Twenty-four hours following the last nebulization mice were anesthetized and the right internal jugular vein of each mouse was surgically exposed and cannulated with a pressure transducer that was advanced to record right ventricular pressure, then advanced further to measure pulmonary arterial pressure: (top left) mean pulmonary arterial pressure; (top right) right ventricular systolic pressure (RVSP); (bottom left) peripheral vascular resistance; (bottom right) right ventricular hypertrophy. Data are representative of one of two independent experiments with n=4-6 mice per group.

Twenty-four hours following the last PB141 administration, mice were anesthetized, and the right internal jugular vein of each mouse was surgically exposed and cannulated with a pressure transducer that was advanced to record right ventricular systolic pressure (RVSP), which is elevated in pulmonary hypertension. Pressure increases were significantly smaller in PB141-treated mice, as were pulmonary arterial pressure and pulmonary vascular resistance. The heart was then excised and the right ventricle was separated from the left ventricle (including the septum). Each ventricle was weighted separately. Pulmonary hypertension induces right ventricular hypertrophy, but PB141 treatment significantly reduced the increase in ratio of right ventricular weight to that of the left ventricle plus septum (FIG. 19).

Pulmonary Delivery of PB141 Reduces Vascular Remodeling in Chronic Hypoxia-Induced Pulmonary Hypertension.

Figure 20:
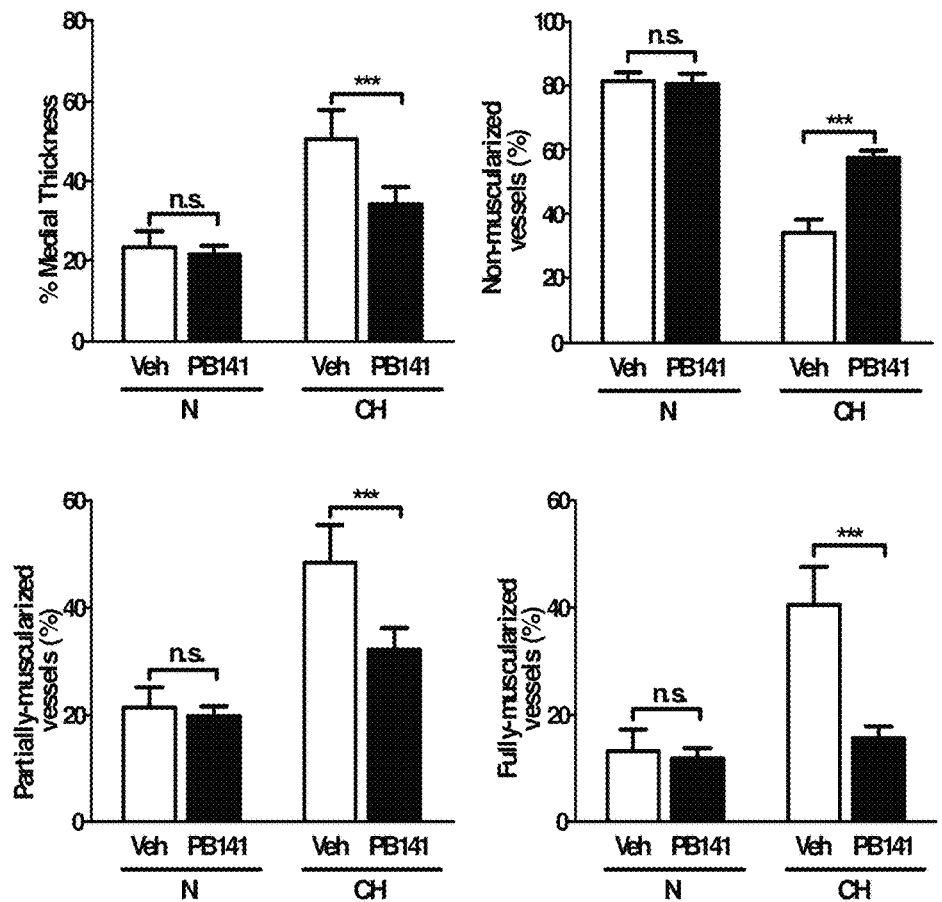
FIG. 20 shows that nebulized PB141 reduces chronic hypoxia (CH)-induced pulmonary hypertension and vascular remodeling. CH-induced pulmonary hypertension was produced in mice by exposing them to CH ($FI_{O2}$ 10%) or room air for 3 weeks. During the last 10 days of exposure, PB141 (25 mg/kg) or vehicle (saline) was nebulized and delivered to cage air via a micropump nebulizer. Twenty-four hours following the last nebulization lung samples were obtained. Graphs show medial wall thickness of a-SMA-positive acinar blood vessels and percent of non-muscularized, partially muscularized, and fully muscularized small vessels. Data are representative of one of two independent experiments with n=4-6 mice per group.
Figure 21:
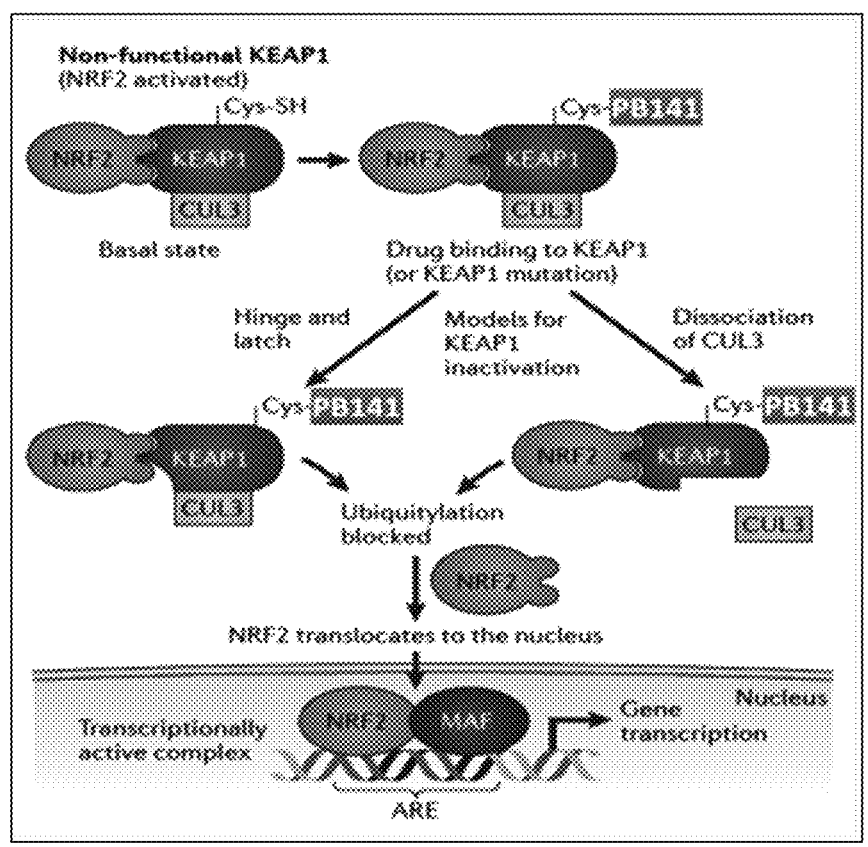
FIG. 21 shows the proposed mechanism of action of PB141.

Twenty-four hours following the last PB141 administration, lung samples were obtained. Immunostaining for α-SMA, a key marker in pulmonary hypertension, was performed in paraffin sections of lung and the sections were examined microscopically. The number of α-SMA-positive acinar blood vessels was quantified and the number demonstrating no, partial, or full muscularization was determined, as was the median wall thickness of vessels positive for α-SMA. All these measures of vascular wall remodeling in small pulmonary vessels, the pathophysiology underlying pulmonary hypertension, were reduced by PB141 treatment (FIG. 20).

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating a pulmonary disease in a subject comprising administering to the subject in need thereof a therapeutically effective amount of a compound, or a pharmaceutically acceptable salt or ester thereof, having a structure of:

(Formula I)

$$X^1-A\overset{O}{\underset{}{\diagdown\!\!\diagup}}A-X^2$$

wherein ===== represents a single bond;

A is $CH(S-R^5)$, wherein $R^5$ is an acylamino-substituted carboxylalkyl, a sulfonate-substituted alkyl, or an acylamino-substituted amido; and $X^1$ and $X^2$ are each independently an optionally-substituted N-heterocycle wherein the pulmonary disease is pulmonary fibrosis, chronic obstructive pulmonary disease (COPD), asthma, cystic fibrosis, acute lung injury (ALI), acute respiratory distress syndrome, pulmonary hypertension, lung cancer, or pulmonary manifestations of cystic fibrosis.

2. The method of claim 1, wherein $X^1$ has a structure of:

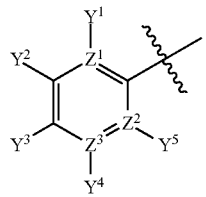

and $X^2$ has a structure of:

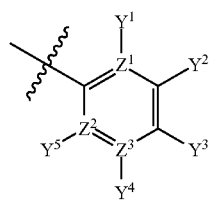

wherein $Z^1$, $Z^2$, and $Z^3$ are each independently C or N, provided that at least one of $Z^1$, $Z^2$, or $Z^3$ is N; and $Y^1$, $Y^2$, $Y^3$, $Y^4$ and $Y^5$ are each independently H, optionally-substituted alkyl, amino, hydroxyl, optionally-substituted alkoxy, optionally-substituted thiol, acyl, or halogen.

3. The method of claim 1, wherein the compound has a structure of:

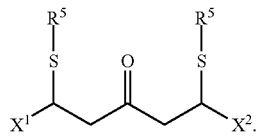

4. The compound of 3, wherein the compound has a structure of:

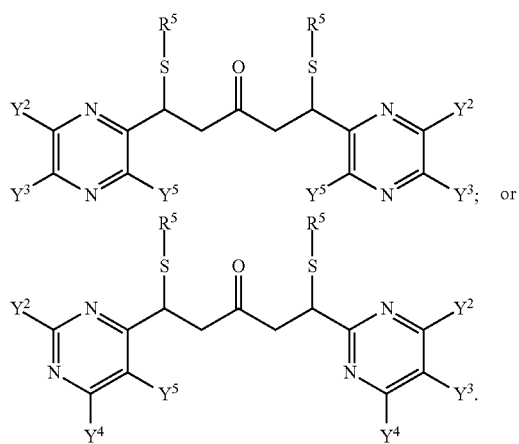

wherein $Y^2$, $Y^3$, $Y^4$ and $Y^5$ are each independently H, optionally-substituted alkyl, amino, hydroxyl, optionally-substituted alkoxy, optionally-substituted thiol, acyl, or halogen.

5. The method of claim 1, wherein $X^1$ and $X^2$ are each optionally-substituted pyrazinyl or optionally-substituted pyrimidinyl.

6. The method of claim 1, wherein $X^1$ and $X^2$ are each the same.

7. The method of claim 1, wherein $X^1$ and $X^2$ are each different.

8. The method of claim 1, wherein S—$R^5$ is a N-acetylcysteine moiety, a 2-mercaptoethane sulfonate moiety, or a glutathione moiety.

9. The method of claim 1, wherein the compound has a structure of:

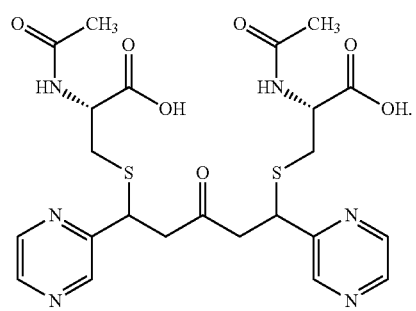 [SMILES: CC(=O)N[C@@H](CSC(CC(=O)CC(SC[C@H](NC(C)=O)C(=O)O)c1cnccn1)c1cnccn1)C(=O)O]

10. The method of claim 1, wherein the compound has a structure of:

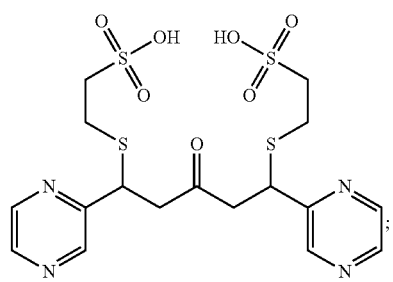

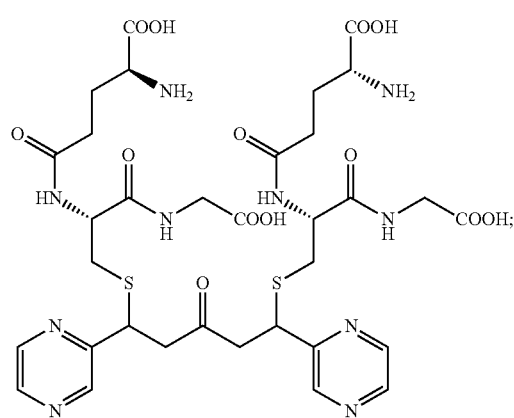

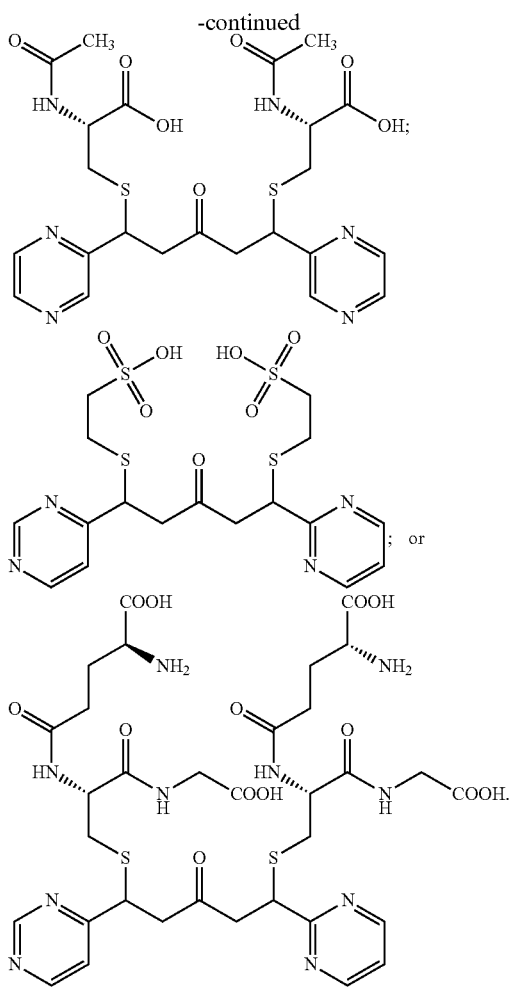

11. The method of claim 1, wherein the compound is administered to the subject via inhalation.

12. The method of claim 1, wherein the compound is administered via direct pulmonary delivery.

13. The method of claim 9, wherein the compound is administered to the subject via inhalation.

14. A method of inhibiting NF-κB activity in a subject, inhibiting lung fibroblast proliferation in a subject, inhibiting myofibroblast differentiation in a subject, inhibiting an oxidizing agent in lung tissue of a subject, ameliorating acute or chronic rejection of a transplanted organ in a subject, increasing a subject's endogenous antioxidant activity via upregulation of the activity of the transcription factor Nrf2, inhibiting pulmonary collagen deposition in a subject, diminishing the inflammatory response to allergen in a subject, diminishing the inflammatory response to an inflammatory, irritating, or cytotoxic agent in a subject, diminishing allergen-induced excessive response to bronchoconstrictors in a subject, diminishing allergen-induced airway remodeling in a subject, or diminishing hypoxia-induced remodeling of the pulmonary vasculature in a subject, comprising administering to the subject in need thereof a therapeutically effective amount of a compound, or a pharmaceutically acceptable salt or ester thereof, having a structure of:

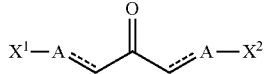

(Formula I)

wherein ═════ represents a single bond;
A is CH(S—R$^5$), wherein R$^5$ is an acylamino-substituted carboxylalkyl, a sulfonate-substituted alkyl, an acylamino-substituted amido; and
X$^1$ and X$^2$ are each independently an optionally-substituted N-heterocycle.

15. A method for decreasing proliferation and inducing apoptosis in lung cancer cells, comprising contacting the cells with an effective amount of a compound, or a pharmaceutically acceptable salt or ester thereof, having a structure of:

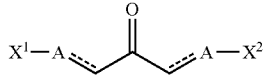

(Formula I)

wherein ═════ represents a single bond;
A is CH(S—R$^5$), wherein R$^5$ is an acylamino-substituted carboxylalkyl, a sulfonate-substituted alkyl, an acylamino-substituted amido; and
X$^1$ and X$^2$ are each independently an optionally-substituted N-heterocycle.

16. A method for improving the phagocytotic ability of alveolar macrophages, comprising contacting the microphages with an effective amount of a compound, or a pharmaceutically acceptable salt or ester thereof, having a structure of:

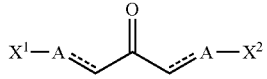

(Formula I)

wherein ═════ represents a single bond;
A is CH(S—R$^5$), wherein R$^5$ is an acylamino-substituted carboxylalkyl, a sulfonate-substituted alkyl, an acylamino-substituted amido; and
X$^1$ and X$^2$ are each independently an optionally-substituted N-heterocycle.

17. The method of claim 1, wherein the pulmonary disease is chronic obstructive pulmonary disease (COPD).

18. The method of claim 5, wherein the pulmonary disease is chronic obstructive pulmonary disease (COPD).

19. The method of claim 9, wherein the pulmonary disease is chronic obstructive pulmonary disease (COPD).

20. The method of claim 17, wherein the compound is administered to the subject via inhalation.

* * * * *